US007223274B2

(12) United States Patent
Vargas et al.

(10) Patent No.: US 7,223,274 B2
(45) Date of Patent: May 29, 2007

(54) METHOD OF PERFORMING ANASTOMOSIS

(75) Inventors: Jaime S. Vargas, Menlo Park, CA (US); Stephen A. Yencho, Menlo Park, CA (US); James T. Nielsen, San Francisco, CA (US); Brendan M. Donohoe, San Francisco, CA (US); Theodore M. Bender, San Francisco, CA (US); Brian R. DuBois, Redwood City, CA (US); Scott O. Chamness, Menlo Park, CA (US); Nathan H. White, Palo Alto, CA (US); Gregory B. Arcenio, Redwood City, CA (US); Heather L. Klaubert, Decatur, GA (US); Russell C. Mead, Jr., Mountain View, CA (US)

(73) Assignee: Cardica, Inc., Redwood City, CA (US)

( * ) Notice: Subject to any disclaimer, the term of this patent is extended or adjusted under 35 U.S.C. 154(b) by 350 days.

(21) Appl. No.: 10/934,883

(22) Filed: Sep. 3, 2004

(65) Prior Publication Data

US 2005/0033330 A1    Feb. 10, 2005

Related U.S. Application Data

(60) Division of application No. 10/057,795, filed on Jan. 23, 2002, now Pat. No. 7,029,482, and a continuation-in-part of application No. 10/054,795, filed on Jan. 25, 2002, now Pat. No. 6,686,427.

(51) Int. Cl.
*A61B 17/08* (2006.01)
*A61B 7/10* (2006.01)
(52) U.S. Cl. ..................... 606/153; 606/139

(58) Field of Classification Search ............... 606/153, 606/167, 17, 148, 139, 149, 184, 185, 188, 606/189; 623/1.11, 1.23; 227/19, 179.1
See application file for complete search history.

(56) References Cited

U.S. PATENT DOCUMENTS 3,254,650 A    6/1966   Collito (Continued)

FOREIGN PATENT DOCUMENTS

DE    4041262    7/1991

(Continued)

OTHER PUBLICATIONS

"Cardica PAS-Port Proximal Anastomosis System 510(k)", Section VI.C., "Substantial Equivalence", and Attachment 7 (Unpublished).

(Continued)

*Primary Examiner*—Michael J. Hayes
*Assistant Examiner*—Christina Gettman
(74) *Attorney, Agent, or Firm*—Brian A. Schar

(57) ABSTRACT

A method for performing anastomosis between a graft vessel and a target vessel with an integrated anastomosis tool may include actuating at least one control on the integrated anastomosis tool to create an opening in the target vessel and complete an anastomosis with the target vessel. Another method for performing anastomosis may include creating an opening in intact tissue of the target vessel with an integrated anastomosis tool; and deploying an anastomosis device with the integrated anastomosis tool. The anastomosis may be performed with an anastomosis device, such as an anastomosis device having a deployable section detachable from a discard section.

12 Claims, 34 Drawing Sheets

U.S. PATENT DOCUMENTS

| | | |
|---|---|---|
| 3,519,187 A | 7/1970 | Kapitanov et al. |
| 3,577,979 A | 5/1971 | van der Gaast |
| 3,774,615 A | 11/1973 | Lim et al. |
| 3,825,362 A | 7/1974 | Hougen |
| 4,018,228 A | 4/1977 | Goosen |
| 4,076,162 A | 2/1978 | Kapitanov et al. |
| 4,118,806 A | 10/1978 | Porier et al. |
| 4,214,587 A | 7/1980 | Sakura, Jr. |
| 4,216,776 A | 8/1980 | Downie et al. |
| 4,217,664 A | 8/1980 | Faso |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,534,761 A | 8/1985 | Raible |
| 4,553,542 A | 11/1985 | Schenck et al. |
| 4,589,416 A | 5/1986 | Green |
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,721,109 A | 1/1988 | Healey |
| 4,747,407 A | 5/1988 | Liu et al. |
| 4,752,024 A | 6/1988 | Green et al. |
| 4,873,991 A | 10/1989 | Skinner |
| 4,883,453 A | 11/1989 | Berry et al. |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 5,005,749 A | 4/1991 | Aranyi |
| 5,062,842 A | 11/1991 | Tiffany |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,171,262 A | 12/1992 | Macgregor |
| 5,178,634 A | 1/1993 | Martinez |
| 5,187,796 A | 2/1993 | Wang et al. |
| 5,192,289 A | 3/1993 | Jessen |
| 5,192,294 A | 3/1993 | Blake, III |
| 5,193,731 A | 3/1993 | Aranyi |
| 5,205,459 A | 4/1993 | Brinkerhoff et al. |
| 5,217,474 A | 6/1993 | Zacca et al. |
| 5,221,281 A | 6/1993 | Klicek |
| 5,222,963 A | 6/1993 | Brinkerhoff et al. |
| 5,234,447 A | 8/1993 | Kaster et al. |
| 5,250,058 A * | 10/1993 | Miller et al. ............... 606/154 |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Martinez |
| 5,324,300 A | 6/1994 | Elias et al. |
| 5,333,773 A | 8/1994 | Main et al. |
| 5,336,233 A | 8/1994 | Chen |
| 5,344,059 A | 9/1994 | Green et al. |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,403,338 A | 4/1995 | Milo |
| 5,423,330 A | 6/1995 | Lee |
| 5,423,796 A | 6/1995 | Shikhman et al. |
| 5,423,846 A | 6/1995 | Fischell |
| 5,443,497 A | 8/1995 | Venbrux |
| 5,447,514 A | 9/1995 | Gerry et al. |
| 5,454,825 A | 10/1995 | van Leeuwen |
| 5,456,712 A | 10/1995 | Maginot |
| 5,456,714 A | 10/1995 | Owen |
| 5,462,062 A | 10/1995 | Rubinstein et al. |
| 5,464,449 A | 11/1995 | Ryan et al. |
| 5,465,895 A | 11/1995 | Knodel et al. |
| 5,470,320 A | 11/1995 | Tiefenbrun et al. |
| 5,478,354 A | 12/1995 | Tovey et al. |
| 5,488,958 A | 2/1996 | Topel et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| D372,310 S | 7/1996 | Hartnett |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,591,187 A | 1/1997 | Dekel |
| 5,643,340 A | 7/1997 | Nunokawa |
| 5,645,520 A | 7/1997 | Nakamura et al. |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,690,662 A | 11/1997 | Chiu et al. |
| 5,693,088 A | 12/1997 | Lazarus |
| 5,695,504 A * | 12/1997 | Gifford et al. ............... 606/153 |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,755,778 A | 5/1998 | Kleshinski |
| 5,762,458 A | 6/1998 | Wang et al. |
| 5,779,718 A | 7/1998 | Green et al. |
| 5,782,853 A | 7/1998 | Zeevi et al. |
| 5,792,135 A | 8/1998 | Madhani et al. |
| 5,797,900 A | 8/1998 | Madhani et al. |
| 5,797,920 A | 8/1998 | Kim |
| 5,797,933 A | 8/1998 | Snow et al. |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,825,982 A | 10/1998 | Wright et al. |
| 5,827,316 A | 10/1998 | Young et al. |
| 5,833,698 A | 11/1998 | Hinchliffe et al. |
| 5,841,950 A | 11/1998 | Wang et al. |
| 5,855,583 A | 1/1999 | Wang et al. |
| 5,868,763 A | 2/1999 | Spence et al. |
| 5,868,764 A | 2/1999 | Rosengart |
| 5,871,495 A | 2/1999 | Mueller |
| 5,875,782 A | 3/1999 | Ferrari et al. |
| 5,878,193 A | 3/1999 | Wang et al. |
| 5,879,371 A | 3/1999 | Gardiner et al. |

| | | | | | | |
|---|---|---|---|---|---|---|
| 5,881,943 A | 3/1999 | Heck et al. | | 6,193,129 B1 | 2/2001 | Bittner et al. |
| 5,888,247 A | 3/1999 | Benetti | | 6,193,734 B1 | 2/2001 | Bolduc et al. |
| 5,893,369 A | 4/1999 | Lemole | | 6,206,912 B1 | 3/2001 | Goldsteen et al. |
| 5,895,403 A | 4/1999 | Collinsworth | | 6,206,913 B1 | 3/2001 | Yencho et al. |
| 5,895,404 A | 4/1999 | Ruiz | | 6,231,565 B1 | 5/2001 | Tovey et al. |
| 5,904,697 A | 5/1999 | Gifford, III et al. | | 6,235,054 B1 | 5/2001 | Berg et al. |
| 5,907,664 A | 5/1999 | Wang et al. | | 6,241,742 B1 | 6/2001 | Spence et al. |
| 5,910,121 A | 6/1999 | Paolo et al. | | 6,248,117 B1 | 6/2001 | Blatter |
| 5,910,153 A | 6/1999 | Mayenberger | | 6,253,768 B1 | 7/2001 | Wilk |
| 5,911,036 A | 6/1999 | Wright et al. | | 6,276,528 B1 | 8/2001 | Nowotny et al. |
| 5,915,616 A | 6/1999 | Viola et al. | | 6,293,955 B1 | 9/2001 | Houser et al. |
| 5,921,995 A | 7/1999 | Kleshinski | | 6,375,396 B1 | 4/2002 | Fangmann et al. |
| 5,944,730 A | 8/1999 | Nobles et al. | | 6,419,681 B1 | 7/2002 | Vargas et al. |
| 5,947,363 A | 9/1999 | Bolduc et al. | | 6,428,550 B1 | 8/2002 | Vargas et al. |
| 5,957,363 A | 9/1999 | Heck | | 6,461,320 B1 | 10/2002 | Yencho et al. |
| 5,968,089 A | 10/1999 | Krajicek | | 6,485,496 B1 | 11/2002 | Suyker et al. |
| 5,976,159 A | 11/1999 | Bolduc et al. | | 6,488,693 B2 | 12/2002 | Gannoe et al. |
| 5,976,178 A | 11/1999 | Goldsteen et al. | | 6,673,088 B1 | 1/2004 | Vargas et al. |
| 5,989,276 A | 11/1999 | Houser et al. | | 6,685,630 B2 | 2/2004 | Sauer et al. |
| 5,989,278 A | 11/1999 | Mueller | | 6,689,147 B1 | 2/2004 | Koster, Jr. |
| 6,001,124 A | 12/1999 | Bachinski | | 6,966,917 B1 | 11/2005 | Suyker et al. |
| 6,004,909 A | 12/1999 | Lindman | | 2001/0000903 A1 | 5/2001 | Heck |
| 6,007,544 A | 12/1999 | Kim | | 2001/0001122 A1 | 5/2001 | Gifford, III et al. |
| 6,013,190 A | 1/2000 | Berg et al. | | 2001/0001124 A1 | 5/2001 | Mueller |
| 6,015,416 A | 1/2000 | Stefanchik et al. | | 2001/0004697 A1 | 6/2001 | Blatter et al. |
| 6,022,367 A * | 2/2000 | Sherts ........................ 606/184 | | 2001/0004698 A1 | 6/2001 | Blatter et al. |
| 6,024,748 A | 2/2000 | Manzo et al. | | 2001/0016752 A1 | 8/2001 | Berg et al. |
| 6,025,015 A | 2/2000 | Landry-Coltrain et al. | | 2001/0023354 A1 | 9/2001 | Blatter et al. |
| 6,030,370 A | 2/2000 | Kupka et al. | | 2001/0029384 A1 | 10/2001 | Nicholas et al. |
| 6,030,395 A | 2/2000 | Nash et al. | | 2001/0037139 A1 | 11/2001 | Yencho et al. |
| 6,036,699 A | 3/2000 | Andreas et al. | | 2001/0047179 A1 | 11/2001 | Gifford, III et al. |
| 6,036,700 A | 3/2000 | Stefanchik et al. | | 2003/0065342 A1 | 4/2003 | Nobis |
| 6,036,702 A | 3/2000 | Bachinski et al. | | | | |
| 6,036,703 A | 3/2000 | Evans et al. | | FOREIGN PATENT DOCUMENTS | | |
| 6,036,704 A | 3/2000 | Yon | | | | |
| 6,036,705 A | 3/2000 | Nash et al. | | EP | 0517252 | 12/1992 |
| 6,036,710 A | 3/2000 | McGarry et al. | | EP | 0701800 | 3/1996 |
| 6,050,472 A | 4/2000 | Shibata | | EP | 0820724 | 1/1998 |
| 6,053,390 A | 4/2000 | Green et al. | | EP | 0885595 | 12/1998 |
| 6,056,762 A | 5/2000 | Nash et al. | | EP | 0938870 | 9/1999 |
| 6,066,144 A | 5/2000 | Wolf et al. | | EP | 0820725 | 1/2000 |
| 6,066,148 A | 5/2000 | Rygaard | | EP | 0990420 | 4/2000 |
| 6,068,637 A | 5/2000 | Popov et al. | | EP | 0913125 | 7/2000 |
| 6,074,416 A | 6/2000 | Berg et al. | | WO | WO-92/08513 | 5/1992 |
| 6,080,167 A | 6/2000 | Lyell | | WO | WO-96/25886 | 8/1996 |
| 6,080,173 A | 6/2000 | Williamson, IV et al. | | WO | WO-97/25002 | 7/1997 |
| 6,080,175 A | 6/2000 | Hogendijk | | WO | WO-97/27898 | 8/1997 |
| 6,080,176 A | 6/2000 | Young | | WO | WO-97/31575 | 9/1997 |
| 6,083,234 A | 7/2000 | Nicholas et al. | | WO | WO-97/47261 | 12/1997 |
| 6,083,238 A | 7/2000 | Alexander, Jr. et al. | | WO | WO-98/07399 | 2/1998 |
| 6,110,188 A | 8/2000 | Narciso, Jr. | | WO | WO-98/19608 | 5/1998 |
| 6,113,612 A | 9/2000 | Swanson et al. | | WO | WO-98/19618 | 5/1998 |
| 6,117,148 A | 9/2000 | Ravo et al. | | WO | WO-98/19625 | 5/1998 |
| 6,120,432 A | 9/2000 | Sullivan et al. | | WO | WO-98/19629 | 5/1998 |
| 6,146,393 A | 11/2000 | Wakabayashi | | WO | WO-98/19630 | 5/1998 |
| 6,149,681 A | 11/2000 | Houser et al. | | WO | WO-98/19631 | 5/1998 |
| 6,152,937 A | 11/2000 | Peterson et al. | | WO | WO-98/19632 | 5/1998 |
| 6,152,945 A | 11/2000 | Bachinski et al. | | WO | WO-98/19634 | 5/1998 |
| 6,165,185 A | 12/2000 | Shennib et al. | | WO | WO-98/19636 | 5/1998 |
| 6,167,889 B1 | 1/2001 | Benetti | | WO | WO-98/30153 | 7/1998 |
| 6,171,319 B1 | 1/2001 | Nobles et al. | | WO | WO-98/37814 | 9/1998 |
| 6,171,321 B1 | 1/2001 | Gifford, III et al. | | WO | WO-98/42262 | 10/1998 |
| 6,176,413 B1 | 1/2001 | Heck et al. | | WO | WO-98/47430 | 10/1998 |
| 6,176,864 B1 | 1/2001 | Chapman | | WO | WO-98/55027 | 12/1998 |
| 6,176,867 B1 | 1/2001 | Wright | | WO | WO-99/08603 | 2/1999 |
| 6,183,486 B1 | 2/2001 | Snow et al. | | WO | WO-99/17665 | 4/1999 |
| 6,186,942 B1 | 2/2001 | Sullivan et al. | | WO | WO-99/18887 | 4/1999 |
| 6,187,019 B1 | 2/2001 | Stefanchik et al. | | WO | WO-99/21491 | 5/1999 |
| 6,187,020 B1 | 2/2001 | Zegdi et al. | | WO | WO-99/37218 | 7/1999 |
| 6,190,392 B1 | 2/2001 | Vandewalle | | WO | WO-99/38441 | 8/1999 |
| 6,190,396 B1 | 2/2001 | Whitin et al. | | WO | WO-99/38454 | 8/1999 |
| 6,190,397 B1 | 2/2001 | Spence et al. | | WO | WO-99/40851 | 8/1999 |
| 6,190,590 B1 | 2/2001 | Randall et al. | | WO | WO-99/40868 | 8/1999 |

| | | | | | | |
|---|---|---|---|---|---|---|
| WO | WO-99/45848 | 9/1999 | | WO | WO-00/56228 | 9/2000 |
| WO | WO-99/52481 | 10/1999 | | WO | WO-00/59380 | 10/2000 |
| WO | WO-99/62406 | 12/1999 | | WO | WO-00/66007 | 11/2000 |
| WO | WO-99/62409 | 12/1999 | | WO | WO-00/66009 | 11/2000 |
| WO | WO-99/62415 | 12/1999 | | WO | WO-00/69343 | 11/2000 |
| WO | WO-99/63910 | 12/1999 | | WO | WO-00/69346 | 11/2000 |
| WO | WO-99/65409 | 12/1999 | | WO | WO-00/69349 | 11/2000 |
| WO | WO-00/09040 | 2/2000 | | WO | WO-00/69364 | 11/2000 |
| WO | WO-00/10486 | 3/2000 | | WO | WO-00/72764 | 12/2000 |
| WO | WO-00/12013 | 3/2000 | | WO | WO-00/74579 | 12/2000 |
| WO | WO-00/15144 | 3/2000 | | WO | WO-00/76405 | 12/2000 |
| WO | WO-00/15146 | 3/2000 | | WO | WO-01/08601 | 2/2001 |
| WO | WO-00/15147 | 3/2000 | | WO | WO-01/12074 | 2/2001 |
| WO | WO-00/15148 | 3/2000 | | WO | WO-01/15607 | 3/2001 |
| WO | WO-00/15149 | 3/2000 | | WO | WO-01/17440 | 3/2001 |
| WO | WO-00/27310 | 5/2000 | | WO | WO-01/19257 | 3/2001 |
| WO | WO-00/27311 | 5/2000 | | WO | WO-01/19259 | 3/2001 |
| WO | WO-00/27312 | 5/2000 | | WO | WO-01/19284 | 3/2001 |
| WO | WO-00/27313 | 5/2000 | | WO | WO-01/34037 | 5/2001 |
| WO | WO-00/33745 | 6/2000 | | | | |
| WO | WO-00/41633 | 7/2000 | | | | |
| WO | WO-00/53104 | 9/2000 | | | | |
| WO | WO-00/56223 | 9/2000 | | | | |
| WO | WO-00/56226 | 9/2000 | | | | |
| WO | WO-00/56227 | 9/2000 | | | | |

OTHER PUBLICATIONS

Sales training brochure entitled "CorLink Automated Anastomosis Device", (2002).

* cited by examiner

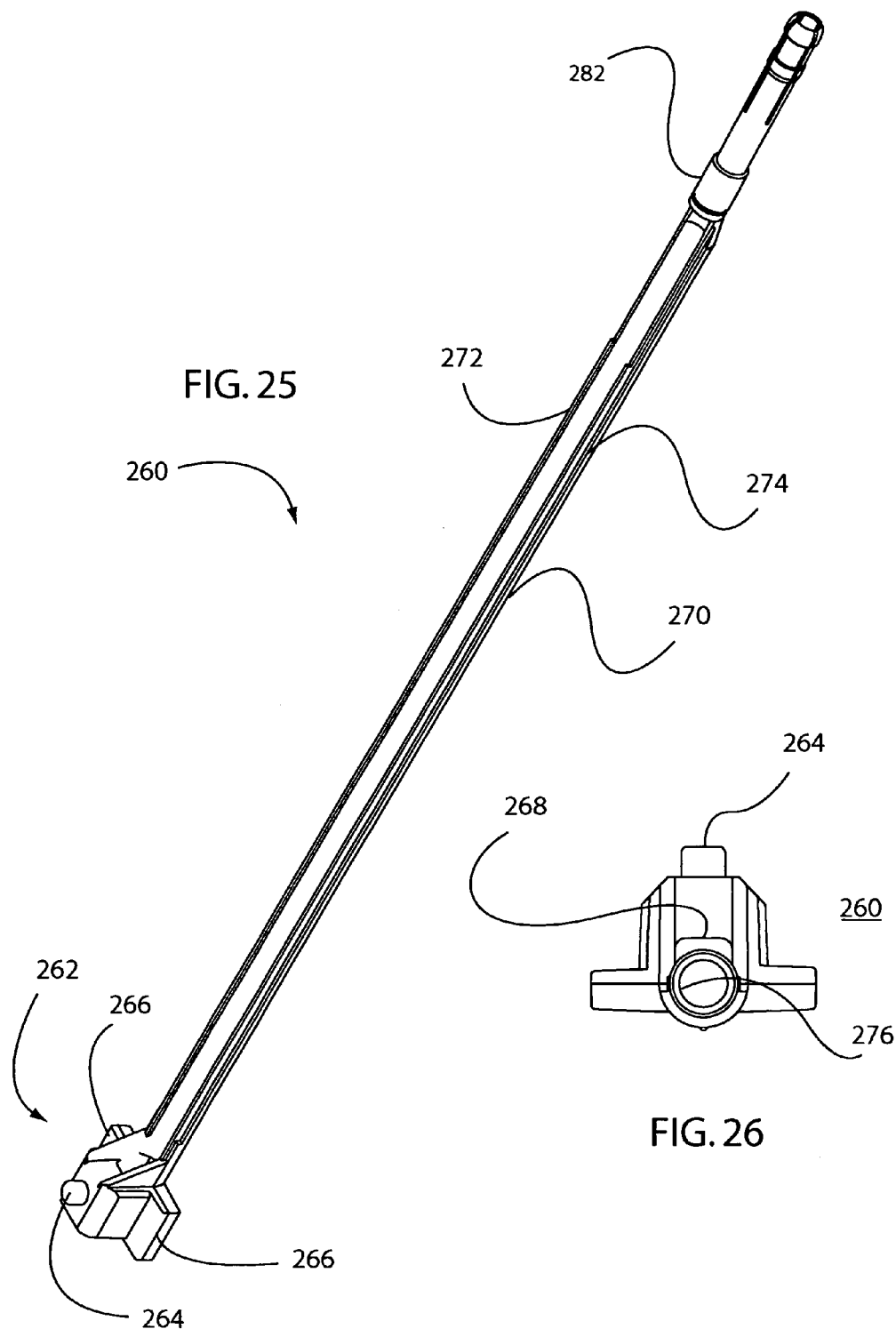

METHOD OF PERFORMING ANASTOMOSIS

This patent application is a divisional of U.S. patent application Ser. No. 10/057,745, filed on Jan. 23, 2002 now U.S. Pat. No. 7,029,482, and is a continuation-in-part of U.S. patent application Ser. No. 10/054,795, filed on Jan. 25, 2002 now U.S. Pat. No. 6,686,427.

FIELD OF THE INVENTION

The present invention relates generally to anastomosis, and more particularly to an anastomosis device and an integrated tool for deploying it.

BACKGROUND

Anastomosis is a procedure where two separate tubular or hollow organs are surgically grafted together to form an intercommunication between them. Vascular anastomosis involves creating an anastomosis between blood vessels to create or restore blood flow. The vascular anastomosis procedure is routinely performed during the treatment of a variety of conditions, including coronary artery disease (CAD), neurovascular disease, diseases of the great and peripheral vessels, organ transplantation, traumatic injury and other vascular abnormalities. When a patient suffers from CAD, an occlusion or stenosis in a coronary artery restricts blood flow to the heart muscle. To treat CAD, the area where the occlusion occurs is bypassed to reroute blood flow by placing a graft vessel (in the form of a harvested artery or vein, prosthesis, allograft or xenograft) between two target vessels: the aorta or other supply of arterial blood, and the coronary artery. Placement of the graft vessel bypasses the blocked coronary artery, circumventing the occlusion and restoring adequate blood flow to the heart muscle. This treatment is known as a coronary artery bypass graft procedure (CABG). A CABG procedure can be performed on a stopped heart, where the patient has been placed on a heart-lung machine, or on a beating heart. Access to the thoracic cavity for a CABG procedure can be provided by sawing the sternum and opening the chest, or by creating one or more small openings in the thoracic cavity. Anastomosis may be performed by hand-suturing the graft vessels together or by utilizing an anastomosis device.

Regardless of the type of CABG procedure that is performed, or the type of anastomosis performed, an opening is made in the aorta or other artery at the proximal anastomosis site to allow blood to flow into the graft vessel. Typically, an incision is made in the aorta with a scalpel. A distal end of an aortic punch is inserted into the incision, then actuated to cut a larger opening in the aorta. While the combination of the scalpel and the aortic punch is commonly used to form an opening in the aorta, there are drawbacks. This is a problematic approach that does not provide reliable hemostasis during beating heart surgery, and has the potential to allow the location of the incision to become lost. Further, after the aortic punch creates an opening in the aorta, blood will flow out of that opening. Further, the aortic punch is just one tool of a multiple-tool system for creating an opening in the aorta. At least one additional tool is needed for attaching a graft vessel to a target vessel. The use of multiple tools adds steps, time and complexity to the CABG procedure.

SUMMARY

In one aspect of the invention, an anastomosis device for connecting a graft vessel to a target vessel has a deployable section detachably connected to a discard section. The discard section includes one or more paddles for connection to an application tool and may include a compression segment. The deployable section includes tines connected to a linkage, which in turn is connected to a plurality of outer flange elements.

In another aspect of the invention, the deployable section of the anastomosis device is configured to deform such that the tines form an inner flange, the outer flange elements form an outer flange, and the linkage partially expands to form a body linking the inner flange to the outer flange.

In another aspect of the invention, an integrated anastomosis tool includes a first mechanism for creating an opening in the wall of a target vessel, and a second mechanism for deploying an anastomosis device into that opening.

In another aspect of the invention, the discard section of the anastomosis device is connected to the integrated anastomosis tool.

In another aspect of the invention, the integrated anastomosis tool includes a single control for accepting user input associated with creating an opening in the vessel wall and completing an anastomosis between a graft vessel and a target vessel.

In another aspect of the invention, deployment of the anastomosis device from the integrated anastomosis tool is controlled by one or more cam paths. One or more cam followers on the mechanism for deploying the anastomosis device engage one or more cam paths. The cam paths may be defined on a cam cylinder.

In another aspect of the invention, the components of the integrated anastomosis tool are located outside of the lumen of the graft vessel. In this way, the inner surface of the graft vessel is protected against damage by the integrated anastomosis tool.

In another aspect of the invention, a cartridge is detachably connected to the integrated anastomosis tool. A crown and an expander are configured to translate relative to the cartridge, guided along at least one groove, cam path and/or other structure.

In another aspect of the invention, the discard section of the anastomosis device is connected to the distal end of the crown. The graft vessel extends through the center of the crown and expander, and is everted over the anastomosis device at the distal end of the crown.

In another aspect of the invention, the expander includes an expander tip at its distal end. A number of slots extend substantially axially through the expander tip, and the segments of the expander tip between the slots may be biased away from the axis of the expander tip.

In another aspect of the invention, the angular spacing between an expander slot and a first adjacent expander slot is different from the angular spacing between that expander slot and a second adjacent expander slot. In this way, the expander tip is stiffer along some cross-sections than others.

In another aspect of the invention, relative motion between the crown and the expander deforms the anastomosis device and deploys the deployable section into an opening in the target vessel.

In another aspect of the invention, the expander tip includes a collet that is colleted down by the crown to move the segments of the expander tip inward and allow the expander tip to move proximally relative to the deployed anastomosis device.

In another aspect of the invention, the outer flange elements include gripping elements for gripping the outer surface of the target vessel.

In another aspect of the invention, at least part of the integrated anastomosis tool is lubricated with a biocompatible lubricant such as sodium stearate.

BRIEF DESCRIPTION OF THE DRAWINGS

FIG. 25 is a perspective view of an expander.

FIG. 26 is an end view of the distal end of the expander of FIG. 25, with the expander tip removed.

The use of the same reference symbols in different figures indicates similar or identical items.

DETAILED DESCRIPTION

Figure 1:
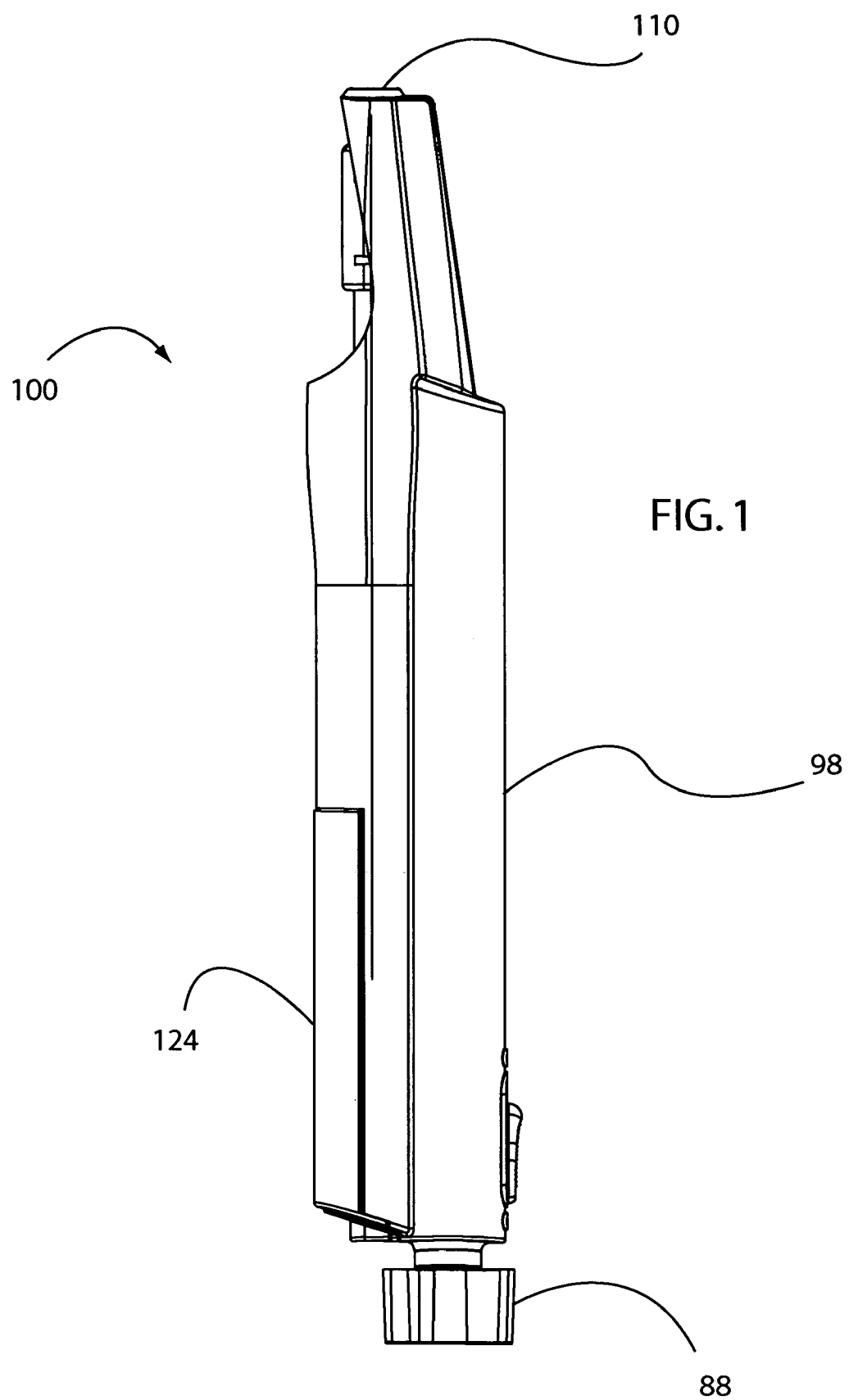
FIG. 1 is a side view of an integrated anastomosis tool.
Figure 14:
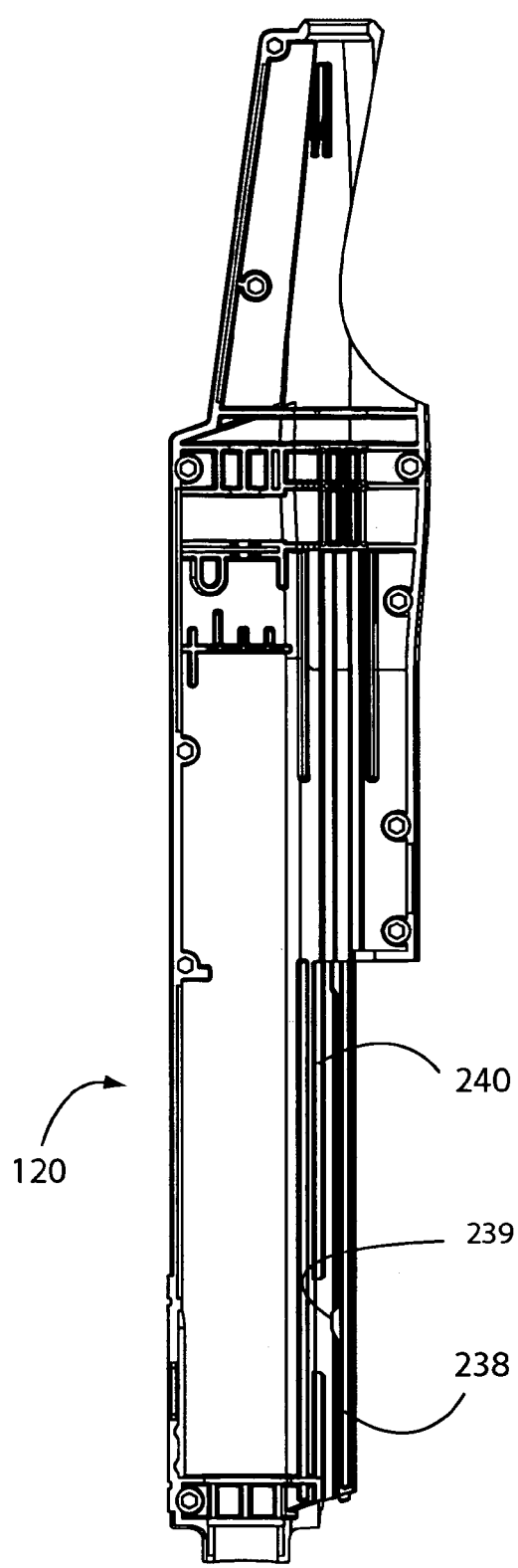
FIG. 14 is a side view of a first case half.
Figure 15:
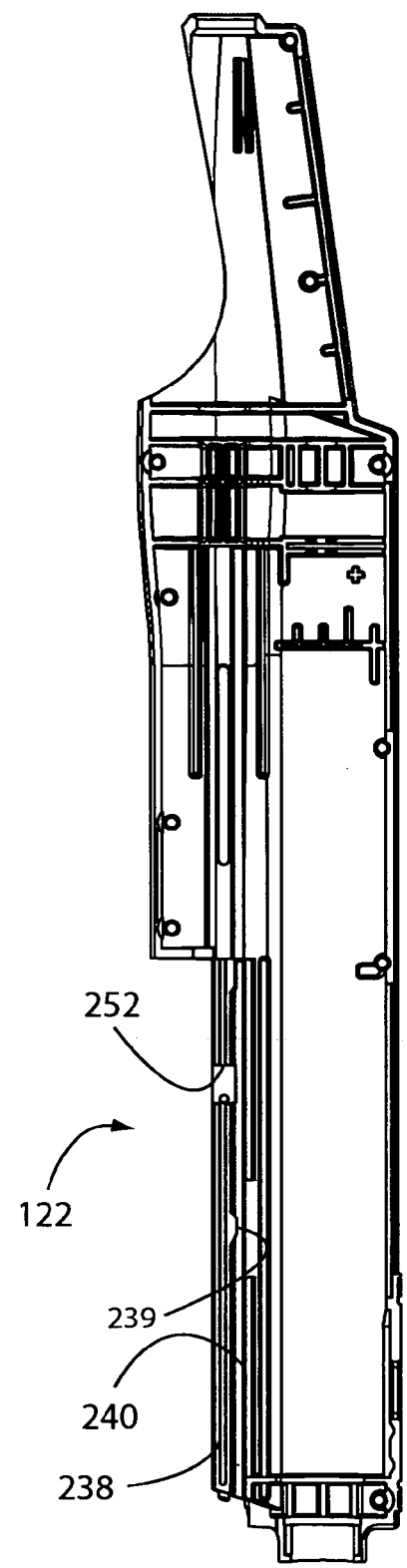
FIG. 15 is a side view of a second case half configured to mate with the first case half of FIG. 14.

Referring to FIG. 1, an integrated anastomosis tool 100 is shown. A casing 98 defines the outer surface of the integrated anastomosis tool 100. Referring also to FIGS. 14-15, the casing 98 is formed by connecting a first case half 120 and a second case half 122. The case halves 120, 122 may be connected by screws, bolts, adhesives, or other structures, mechanisms or methods. Alternately, the casing 98 may be unitary, or may be formed from more than two individual casing components. The casing 98 is composed of plastic or other biocompatible material, and may be constructed by vacuum molding, injection molding, or any other method appropriate for the material utilized. A contact structure 110 is located at the distal end of the casing 98, and is configured for placement against a vessel wall or other bodily structure. A cartridge 124 is inserted into the casing 98 before the integrated anastomosis tool is operated. The cartridge 124 is described in greater detail below. The casing 98 provides a shell within which other components of the integrated anastomosis tool 100 are located. These components include an assembly for creating an opening in a vessel wall, and an assembly for placing and deploying an anastomotic device into that opening.

Referring to FIGS. 1A-3, a cutter 4 is connected to an auger 6. The cutter 4 is constructed from a biocompatible metal, such as stainless steel, but a different biocompatible material may be used if desired. The distal end of the cutter 4 is sharpened to cut the wall of a tubular vessel, such as the aorta or other blood vessel. The cutter 4 is a hollow tubular structure with an open distal end. The distal end of the cutter 4 has a substantially circular shape, and the cutter 4 has a substantially circular cross-section along its length. However, the cutter 4 may take another shape, have a different cross section, or vary in cross section along its length. For example, the cutter 4 may take the shape of a tube having an open slit along its length. That is, the cutter 4 may form of the majority of a cylindrical surface, where the cutter 4 extends along, for example, 350° of the complete 360° perimeter of the cylinder. The cutter 4 has an inner surface 12 and an outer surface 8. The distal end of the cutter 4 is beveled for sharpness. The distal end of the cutter 4 may be beveled inward, such that the inner surface 12 contacts a vessel wall before the outer surface 8, or beveled outward, such that the inner surface 12 contacts a vessel wall after the outer surface 8. Alternately, the distal end of the cutter 4 may be beveled both inward and outward, such that a sharp edge is provided at a location between the inner surface 12 and outer surface 8 of the cutter 4.

Figure 3:
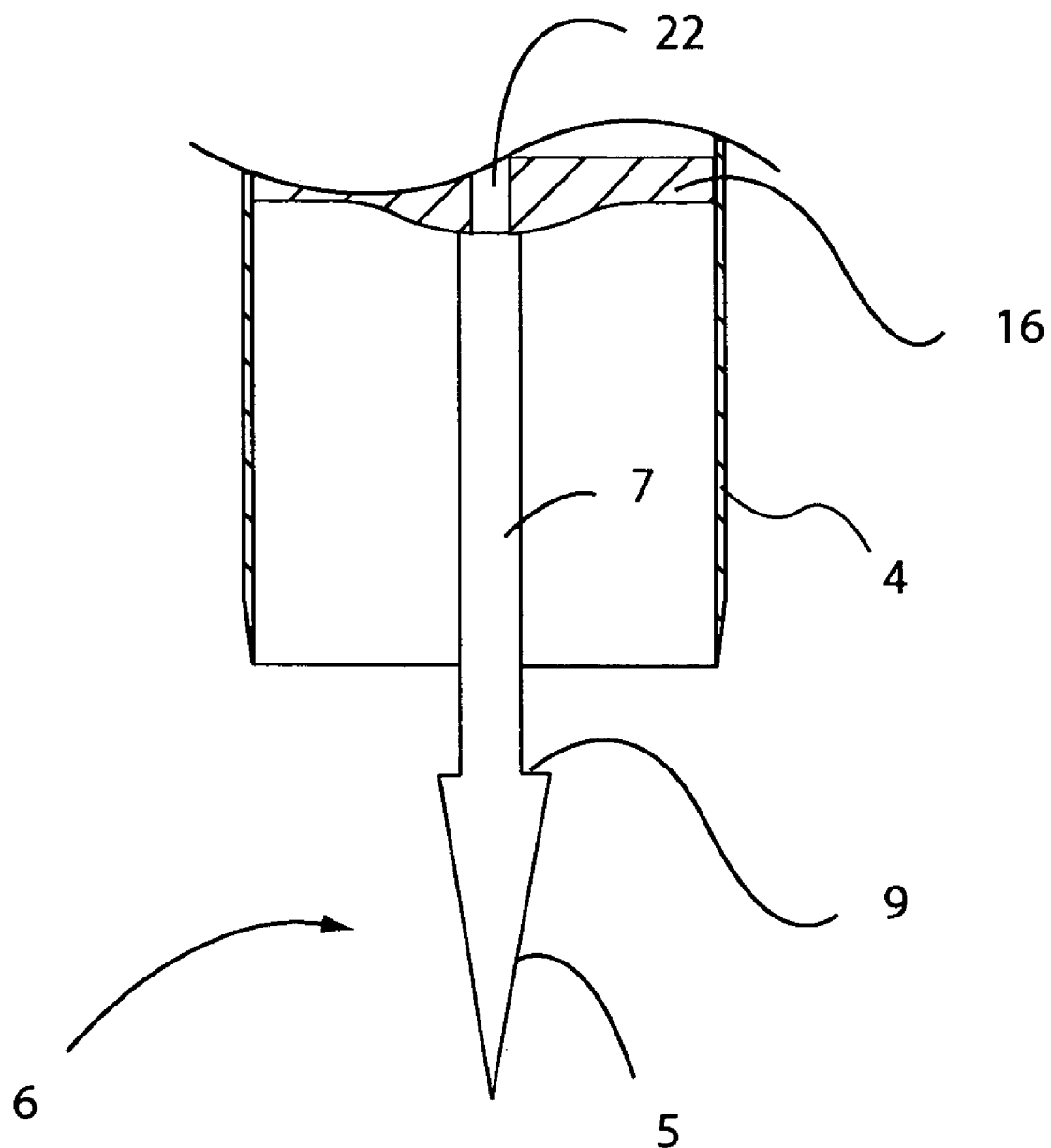
FIG. 3 is a cross-section detail view of an auger and cutter forming part of the assembly of FIGS. 1 and 2.

The auger assembly 10 is fixed to the cutter 4, and extends through its hollow center. In one embodiment, the auger assembly 10 extends through at least part of the hollow center of the cutter 4, and extends to a location proximal to the proximal end of the cutter 4. The auger assembly 10 is constructed from the same biocompatible metal as the cutter 4. Alternately, the auger assembly 10 may be constructed from a different biocompatible material. The auger assembly 10 may include a number of components. The auger 6 is one of these components, located at the distal end of the auger assembly 10. The auger 6 may be an integral part of the auger assembly 10, or instead may be a separate component that is connected to another portion of the auger assembly 10. Referring particularly to FIG. 3, the auger 6 is substantially coaxial with the cutter 4. The auger 6 includes a spike 5 at its distal end, and a shaft 7 extending proximally from the spike 5. The shaft 7 is substantially cylindrical. Alternately, the shaft 7 may be shaped differently. The spike 5 is tapered from its proximal end toward its distal end, and is substantially radially symmetrical. The distal end of the spike 5 is sharp to allow it to readily penetrate tissue, as described in greater detail below. The proximal end of the spike 5 is wider than the shaft 7, such that a ledge 9 is formed at the proximal end of the spike 5. The distal end of the spike 5 extends distal to the distal end of the cutter 4. Further, the spike 5 is positioned relative to the cutter 4 and is shaped such that the ledge 9 extends distally at least as far as the distal end of the cutter 4.

Alternately, the auger 6 and the cutter 4 are configured as described above, but are fixed to one another only axially; they are free to rotate with respect to one another. That is, the auger 6 and cutter 4 are configured to translate together at the same rate in the axial direction, but are free to rotate independently of one another. For example, the auger 6 may include a circumferential flange (not shown) held within a corresponding groove (not shown) in the cutter 4. The flange can rotate within the groove, and contact between the flange and the groove causes the auger 6 and cutter 4 to translate together. That is, the auger 6 and the cutter 4 are fixed axially, but independent rotationally. While the auger 6 and the cutter 4 are capable of rotating relative to one another, they need not do so, and may rotate together at the same rate if desired. Other mechanisms or structures may be used to configure the auger 6 and the cutter 4 to translate together axially while having the capability of rotating independently.

Figure 4:
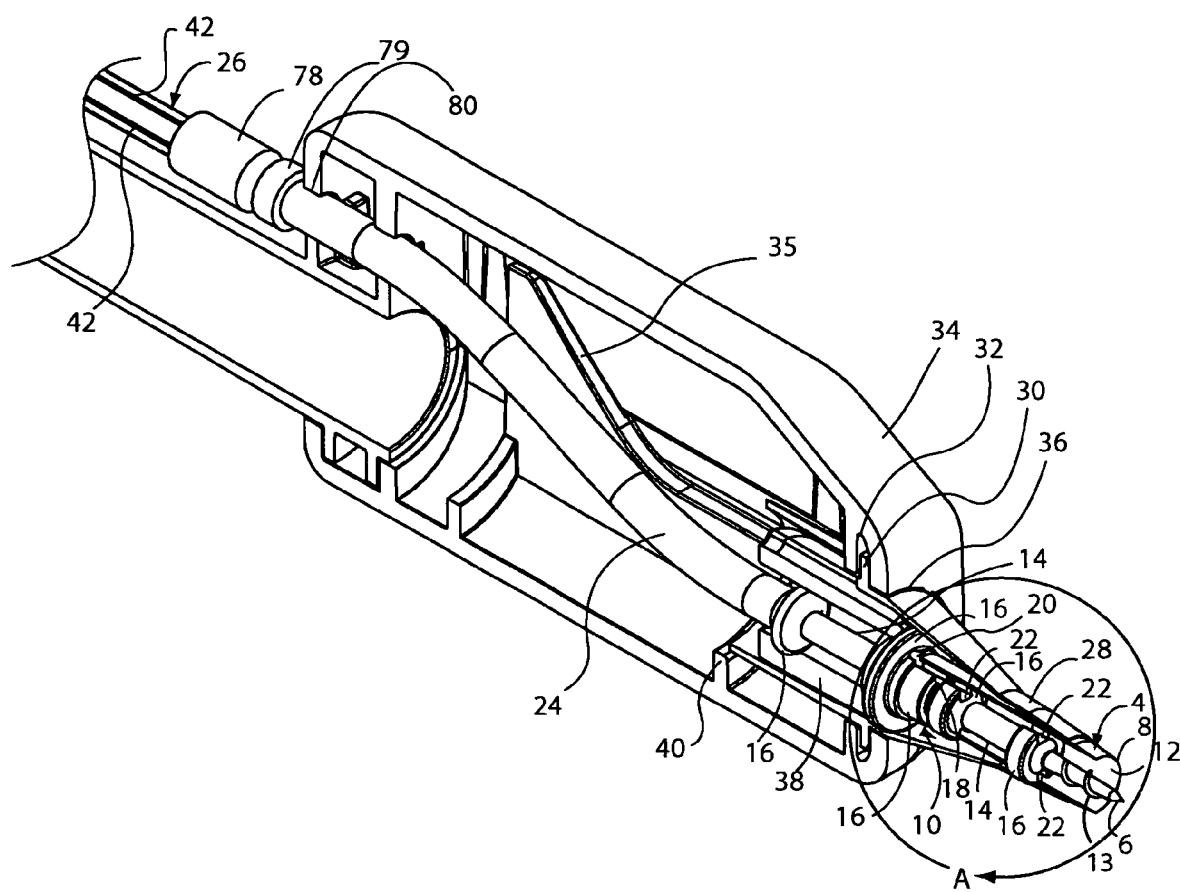
FIG. 4 is a cutaway view of the distal end of another embodiment of assembly for creating an opening in the wall of a tubular vessel.
Figure 5:
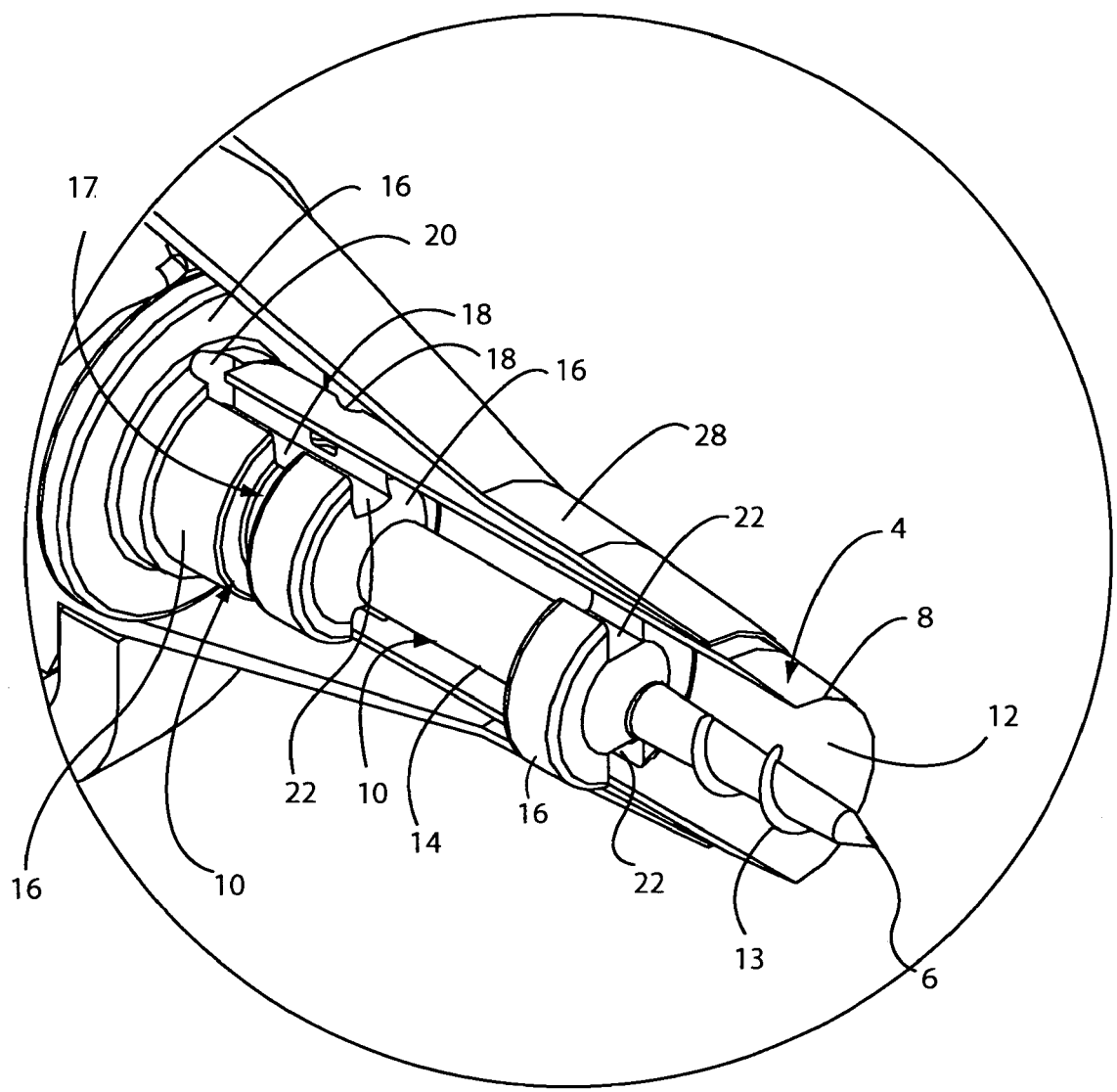
FIG. 5 is a detail view of the distal end of the assembly of FIG. 4.

Referring to FIGS. 4-5, another embodiment of the auger 6 is shown. The auger 6 has one or more flutes 13 defined on its outer surface. The flutes 13 have a pitch of substantially 16 threads per inch and a thread angle of substantially thirty-seven degrees. Alternately, a different pitch and/or thread angle may be used. In one embodiment, the auger 6 is tapered from its proximal end toward its distal end. The distal end of the auger 6 is sharp, to facilitate its entry into the wall of the tubular vessel, and extends to a location that is further in the distal direction than the distal end of the cutter 4. Alternately, a piercing member other than the auger 6 is axially fixed to the cutter 4, such as a barb, harpoon, lance, corkscrew or a needle without flutes.

The auger assembly 10 includes a center rod 14 that is connected to the shaft 7 of the auger 6 and that is substantially coaxial with the cutter 4 and with the auger 6. Alternately, the center rod 14 may be positioned along a different axis. The shaft 7 may be formed as an integral part of the center rod 14. One or more centering flanges 16 are fixed to the center rod 14, extending outward radially from the center rod 14 to contact the cutter 4. One or more of the centering flanges 16 may be fixed to the cutter 4. The centering flanges 16 are utilized to position the center rod 14 within the cutter 4 along at a desired axis and to provide support and stiffness to the cutter 4. As described above, the centering flanges 16 may be utilized to center the center rod 14 within the cutter 4. In one embodiment, the centering flanges 16 are constructed as part of the center rod 14, thereby forming a unitary structure. However, the centering flanges 16 may be constructed separately from the center rod 14, then connected to the center rod 14, such as by adhesive or other fastening mechanism, structure or method. One or more centering flanges 16 may also be formed into or attached to the portion of the center rod 14 that extends proximal to the cutter 4. These centering flanges 16 may be utilized to position the center rod 14 relative to one or more other structures or mechanisms and/or to provide bearing surfaces for rotation of the auger assembly 10. The centering flanges 16 may have different thicknesses in the axial direction.

The cutter 4 is attached to the auger assembly 10 by dimpling the cutter 4 in one or more locations. One of the centering flanges 16 includes a groove 17 defined substantially circumferentially around it. The centering flange 16 that includes the groove 17 may be wider than one or more other centering flanges 16. Each dimple 18 is located within the groove 17. Each dimple 18 is formed by pressing the cutter 4 inward toward the groove 17, causing that location on the cutter 4 to deform into a dimple 18. The dimple 18 expands into a portion of the groove 17, trapping the dimple 18 therein. The cutter 4 thus is fixed to the auger assembly 10, such that they rotate and translate together. Alternately, the cutter 4 includes one or more partially-circumferential ribs (not shown) extending inward from its inner surface 12. Each rib is crimped between two centering flanges 16, and is thereby trapped between them and fixed to them to fix the cutter 4 to the auger assembly 10. The auger assembly 10 may be connected to the cutter 4 using other or additional suitable mechanisms, structures or methods. Such a connection may be used where the auger 6 is fixed axially to, but free to rotate relative to, the cutter 4. For example, the auger assembly 10 and the cutter 4 may be molded or otherwise formed together as a single piece. As another example, the auger assembly 10 and the cutter 4 may be fixed together by adhesive. As another example, the auger assembly 10 and the cutter 4 may be fixed together by welding, or may be pinned or screwed together.

At least one vent 20 is defined in the auger assembly 10 at or proximal to the proximal end of the cutter 4. The vent 20 connects a space inside the cutter 4 with a space outside the cutter 4. Similarly, at least one slot 22 is defined through each centering flange 16. If a centering flange 16 is located adjacent to the proximal end of the cutter 4, the slot 22 in that centering flange 16 is aligned with the vent 20. The vent 20, in combination with the at least one slot 22 in each centering flange 16, provides a pathway for fluid such as air or blood to escape from the cutter 4 when the cutter 4 and auger 6 are deployed into the vessel wall. The cutter 4 is vented to prevent fluid from becoming trapped within the cutter 4, because the pressure of that trapped fluid could potentially prevent the cutter 4 from penetrating the vessel wall or other anatomical structure. Other structures or mechanisms than the vent 20 and the slot 22 may be used to vent the cutter 4.

An actuator 24 is connected to the proximal end of the auger assembly 10. The center rod 14 extends to the proximal end of the auger assembly 10, and the actuator 24 connects to the center rod 14. Advantageously, the actuator 24 is a coil spring that is tightly wound, and the center rod 14 is threaded into the distal end of the spring. Alternately, the spring may be connected to the center rod 14 by adhesive, welding, soldering, compressive force or other methods or mechanisms. In this way, the spring provides flexibility and transmits translational and rotational force to the auger assembly 10. However, the actuator 24 may be any other structure or mechanism that is capable of transmitting translational and rotational forces to the auger assembly 10. Additionally, the actuator 24 need not be flexible if the auger 6 and cutter 4 are not moved off-axis, as is described in greater detail below. The actuator 24 is connected at its proximal end to the distal end of a first driveshaft 26.

At least a portion of the auger assembly 10 and the cutter 4 is positioned within a hollow introducer tip 28. The introducer tip 28 is a tapered element that is narrower at its distal end than at its proximal end. Alternately, the introducer tip 28 is not tapered. The introducer tip 28 has a substantially circular cross-section along its length. The introducer tip 28 is a radially and bilaterally symmetrical shell. Alternately, the introducer tip 28 can take a different shape, symmetry or form. The introducer tip 28 is composed of a biocompatible plastic, although a different material or combination of materials may be used. The inner diameter of the distal end of the introducer tip 28 is substantially the same as the outer diameter of the cutter 4, as measured at the distal end of the introducer tip 28. Further, the introducer tip 28 is substantially coaxial with the cutter 4. Thus, at the distal end of the introducer tip 28, the cutter 4 substantially seals against the introducer. As with the distal end of the cutter 4, the distal end of the introducer tip 28 may be beveled inward. Initially, the cutter 4 extends distally from the distal end of the introducer tip 28, and the distal end of the introducer tip 28 follows the cutter 4 into an opening cut in the wall of a tubular vessel, as is described in greater detail below. The introducer tip 28 may be splittable or expandable, if desired, such that the diameter of its distal end can be enlarged. Such enlargement may be useful in translating an anastomotic device through the introducer tip 28, or for other purposes.

The introducer tip 28 includes a circumferential flange 30 at or near its proximal end, where that flange 30 is held within a circumferential slot 32 in a seal housing 34 at or near its distal end. The introducer tip 28 thereby is secured to the seal housing 34. Alternately, the flange 30 is not circumferential, and the slot 32 in the seal housing 34 is correspondingly not circumferential. Alternately, the introducer tip 28 is secured to the seal housing 34 by a different structure, mechanism or method, such as by adhesive. The seal housing 34 is a substantially hollow structure into which the proximal end of the auger assembly 10 extends. The seal housing 34 includes an opening 36 at or near its distal end through which the introducer tip 28 and the auger assembly 10 extend. The cutter 4 extends proximally through the opening 36 in the seal housing 34. Alternately, the cutter 4 does not extend as far proximally as the opening 36 in the seal housing 34. The actuator 24 extends through the seal housing 34, and may extend out of an opening 80 at or near the proximal end of the seal housing 34. Alternately, the actuator 24 does not extend out of the seal housing.

The proximal end of the auger assembly 10 extends through the interior of a bushing 38. The bushing 38 is substantially cylindrical and has a substantially cylindrical opening therethrough. However, the bushing 38 and/or the opening through it may be shaped differently. The distal end of the bushing 38 contacts at least one centering flange 16 that is connected to the center rod 14. The distal end of the bushing 38 may be free to translate relative to that centering flange 16, where that centering flange 16 has a diameter larger than the passage through the bushing 38 such that the bushing 38 cannot advance distally past that centering flange 16. Alternately, the distal end of the bushing 38 contacts the inner surface of the introducer tip 28 instead of or in addition to at least one centering flange 16. The bushing 38 is restrained from rotation as the cutter 4 and auger assembly 10 rotate due to contact with at least one centering flange 16 and/or the introducer tip 28. However, registration features, stops or other structures or mechanisms may be used to restrain the bushing 38 from rotation. The bushing 38 may be tapered, such that the distal end of the bushing 38 contacts at least one centering flange 16, and another, wider location on the bushing 38 near the distal end of the bushing 38 contacts the inner surface of the introducer tip 28. The bushing 38 is supported by the introducer tip 28. The proximal end of the bushing 38 may contact a rib 40 or other structure within the seal housing 34. However, the proximal end of the bushing 38 is not fixed to the rib 40 or similar structure. Thus, the bushing 38 is free to translate proximally with respect to the introducer tip 28, but is restrained in its forward motion by contact with at least one centering flange 16 and/or introducer tip 28. One or more centering flanges 16 may be located within the bushing 38, and each centering flange 16 is connected to the center rod 14. However, the centering flanges 16 within the bushing 38 are free to rotate relative to the bushing 38. Thus, the auger assembly 10 may rotate relative to the bushing 38, and is supported and guided by the bushing 38 during this rotation.

A guide 35 is defined in or connected to the inner surface of the seal housing 34. The guide 35 may be a ramp, slot or other structure or mechanism. Advantageously, two guides 35 are provided, one on the inner surface of each side of the seal housing 34. For clarity, only one side of the seal housing 34 is shown. Because the seal housing 34 is substantially symmetrical, the guide 35 on the side of the seal housing 34 that is not shown is substantially symmetrical with the guide 35 shown. A guide follower (not shown) extends from the bushing 38 to contact or otherwise engage the corresponding guide 35. One guide follower is associated with each guide 35. The guides 35 are configured to guide the bushing 38, and with it the auger 6, cutter 4 and captured tissue away from the axis of the introducer tip 28 to a second axis spaced apart from the introducer axis, as is described in greater detail below. Thus, the location and orientation of the guides 35 on the inner surface of the seal housing 34 is dependent upon the location of the second axis.

Figures 6, 7:
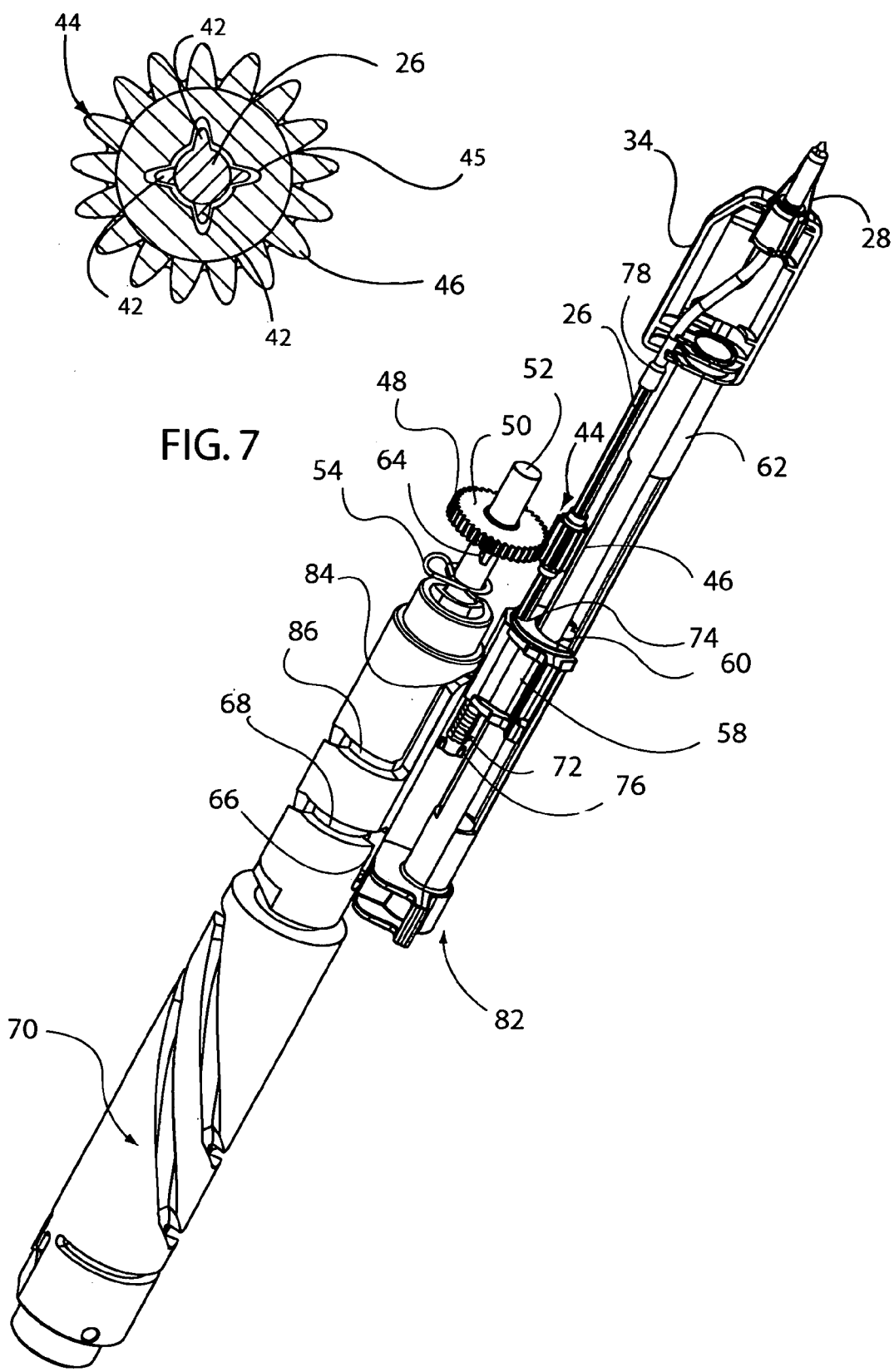
FIG. 6 is a perspective view of a drive mechanism for use with the assembly for creating an opening in the wall of a tubular vessel.
FIG. 7 is an end cross-section view of a first gear and a first driveshaft forming part of the drive mechanism of FIG. 6.

The auger assembly 10 and the cutter 4 can be actuated to rotate and to translate forward in any one of a number of ways. Referring also to FIG. 6, the distal end of a first driveshaft 26 is connected to the proximal end of the actuator 24. The connection between the first driveshaft 26 and the actuator 24 may be made inside or outside the seal housing 34. The first driveshaft 26 is substantially rigid, and has a number of ribs 42 aligned substantially axially along its surface, extending substantially radially outward. Alternately, the ribs 42 are aligned and/or extend differently. Four ribs 42 are spaced evenly around the circumference of the first driveshaft 26, but more or fewer ribs 42 may be utilized. The first driveshaft 26 is capable of axial translation relative to a first gear 44 that is substantially coaxial with the first driveshaft 26. The first gear 44 is mounted to a casing (not shown) or other structure, such that it is free to rotate about its axis but fixed in the axial direction and restrained against axial translation. Such mounting is standard in the art. The first gear 44 has a passage 45 therethrough, wherein a number of ribs (not shown) extend inward toward the rod 24 and are positioned between the ribs 42 on the first driveshaft 26. Contact between the ribs 42 and at least a portion of the surface of the passage 45 allows the first driveshaft 26 to translate axially relative to the first gear 44. Alternately, the first gear 44 and the first driveshaft 26 may be configured differently to allow rotary motion to be transmitted between the first driveshaft 26 and the first gear 44 while additionally allowing the first driveshaft 26 to translate axially relative to the first gear 44.

Figure 8:
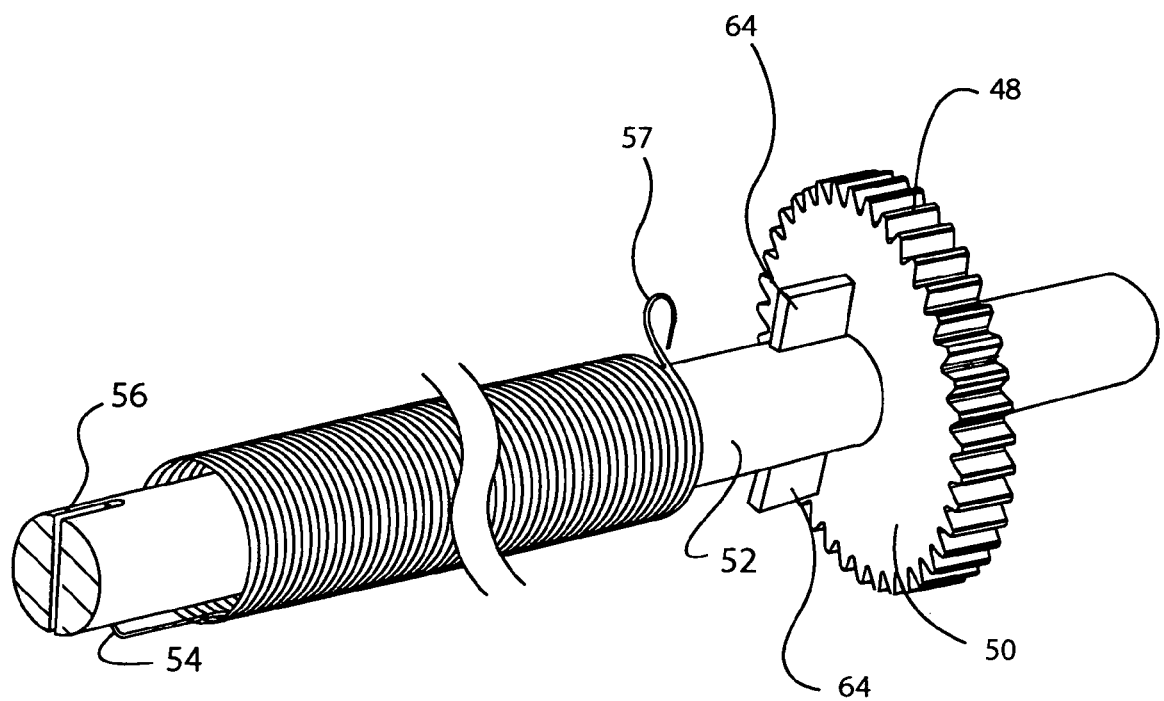
FIG. 8 is a perspective view of a second driveshaft forming part of the drive mechanism of FIG. 6.

Referring also to FIGS. 6-8, the first gear 44 has a number of teeth 46 aligned in a substantially axial direction and extending outward substantially radially. These teeth 46 interface with teeth 48 of a second gear 50, which correspondingly extend in a substantially axial direction. The second gear 50 has a diameter larger than that of the first gear 44, such that the gear ratio between the second gear 50 and the first gear 44 is larger than 1:1. Advantageously, the gear ratio is substantially 39:11. A different gear ratio may be used, if desired. The second gear 50 is mounted substantially coaxially to a second driveshaft 52 that is substantially parallel to the first driveshaft 26. Alternately, the second driveshaft 52 may be positioned in another orientation, and the teeth of the gears 44, 50 are constructed to interface at that orientation. Rotation of the second driveshaft 52 at a particular rate causes the first driveshaft 26 to rotate at a faster rate, due to the gear ratio of greater than 1:1 between the second gear 50 and the first gear 44.

The second driveshaft 52 may be driven by any mechanism or method. In one embodiment, the second driveshaft 52 is connected to an impulse source. A force that acts on a body for a short time but produces a large change in its linear or angular momentum is called an impulsive force. As used in this document, the term "impulse source" refers to a source of such an impulsive force. The impulse source is a torsional spring 54. However, the impulse source instead may be a different mechanism. The duration of the force generated by the spring 54 or other impulse source is substantially 0.05 seconds. However, the duration may be shorter or longer. Referring particularly to FIG. 8, the spring 54 surrounds at least a portion of the length of the second driveshaft 52. The proximal end of the spring 54 is fixed to a slot 56 in the second driveshaft 52. FIG. 8 shows a cross-section of the second driveshaft 52 for clarity in illustrating the connection between the spring 54 and the slot 56. The proximal end of the spring 54 is bent to fit into the slot 56, and is stiff enough and extends into the slot 56 far enough such that the contact between the proximal end of the spring 54 and the slot 56 holds the spring 54 in place. Alternately, the proximal end of the spring 54 is fixed to the second driveshaft 52 in another way. The distal end 57 of the spring 54 extends outward from the second driveshaft 52, and is fixed to a casing (not shown) or other structure relative to which the second driveshaft 52 rotates. Before the auger assembly 10 and cutter 4 are actuated, the spring 54 is wound up tightly, thereby storing a quantity of force in a torsioned state.

The impulse source may be different from the spring 54. For example, the impulse source may be a DC motor connected directly or via one or more gears to the second driveshaft 52. As another example, the impulse source may be a flow of biocompatible liquid such as water through an impeller or other mechanism connected to the second driveshaft 52. As another example, the impulse source is a magnetic field source coupled to the second driveshaft 52. A different impulse source than these exemplary ones may be used instead. In another embodiment, the impulse source is not used, and the auger assembly 10 and the cutter 4 are rotated non-impulsively, such as by hand.

One or more registration features 64 extend substantially radially outward from the second driveshaft 52 and/or the second gear 50. Each registration feature 64 is a tab. Alternately, the registration features 64 may be different structures than tabs. Where multiple registration features 64 are used, they are spaced evenly around the axis of the second driveshaft 52, but may be spaced differently if desired. Thus, where two registration features 64 are used, they are located on opposite sides of the second driveshaft 52, such that they fall substantially in the same plane. Alternately, the registration features 64 are not coplanar. If the registration features 64 are connected to the second gear 50, they are short enough such that they do not interfere with the operation of the second gear 50.

The registration features 64 are held by, or held relative to, the casing (not shown) or other structure or mechanism until rotation of the second driveshaft 52 is desired. Any appropriate structure or mechanism may be used to hold the registration features 64 relative to the casing. As one example, each registration feature 64 is positioned in a slot (not shown) defined by raised features on the inner surface of the casing, or against a ridge (not shown) extending inward from the casing toward the second driveshaft 52. The slots, ridges or other structures or mechanisms engage the registration feature or features 64 and restrain the second driveshaft 52 against rotation. Where the impulse source is the spring 54, the spring 54 biases the registration features 64 against the corresponding slots, ridges or other structures used to restrain the registration features 64. The registration features 64 are freed from the corresponding slots, ridges or other structures or mechanisms in order to allow rotation of the second driveshaft 52. For example, a slot holding a registration feature 64 is open at its distal end. Motion of the registration feature 64 distally frees it from the slot, allowing the second driveshaft 52 to rotate under the influence of the impulse source. As another example, a ridge holding a registration feature 64 extends axially. Motion of the registration feature 64 distally moves it beyond the ridge, allowing the second driveshaft 52 to rotate under the influence of the impulse source. Freeing the registration features 64 may be accomplished in a different manner, if desired.

As shown in FIG. 6, the second driveshaft 52 is in an initial position, in which the registration features 64 are restrained by slots, ridges, or other structures or mechanisms (not shown). This position may be referred to as the restrained position. After the second driveshaft 52 advances distally to free the registration features 64, the second driveshaft 52 is in a second position that may be referred to as the deployed position. The second gear 50 is fixed to the second driveshaft 52, such that the second gear 50 advances distally the same distance as the second driveshaft 52. The first gear 44 is at least as long as the distance that the second gear 50 advances, such that the first gear 44 is in mating contact with the second gear 50 throughout the entire distance that the second gear 50 translates.

The registration features 64 described above need not be used if the impulse source does not exert a force against the second driveshaft 52 until rotary motion of the second driveshaft is desired. For example, where the impulse source is a DC motor, the motor may be configured to exert a rotational force on the second driveshaft 52 only when rotary motion of the second driveshaft 52 is desired, and registration features 64 thus need not be provided to restrain the second driveshaft 52 against rotation in the initial position.

Figure 9:
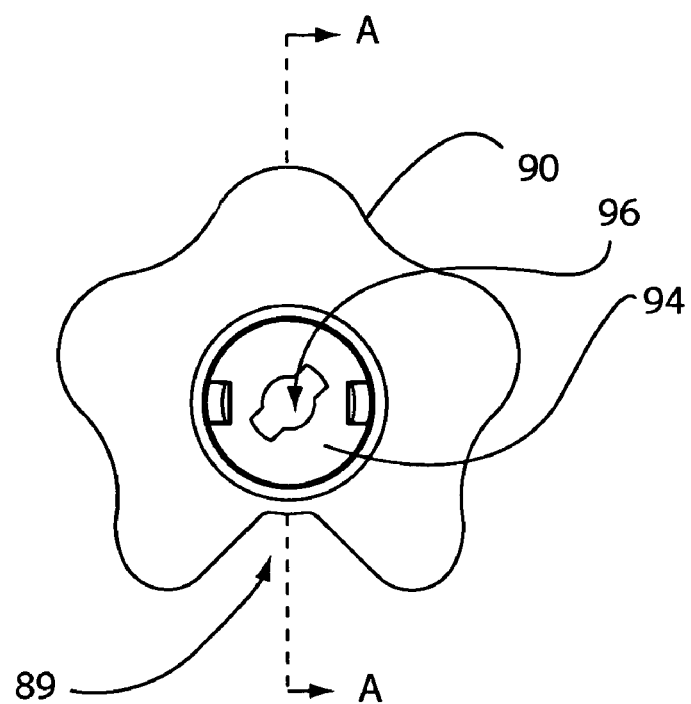
FIG. 9 is an end view of a knob utilized to operate the drive mechanism of FIG. 6.
Figure 10:
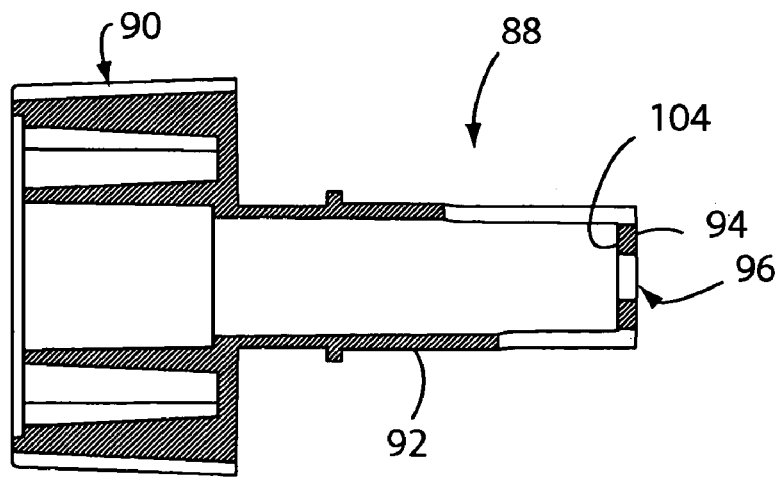
FIG. 10 is a cross-section view of the knob of FIG. 9.
Figure 11:
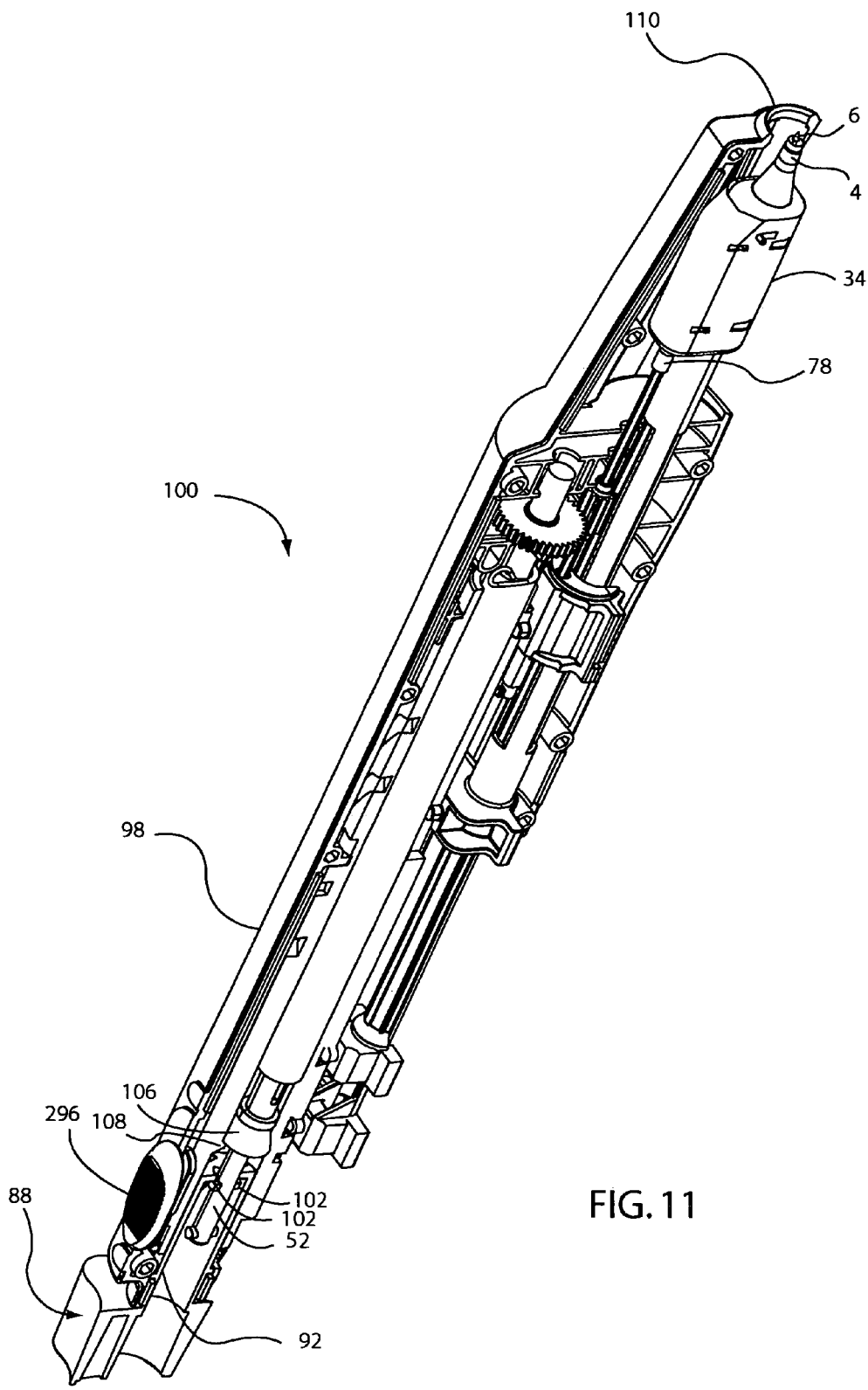
FIG. 11 is a cutaway view of an integrated anastomosis tool, where the tool is in an initial state.

Referring also to FIGS. 9-10, an exemplary embodiment of a knob 88 is shown, where the knob 88 is a component of the integrated anastomosis tool 100. The knob 88 is one embodiment of a device for accepting user input into the integrated anastomosis tool 100. A different structure or mechanism than the knob 88 could be used, if desired The knob 88 includes a grip 90 and a hollow shaft 92. An endplate 94 is connected to the distal end of the shaft 92. The grip 90, shaft 92 and endplate 94 may be formed as a single piece, as by injection molding or another process. A slot 96 extends through the endplate 94. Referring also to FIG. 11, the shaft 92 extends into a casing 98. The casing 98 is substantially hollow, and one or more of the components described above in this document may be located within the casing 98. The casing 98 protects such components and assists in integrating them into a single integrated anastomosis tool 100. The slot 96 is shaped to allow the second driveshaft 52 to extend through it, such that the second driveshaft 52 extends distally into the shaft 92 of the knob 88.

Two stops 102 extend outward from opposite sides the second driveshaft 52. The stops 102 are shaped as substantially rectangular solids. Alternately, one or more stops 102 are shaped differently. Optionally, only one stop 102 may be used, or more than two stops 102 may be used, or the two stops 102 may be arranged differently on the second driveshaft 52. The stops 102 are initially positioned within the shaft 92 of the knob 88. The second driveshaft 52 is in the restrained position, as shown in FIG. 11, before deployment of the auger 6 and cutter 4. In this restrained position, the stops 102 are biased against the proximal surface 104 of the endplate 94, because the second driveshaft 52 is biased distally. A tapered compression spring 106 attached at its narrow end to the second driveshaft 52 performs the biasing, although a different structure or mechanism may be used. The narrow end of the compression spring 106 is positioned distal to the wider end of the compression spring 106. The wider end of the compression spring 106 presses against a circumferential ridge 108 defined on the casing 98. In the initial state, the compression spring 106 is compressed against the ridge 108, resulting in a distal biasing force. The compression spring 106 may be composed of rubber or a similar flexible substance. However, a different material may be used instead. The biasing force exerted by the compression spring 106 biases the stops 102 against the proximal surface 104 of the endplate 94 of the knob 88. The stops 102 are oriented such that they are not aligned with the slot 96 in the endplate 106, such that the second driveshaft 52 cannot pass through the slot 96 and thus is restrained against distal motion. Other structures or mechanisms than the compression spring 106 may be used to bias the second driveshaft 52, such as a coil spring or leaf spring.

Figure 12:
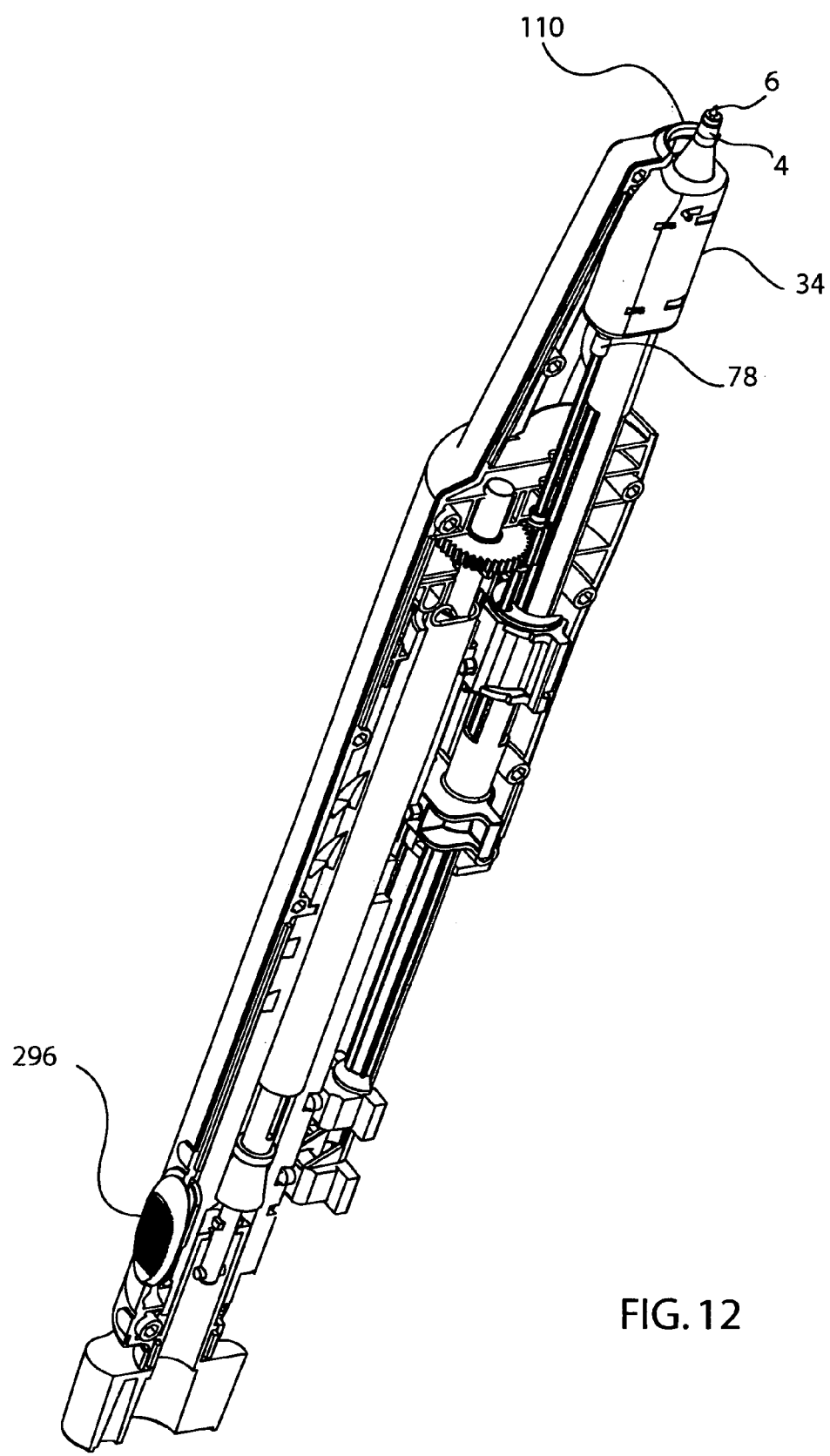
FIG. 12 is a cutaway view of the tool of FIG. 11 in a deployed state.

FIG. 12 shows the second driveshaft 52 in the deployed position, after deployment of the auger 6 and the cutter 4. The knob 88 has rotated, allowing the stops 102 to align with the slot 96 and slide through the slot 96 under the biasing influence of the compression spring 106. The compression spring 106 has moved to a less compressed state. The compression spring 106 may still exert a biasing force distally, but the distal end of the second driveshaft 52, the second gear 50, or another structure or mechanism contacts the casing 98 or another structure and prevents additional forward motion of the second driveshaft 52. The details of the motion of the second driveshaft 52 during operation are described in greater detail below.

Figure 41:
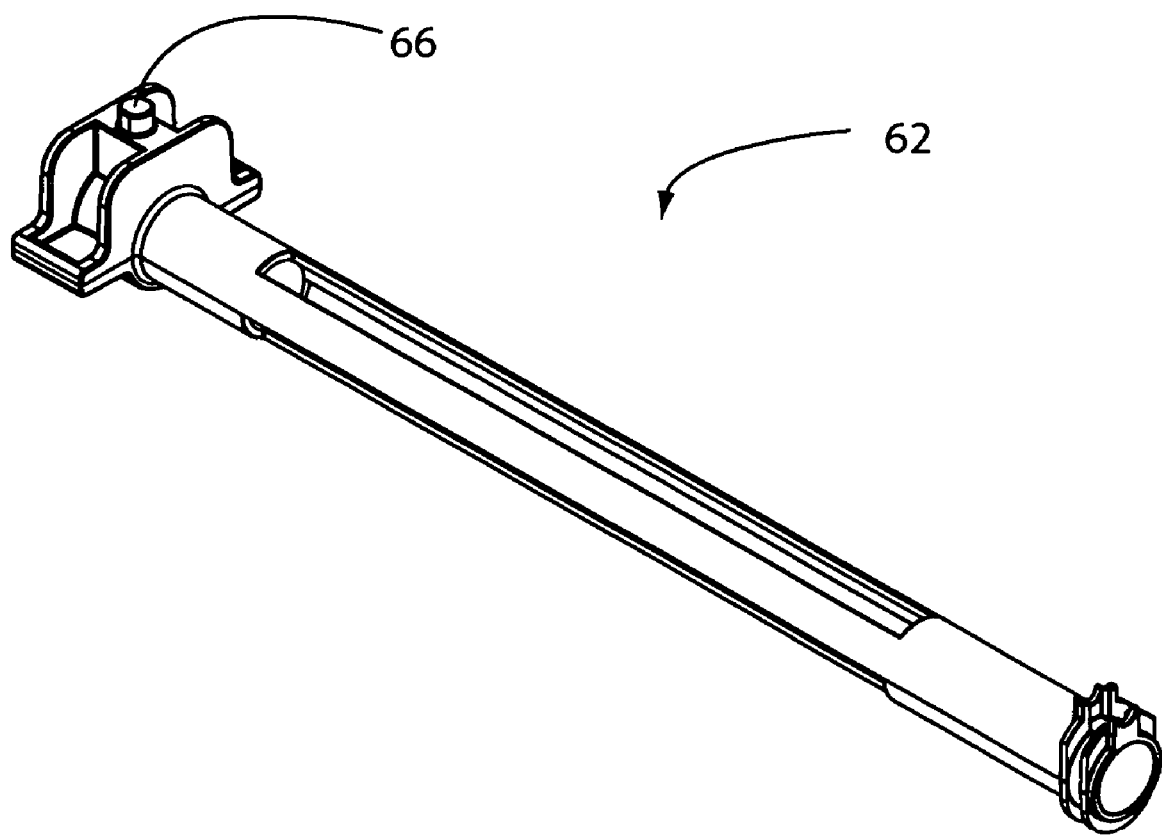
FIG. 41 is a perspective view of the introducer tube.

Referring back to FIG. 6, the first driveshaft 26 is mounted to a carriage 58. Referring also to FIG. 41, the carriage 58 includes a concave surface 60 on its underside, where that concave surface 60 contacts an introducer tube 62. The introducer tube 62 is a hollow tube fixed to the seal housing 34, having a lumen that opens into the interior of the seal housing 34. That lumen may be substantially coaxial with the axis of the introducer tip 28. Alternately, the lumen of the introducer tube 62 may have an axis parallel to but not coaxial with, or not parallel to, the axis of the introducer tip 28. An anastomosis device (not shown) and graft vessel (not shown) may be advanced through the lumen of the introducer tube 62, such that the anastomosis device can connect the vein graft to a target vessel after the auger 6 and cutter 4 have removed a tissue plug from the wall of the target vessel and created an opening therein. Where the anastomosis is performed as part of a CABG procedure, the target vessel is a coronary artery, and the graft vessel is a blood vessel such as the saphenous vein. However, the anastomosis may be performed between two other anatomical structures.

The first driveshaft 26 includes a threaded portion 72 at or near the proximal end of the first driveshaft 26. Alternately, the threaded portion 72 of the first driveshaft 26 is located at another position on the first driveshaft 26. A passage 74 through the carriage 58 is correspondingly threaded to engage the threaded portion 72 of the first driveshaft 26. The threaded portion 72 of the first driveshaft 26 is configured to advance distally as the first driveshaft 26 rotates. Thus, rotary motion of the first driveshaft 26 is used to advance the first driveshaft 26, such that rotation of the second gear 50 is converted to both rotation and translation of the first driveshaft 26. Thus, the threaded portion 72 of the first driveshaft 26 is at least as long as the distance the first driveshaft 26 is to advance, and the corresponding threaded portion of the passage 74 through the carriage 58 can be any length that is capable of adequately supporting the first driveshaft 26 during its advancement. Alternately, the threaded portion 72 of the first driveshaft 26 is shorter than the distance the first driveshaft 26 is to advance, and the threaded portion of the passage 74 through the carriage 58 is at least as long as the distance the first driveshaft 26 is to advance. The threads of the threaded portion 72 of the first driveshaft 26 have a pitch of substantially 25 threads per inch. A different pitch may be utilized, if desired.

The first driveshaft 26 includes a head 76 at or near its proximal end. Alternately, the head 76 is located at a different position on the first driveshaft 26. The head 76 is a structure that is wider than the passage 74 through the carriage 58, such that contact between the head 76 and the carriage 58 stops the distal advancement of the first driveshaft 26. Thus, the head 76 limits the distal travel of the first driveshaft 26. Contact between the head 76 and the carriage 58 provides a positive stop after a particular amount of distal travel of the first driveshaft 26.

Alternately, the first driveshaft 26 does not include a threaded portion 72, and rotation of the second gear 50 causes the first driveshaft 26 to rotate but does not advance the first driveshaft 26 distally. In such an embodiment, a second impulse source (not shown) may be provided, and connected to the carriage 58 or first driveshaft 26 to advance the first driveshaft 26 substantially axially. The second impulse source may be a spring or other mechanism for storing energy and releasing it over a short interval of time. The second impulse source is coordinated with the first impulse source, such as the spring 54, such that both impulse sources produce an impulse at substantially the same time in order to produce rotational and translational motion of the auger assembly 10 and the cutter 4. The timing, advancement and retraction of the auger assembly 10 and the cutter 4 can be controlled in a number of ways. A cam cylinder 70 is used to control the advancement of the auger assembly 10 and the cutter 4. Referring also to FIGS. 38A-D, the surface of the cam cylinder 70 is shown, along with a number of cam paths defined therein. The cam paths are described in greater detail below. The knob 88 or other control structure is directly connected to and substantially coaxial with the cam cylinder 70, such that rotation of the knob 88 rotates the cam cylinder 70. The knob 88 instead may be operationally connected to the cam cylinder 70 via gearing or other mechanisms, such that the knob 88 and cam cylinder 70 can be oriented along different axes. Referring to FIG. 11, a first cam follower 66 extends from the introducer tube 62 into a first cam path 68 defined in the cam cylinder 70. The introducer tube 62 is restrained by the casing 98 and/or other structure or mechanism such that its motion is substantially linear along its axis. Consequently, the first cam follower 66 is restrained to move substantially linearly in a direction substantially parallel to the axis of the introducer tube 62. Rotation of the cam cylinder 70 causes the first cam path 68 to move relative to the first cam follower 66. The first cam follower 66 follows the first cam path 68, and thus can be caused to translate axially or be held stationary as the cam cylinder 70 is rotated. In the initial, restrained position, the first cam follower 66 is prevented from moving substantially distally or proximally by the first cam path 68, because the first cam path 68 is positioned relative to the first cam follower 66 substantially perpendicular to the direction in which the introducer tube 62 can translate, thereby substantially restraining the introducer tube 62 against translational motion. When the cam cylinder 70 is rotated and the first cam follower 66 encounters a segment of the first cam path 68 that extends in a direction having an axial component, the first cam follower 66 is free to translate a selected distance in the axial direction. Consequently, the introducer tube 62 that is connected to the first cam follower 66 is free to translate a selected distance in the axial direction, as is the seal housing 34 that is connected to the introducer tube 62.

Similarly, a second cam follower 84 extends from the carriage 58 into a second cam path 86 defined in the cam cylinder 70. The carriage 58 is restrained by the casing 98, introducer tube 62 and/or other structure or mechanism such that its motion is substantially linear in a direction substantially parallel to the axis of the introducer tube 62. In the initial, restrained position, as well as during translation of the second driveshaft 52, the second cam follower 84 is prevented from moving substantially distally or proximally by the second cam path 86. In that restrained position, the second cam path 86 is positioned relative to the second cam follower 84 substantially perpendicular to the direction in which the carriage 58 can translate, thereby substantially restraining the carriage 58 against translational motion. A segment of the second cam path 86 extends in a direction having an axial component. When the second cam follower 84 encounters such a segment of the second cam path 86, the second cam follower 84 is free to translate a selected distance in the axial direction, as is the carriage 58 that is connected to the second cam follower 84. The components connected to the carriage 58, such as the flexible shaft 24, the auger assembly 10 and the cutter 4, are also free to translate a selected distance in the axial direction. Thus, the motion of the auger assembly 10 and the cutter 4, as well as other components associated with them, can be controlled by rotation of the cam cylinder 70. That is, the cam paths 68, 86 allow translation of the associated followers 66, 84 when the cam paths 68, 86 are substantially parallel to the axis of the auger assembly 10, and substantially prevent motion of the associated followers 66, 84 when the cam paths are substantially perpendicular to the axis of the auger assembly 10. Alternately, only one of the cam followers 66, 84 is used to control the motion of the auger assembly 10 and the cutter 4.

Instead of a cam cylinder 70, a linear cam or a cam having another shape may be used to control the motion of the auger assembly 10 and the cutter 4. Further, in another embodiment, the motion of the auger assembly 10 and the cutter 4 is controlled by one or more different or additional mechanisms. For example, the auger assembly 10 and the cutter 4 may be connected to one or more DC motors or other powered mechanisms, where the motor is controlled by an integrated circuit or other computing device. By controlling the motor, the motion of the auger assembly 10 and the cutter 4 can be controlled.

Figure 1A:
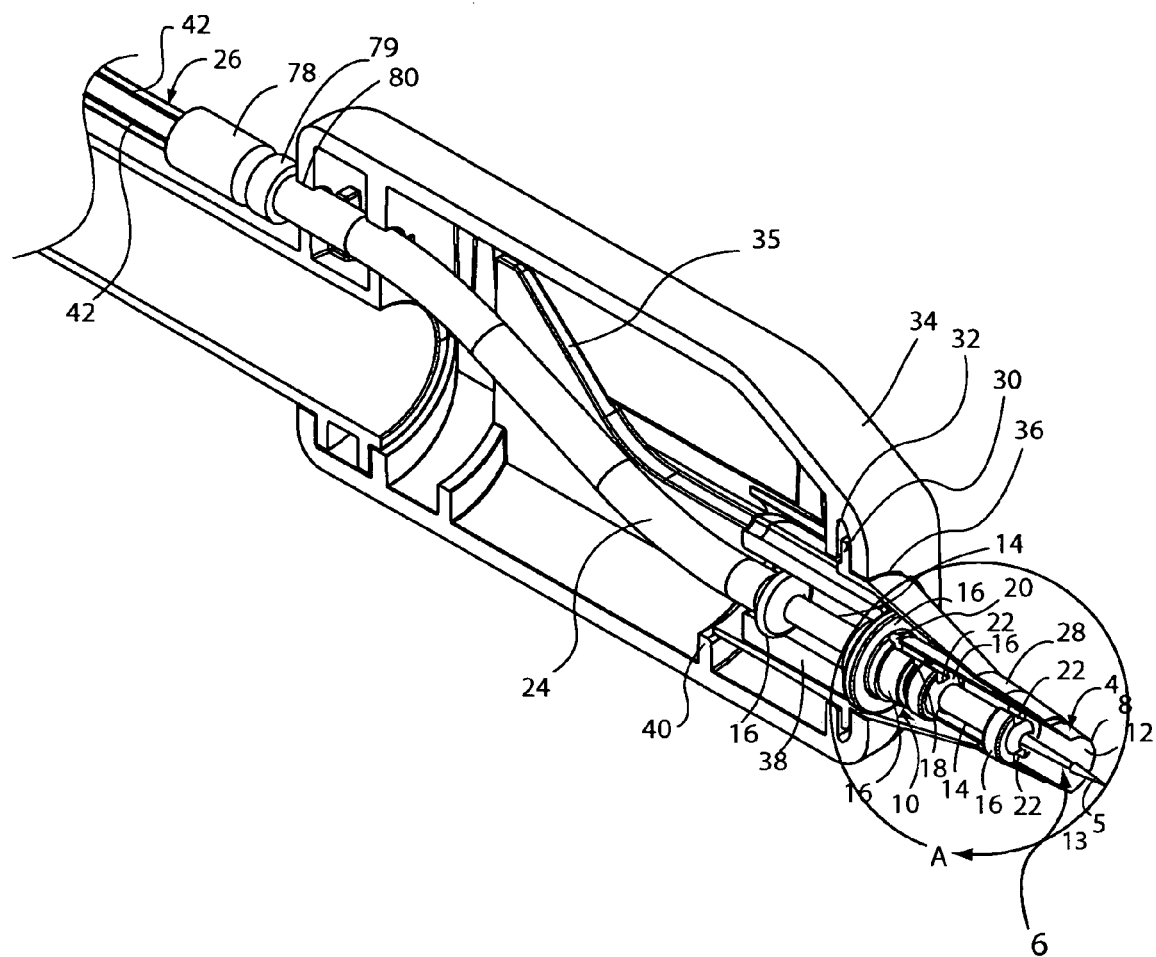
FIG. 1A is a cutaway view of the distal end of an assembly for creating an opening in the wall of a tubular vessel.

An assembly 82 is advanced distally as a unit at least partially as far as the first driveshaft 26 advances. The assembly 82 includes the first driveshaft 26, the carriage 58, the seal housing 34, the introducer tube 62, the flexible shaft 24, the auger assembly 10, the cutter 4 and the introducer tip 28. Other components may be included in the assembly 82. Referring also to FIG. 1A, a fitting 78 is connected to or formed into the first driveshaft 26 at or near its distal end. The fitting 78 is wider than the first driveshaft 26, and is substantially cylindrical. Alternately, the fitting 78 may be shaped differently. A shaft stop 79 is positioned proximally to the fitting 78. The shaft stop 79 is a tubular structure within which the flexible shaft 24 can rotate. The shaft stop 79 may assist in connecting the flexible shaft 24 to the fitting 78 and/or the first driveshaft 26. For example, the shaft stop 79 may compress a coil spring forming the flexible shaft 24 onto the surface of the distal end of the first driveshaft 26. The shaft stop 79 may be composed of polyethylene or other plastic, but may be formed from a different material or materials. The shaft stop 79 may be fixed to, or slidable relative to, the fitting 78.

The shaft stop 79 has a diameter larger than the diameter of the opening 80 in the seal housing 34 through which the flexible shaft 24 extends. The fitting 78 may similarly have a diameter larger than the diameter of the opening 80. The fitting 78 is positioned on the first driveshaft 26 at a location relative to the opening 80 such that the distal end of the fitting 78 engages the shaft stop 79, which in turn engages the seal housing 34 next to the opening 80, as the first driveshaft 26 is advanced distally. If the shaft stop 79 is fixed to the fitting 78, then the shaft stop 79 and the fitting 78 are already considered to be engaged upon distal advancement of the first driveshaft 26. Thus, the seal housing 34 is impelled distally along with the first driveshaft 26, due to contact between the shaft stop 78 and the seal housing 34. The initial distance between the shaft stop 78 and the seal housing 34 is related to the distance along which the assembly 82 is translated. As the seal housing 34 advances, the introducer tip 28 fixed to it is advanced into the opening created by the auger 6 and the cutter 4 in order to maintain hemostasis, as is described in greater detail below. Where the shaft stop 79 is not used, contact between the fitting 78 and the seal housing 34 impels the seal housing 34 distally. Further, the fitting 78 may be beveled or tapered at its distal end, and the seal housing 34 may include a beveled or tapered area adjacent to the opening 80 corresponding to any beveling or tapering of the fitting 78.

Alternately, the assembly 82 does not advance as a unit. Instead, the first driveshaft 26 advances the flexible shaft 24 distally, and the auger assembly 10 and cutter 4 advance distally as a result. The introducer tip 28 may be configured to advance into the opening created by the auger 6 and the cutter 4 at a later time, or may be configured to rest on the target vessel before the auger assembly 10 and the cutter 4 advance distally.

Figure 2:
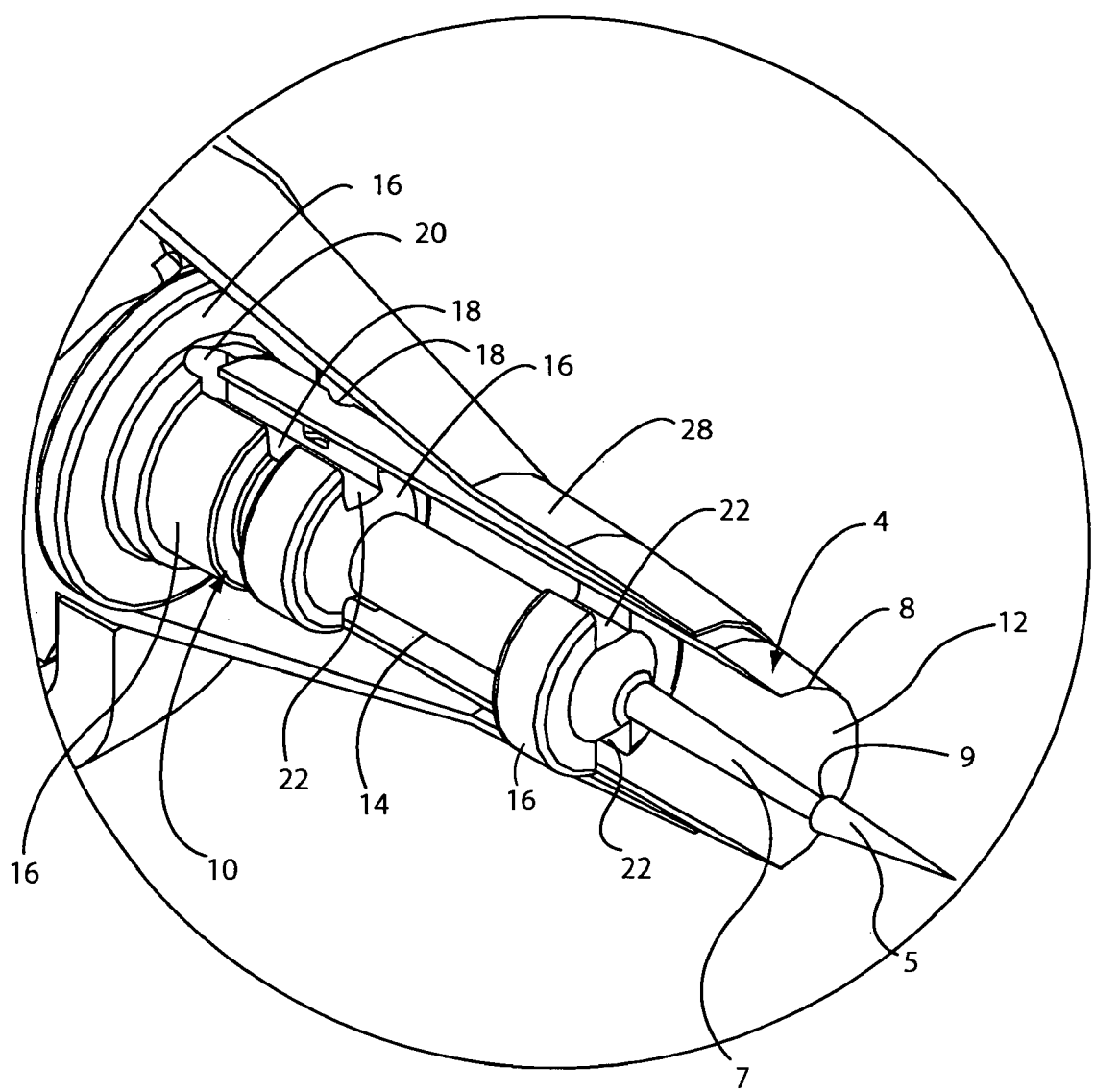
FIG. 2 is a detail view of the distal end of the assembly of FIG. 1.

The operation of the auger assembly 10 and the cutter 4 of FIGS. 1-3 will now be described. Referring to FIGS. 11-12, a contact structure 110 is connected to or formed into the casing 98, and has an open perimeter. The perimeter of the contact structure 110 may take the shape of a circle with an arc removed, a U-shape, or other shape. The contact structure 110 is placed against the vessel to substantially stabilize its surface within the perimeter of the contact structure 110, such that the tubular vessel is not substantially flattened by the pressure applied to it via the contact structure 110. The cutter 4 and the auger assembly 10 are free to rotate and translate a fixed amount relative to the contact structure 110. Thus, the total translation of the cutter 4 and auger 6 relative to the contact structure 110 is known. The cutter 4 and auger 6 are placed on the vessel at a location where the diameter of the vessel is large enough to ensure that the cutter 4 and auger 6 do not encounter the rear wall of the vessel during their travel relative to the contact structure.

The distal end of the spike 5 of the auger 6 extends distally beyond the distal surface of the contact structure 110. Thus, as the contact structure 110 is moved toward against the vessel, the distal end of the spike 5 penetrates the vessel wall before the contact structure 110 contacts the vessel. The entry into the vessel wall of the spike 5 prior to actuation of the cutter 4 and the auger 6 facilitates tissue removal from the vessel wall. The vessel wall is intact before the spike 5 enters it, and no separate incision need be made in the vessel wall before the spike 5 encounters it.

Energy is applied impulsively to the auger assembly 10 and the cutter 4. The auger assembly 10 and the cutter 4 then begin to rotate, as they advance distally into the vessel wall. Rotation begins at substantially the same time as translation. However, rotation or translation may begin first. The auger 6 advances into the wall of the tubular vessel as the cutter 4 advances and cuts. The cutting action of the cutter 4 is both rotational and axial. By constructing the auger 6 and the cutter 4 to be substantially smooth and radially symmetrical, the rotary motion of these structures creates a substantially smooth and clean hole through the vessel wall. The tissue of the tubular vessel may be strain rate sensitive, such as the tissue of the aorta. Strain rate sensitive tissue is easier to cut when the cutting is performed rapidly than when it is performed slowly. By actuating the auger 6 and the cutter 4 impulsively, they move rapidly such that the cutter 4 can better cut strain rate sensitive tissue.

After the cutter 4 has penetrated the entire vessel wall, it has cut tissue from that vessel wall, and formed an opening corresponding to the former position of that tissue. The cutter 4 cuts a substantially cylindrical tissue plug from the vessel wall due to its tubular shape. The spike 5 is positioned relative to the cutter such that the tissue plug is held within the cutter 4 due to engagement with the ledge 9 after the tissue plug has been cut. That is, the ledge 9 has advanced completely through the vessel wall before the cutter 4, such that the tissue plug cut from the vessel wall is located proximally to the ledge 9 upon its creation. The ledge 9 is wide enough to reliably hold the tissue plug within the cutter 4. The shaft 7 extends axially through the tissue plug, such that contact between the shaft 7 and the tissue plug acts substantially to prevent radial motion of the tissue plug in the cutter 4.

The distal translation of the cutter 4 and auger 6 continues through a fixed distance greater than the thickness of the vessel wall, to ensure that the cutter 4 has completely penetrated the vessel wall. Thus, the cutter 4 and auger 6 may continue to advance for a short distance after the tissue plug has been cut out of the vessel wall having a particular wall thickness. The cutter 4 and auger 6 are then retracted through the introducer tip 28. As they are retracted, they retract the tissue plug, leaving an opening in the vessel wall.

The introducer tip 28 follows the cutter 4 and the auger 6 into the vessel wall, and remains in the opening thus formed, in order to provide hemostasis with regard to that opening. The introducer tip 28 is hollow, and has a diameter slightly larger than the opening. Thus, the introducer tip 28 fits snugly within that opening in order to prevent leakage of fluid from within the vessel between the introducer tip 28 and the opening. Fluid such as blood enters the seal housing 34 through the introducer tip 28, and the seal housing 34 maintains hemostasis with regard to the fluid in the vessel. Alternately, the introducer tip 28 is not used, such that fluid such as blood enters the seal housing 34 through the cutter 4. One or more tools deployed through the introducer tube 62 have an outer diameter slightly smaller than the inner diameter of the introducer tube 62, such that the close fit between the introducer tube 62 and the tools deployed within it substantially provides hemostasis and prevents leakage from the seal housing 34. Alternately, a valve or seal (not shown) may be provided between the introducer tube 62 and the seal housing 34 to substantially prevent blood from entering the lumen of the introducer tube 62. Thus, the seal housing 34 maintains hemostasis in conjunction with the introducer tip 28 and/or the cutter 4. The introducer tip 28 may be omitted where the auger 6 and cutter 4 are part of an independent cutting tool rather than an integrated anastomosis tool or other integrated tool.

The auger assembly 10 and cutter 4 work similarly where the auger 6 is configured as shown in FIGS. 4-5. The contact structure 110 is placed against the vessel wall. The auger 6 and the cutter 4 initially are located proximal to the distal surface of the contact structure 110 and do not contact the vessel wall. As described above, energy is applied impulsively to the auger assembly 10 and the cutter 4, which begin to rotate and also begin to translate toward the wall of a tubular vessel. Thus, the auger assembly 10 and the cutter 4 each have both angular and linear momentum when they encounter the wall of the tubular vessel. The auger 6 encounters the vessel wall before the cutter 4, because the tip of the auger 6 extends distally beyond the distal end of the cutter 4. The vessel wall is intact before the auger 6 encounters it. That is, no separate incision need be made in the wall of the tubular vessel before the auger 6 and cutter 4 encounter it.

Figure 13:
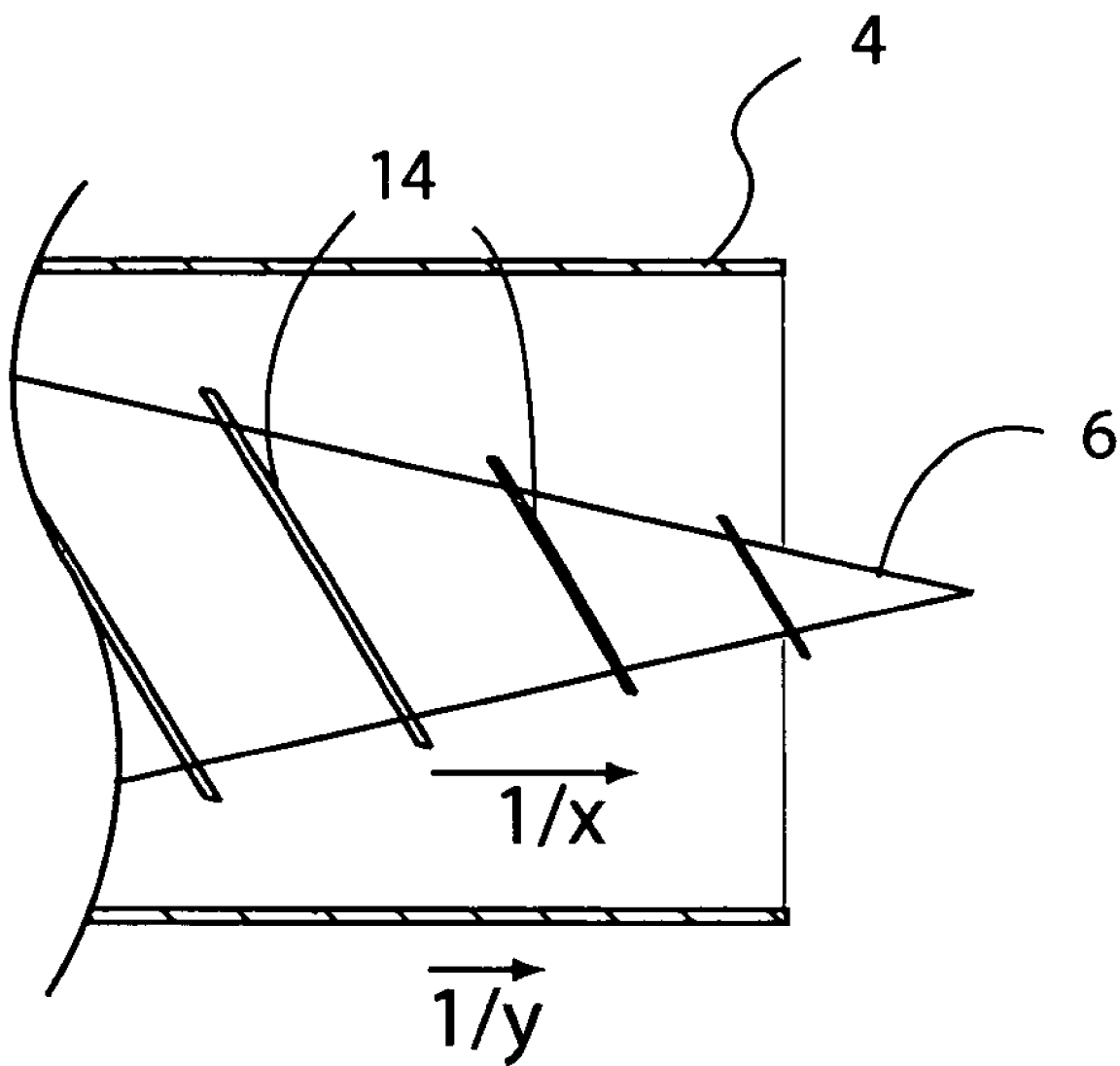
FIG. 13 is a detail view of the auger and cutter of FIGS. 4-5.

Referring also to FIG. 13, half of the cutter 6 is cut away in order to illustrate the auger 6 more completely. The auger flutes 13 have a pitch X, meaning that the flutes 13 cause the auger 6 to penetrate a distance 1/X into the wall of the tubular vessel for each revolution of the auger 6. Thus, at a pitch of 16 threads per inch, the auger 6 advances into the tubular vessel $\frac{1}{16}$ inch each revolution of the auger 6. Similarly, the threads of the threaded portion 72 of the first driveshaft 26 have a pitch Y. Thus, at a pitch of 25 threads per inch, the auger 6 and the cutter 4 translate distally $\frac{1}{25}$ inch each revolution of the first driveshaft 26. The auger assembly 10 and the first driveshaft 26 are fixed to one another and thus rotate at the same rate. The distance 1/X is greater than the distance 1/Y. Both distances are measured relative to the contact structure 110, which provides a point of reference as to the motion of the auger 6 and the cutter 4. The auger 6 advances into the wall of the tubular vessel faster than the cutter 4, even though the auger 6 and cutter 4 are impelled distally at the same rate. As a result, the auger 6 pulls the wall of the tubular vessel proximally as the cutter 4 advances distally, thereby pulling tissue into the cutter 4. The auger 6 pulls the wall of the tubular vessel intramurally; that is, by engaging the wall across its thickness using the flutes 13, to firmly and reliably engages the wall of the tubular vessel.

The cutter 4 is translated distally through the wall of the tubular vessel as the auger 6 holds a portion of the wall and pulls it proximally relative to the cutter 4. Thus, the cutter 4 cuts the tubular vessel from the outside while the auger 6 holds the wall of the tubular vessel. The auger 6 advances into the wall of the tubular vessel as the cutter 4 advances and cuts. The cutting action of the cutter 4 is both rotational and axial. The tissue of the tubular vessel may be strain rate sensitive, such as the tissue of the aorta. Strain rate sensitive tissue is easier to cut when the cutting is performed rapidly than when it is performed slowly. By actuating the auger 6 and the cutter 4 impulsively, they move rapidly such that the cutter 4 can better cut strain rate sensitive tissue, and enter the tissue quickly enough to minimize any effects of the tissue pulling outward from the opening in directions substantially perpendicular to the motion of the cutter 4. The pitch of the auger flutes 13 and the distance traveled by the cutter 4 during one rotation of the auger 6 are selected such that the auger 6 and cutter 4 cut a substantially cylindrical tissue plug from the wall of the tubular vessel. Alternately, the pitch of the auger flutes 13 and the distance traveled by the cutter 4 during one rotation of the auger 6 are selected such that the auger 6 and cutter 4 cut a substantially conical tissue plug from the wall of the tubular vessel. The conical tissue plug may be wider at its distal end or at its proximal end, depending on the selected pitch of the auger flutes 13 and the distance traveled by the cutter 4 during one rotation of the auger 6.

After the cutter 4 has penetrated the entire vessel wall, it has cut a tissue plug from that wall, and formed an opening corresponding to the former position of that tissue plug. The tissue plug is held firmly in the cutter 4 due to engagement with the auger flutes 13. The distal translation of the cutter 4 and auger 6 continues through a fixed distance greater than the thickness of the vessel wall, to ensure that the cutter 4 has completely penetrated the vessel wall. Thus, the cutter 4 and auger 6 may continue to advance for a short distance after the tissue plug has been cut out of the vessel wall. The cutter 4 and auger 6 are then retracted through the introducer tip 28. As they are retracted, they retract the tissue plug, leaving an opening in the wall of the tubular vessel.

Actuation of the auger 6 and the cutter 4 to remove a tissue plug from a vessel wall and create an opening therein may be performed in a number of different ways. Referring to FIGS. 11-12, in one exemplary embodiment, the cutter 4 and auger 6 are part of an integrated anastomosis tool 100. A single control on the integrated anastomosis tool 100 may be operated by the user to actuate the cutter 4 and the auger 6 and create an opening in the wall of the tubular vessel. This single control may be the knob 88, which is rotated through a preselected number of degrees in order to deploy the cutter 4 and auger 6, cut a tissue plug from the wall of the tubular vessel to form an opening in that wall, and retract the tissue plug out of the opening. A different control than the knob 88 may be provided, such as a lever, a slider, a button, or other control. The single control may be hand-driven, where force transmitted through the operator's hand drives at least part of the operation of the cutter 4 and auger 6, or may be powered, such that the operator simply presses a button or actuates a different control such that a powered mechanism such as a motor drives at least part of the operation of the cutter 4 and auger 6.

Referring to FIG. 11, the integrated anastomosis tool 100 is in the initial state; the auger 6 and the cutter 4 have not yet been deployed and the knob 88 is in an initial position. The user places the contact structure 110 against the wall of the tubular vessel in the location where the opening is to be made, without substantially deforming the tubular vessel. The user then begins to turn the knob 88. The stops 102 on the second driveshaft 52 are biased against the proximal surface 104 of the endplate 94 of the knob 88, as described above. The second driveshaft 52 does not substantially rotate upon rotation of the knob 88, because the registration features 64 connected to the second driveshaft 52 restrain the second driveshaft 52 against rotational movement, as described above. Initially, the slot 96 in the endplate 94 of the knob 88 is not aligned with the stops 102; instead, the stops 102 are in contact with the endplate 94 of the knob 88. At a preselected point in the angular travel of the knob 88, the slot 96 aligns with the stops 102, freeing the stops 102 to translate distally through the slot 102 and allowing the second driveshaft 52 to advance distally under the influence of the compression spring 106. Thus, the rotation of the knob 88 advances the second driveshaft 52 distally at a preselected point in the angular travel of the knob 88.

The distal advancement of the second driveshaft 52 translates the second gear 50 axially relative to the first gear 46. As described above, the first gear 46 is fixed, and engages the second gear 50 both before and after its advancement. As the second driveshaft 52 advances distally, the registration feature or features 64 advance distally relative to the structures or mechanisms that had previously restrained the second driveshaft 52 against rotation, freeing the registration feature or features 64. The second driveshaft 52 is then rotationally free, and begins to rotate driven by the energy stored within the spring 54. This stored energy is impulsively delivered, and in one embodiment causes the second gear 50 to rotate substantially three times. The gear ratio between the first gear 44 and the second gear 50 is chosen to produce the desired number of rotations of the second gear 50 upon release of stored energy from the spring 54. The second gear 50 rotates with the second driveshaft 52, causing the first gear 46 and the first driveshaft 26 to rotate in the opposite direction. Rotation of the first gear 46 also causes the first driveshaft 26 to advance distally, as described above. The actuator 24 transmits the rotary and translational motion of the first driveshaft 26 to the auger assembly 10 and the cutter 4.

The knob 88 is connected to the cam cylinder 70, such that rotation of the knob 88 rotates the cam cylinder 70. When the knob 88 is rotated to the position at which the second driveshaft 52 is allowed to advance distally, the first cam path 68 is positioned relative to the first cam follower 66 on the introducer tube 62 such that the first cam follower 66 and the introducer tube 62 are free to advance distally. The second cam follower 84 extending from the carriage 58 is prevented from moving substantially distally or proximally by the second cam path 86, which at this time is substantially perpendicular to the direction of motion of the introducer tube 62. Because the carriage 58 is held substantially fixed, the rotation of the threaded portion 72 of the first driveshaft 26 relative to the threaded passage 74 in the carriage 58 is converted to distal translation of the first driveshaft 26 as well. As the first driveshaft 26 advances distally, the fitting 78 on the first driveshaft 26 engages the shaft stop 79, which in turn engages the seal housing 34 and impels it forward. The seal housing 34 is connected to the introducer tube 62, and is free to advance distally along with the introducer tube 62. Thus, the seal housing 34 and the components fixed to it, such as the introducer tip 28, advance distally. The integrated anastomosis tool 100 is then in the deployed state of FIG. 12.

Where the auger 6 is fluted, as is FIGS. 4-5, the cam cylinder 70 controls the motion of the auger 6 and cutter 4 in the same manner as described above. The portions of the cam paths 68, 86 allowing for translation are longer than described above, because the auger 6 and the cutter 4 are initially spaced apart from the vessel wall, and thus travel a further distance during their actuation. The auger 6 and the cutter 4 penetrate the intact vessel wall, cut a tissue plug to form an opening, and retract the tissue plug from the opening in the same manner as described above.

The user continues to rotate the knob 88. After the tissue plug has been cut from the wall of the tubular vessel, it is restrained within the cutter 4 as described above. The auger 6 and cutter 4 continue advancing until they have traveled the entire preselected distance extending distally from the contact structure 110. The auger 6 and the cutter 4 then are retracted. The second cam follower 84 travels within the second cam path 86 in the cam cylinder 70. As the cam cylinder 70 rotates as the knob 88 is turned, the second cam path 86 moves proximally relative to the second cam follower 84. That is, the second cam path 86 has an axial component, such that contact between the second cam path 86 and the second cam follower 84 translates the second cam follower proximally. Because the second cam follower 84 is connected to the carriage 58, the carriage 58 also is moved proximally, such that the auger 6 and the cutter 4, as well as the tissue plug they restrain, are removed from the opening in the wall of the tubular vessel through the introducer tip 28, which remains in the opening. The bushing 38 is retracted along with the auger assembly 10. Thus, an assembly that includes the cutter 4, the auger assembly 10 and the bushing 38 is retracted from the opening in the wall of the tubular vessel. The orientation of the auger 6 before this retraction defines a first axis.

As the bushing 38 moves proximally, the guide follower or followers on the bushing 38 are guided by the guides 35 within the seal housing 34. The guides 35 extend away from the first axis in order to move the bushing 38 away from the first axis as the bushing is moved proximally. That is, the auger 6 and the cutter 4 are moved off-axis during retraction. In one embodiment, moving proximally, each guide 35 slopes in a direction toward the opening 80. Thus, as the bushing 38 is retracted proximally, the guide followers encounter the upward-sloping guides 35, which cause the bushing 38 to move off the first axis to a second axis. The guide followers need not contact the guides 35 at all points during the retraction of the bushing. Indeed, the actuator 24 itself may be configured to bias the bushing 38, auger assembly 10 and cutter 4 away from the first axis. In this way, the auger 6, cutter 4 and the tissue plug that they retain, as well as the bushing 38, are moved off the first axis such that an anastomosis device can be deployed along the first axis through the introducer tube 62. Further, moving the auger 6 and cutter 4 off the first axis allows the tissue plug to be removed from the opening without being retracted through the graft vessel. By moving the tissue plug into a location within the seal housing 34, hemostasis is maintained.

Alternately, the guides 35 and guide followers need not be provided. For example, the guides 35 and guide followers may be unnecessary where the auger 6 and cutter 4 are not part of an integrated tool. As another example, the bushing 38, auger assembly 10 and cutter 4 may be retracted substantially along the first axis, and an anastomosis device is moved from another axis to the first axis for deployment. In such an example, the bushing 38 need not be moved off the first axis, and the guides 35 and guide followers are not required.

Figure 16:
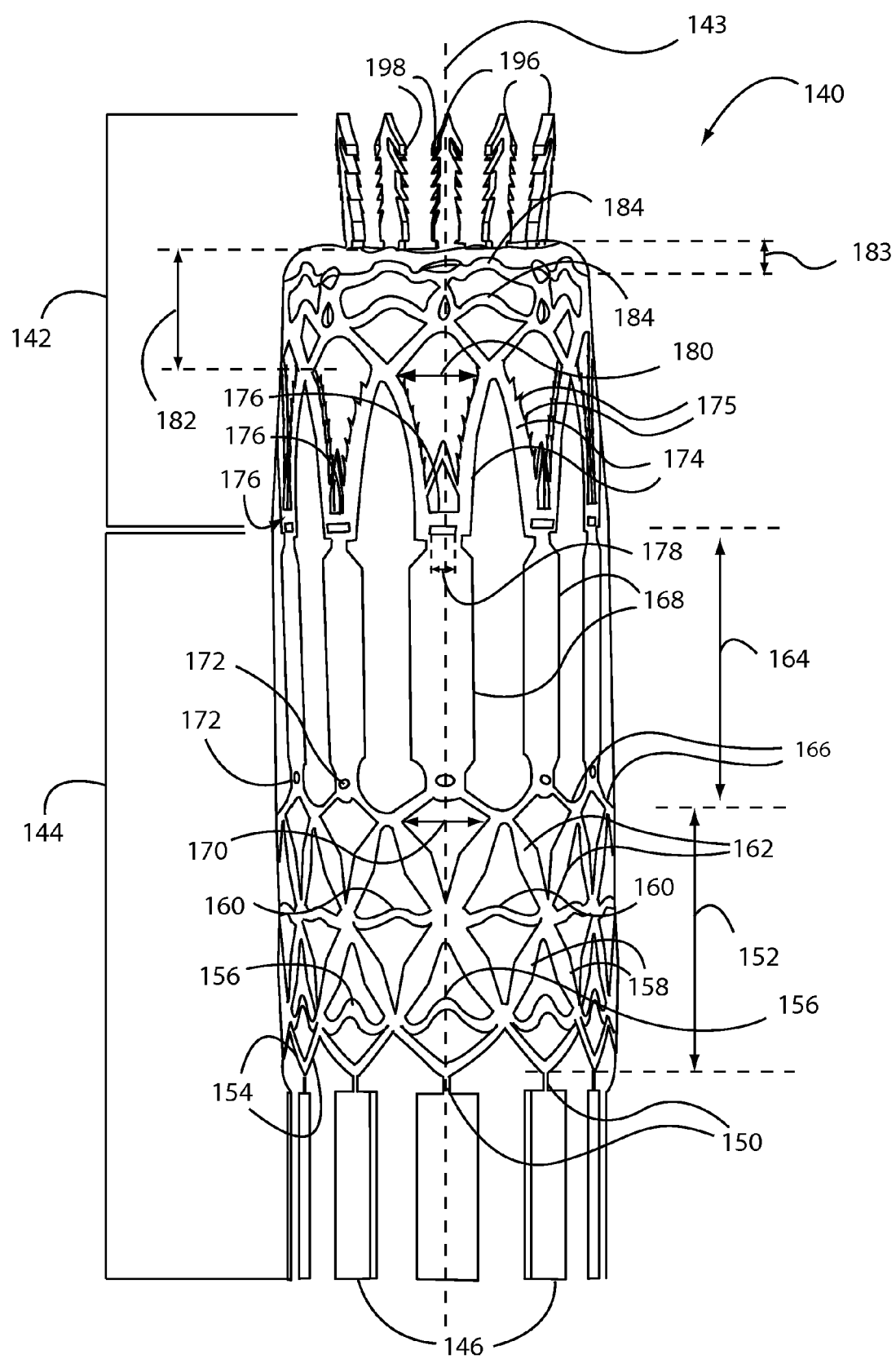
FIG. 16 is a side view of an anastomosis device.
Figure 17:
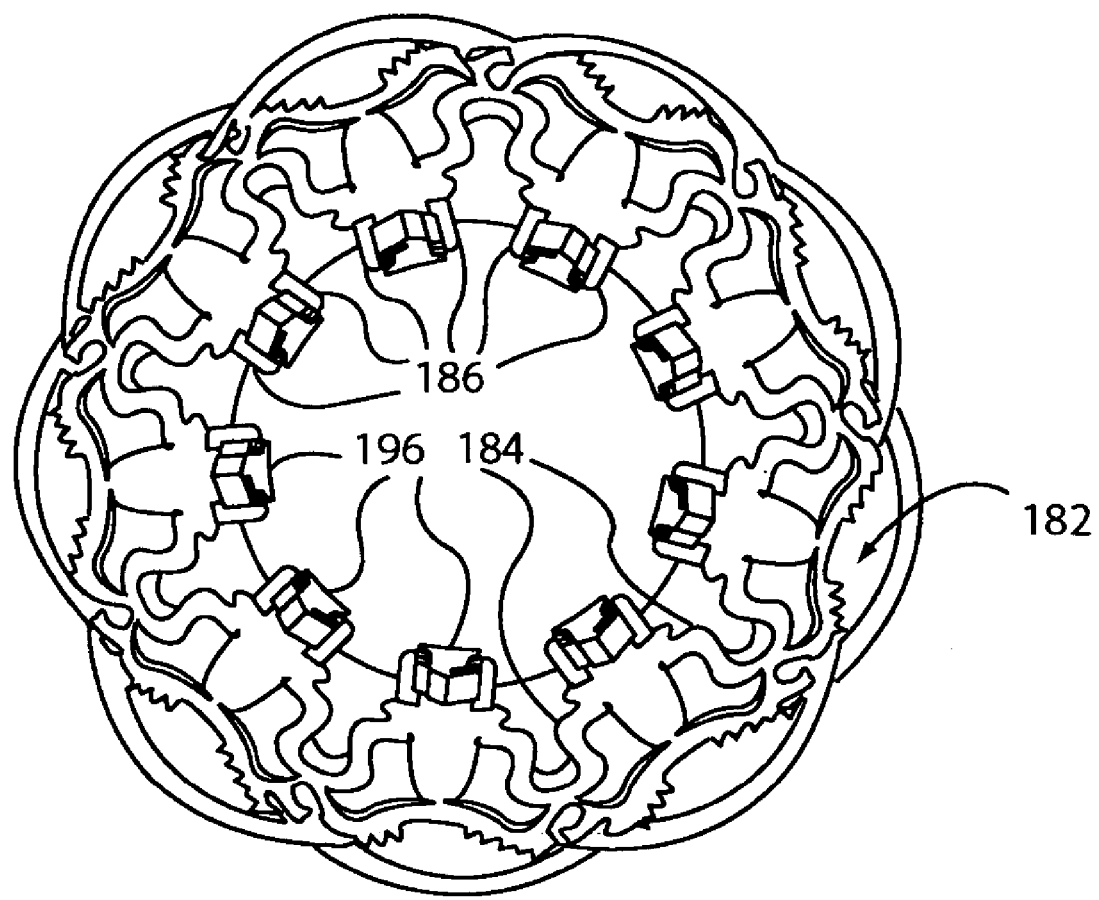
FIG. 17 is an end view of the distal end of the anastomosis device of FIG. 16.
Figure 18:
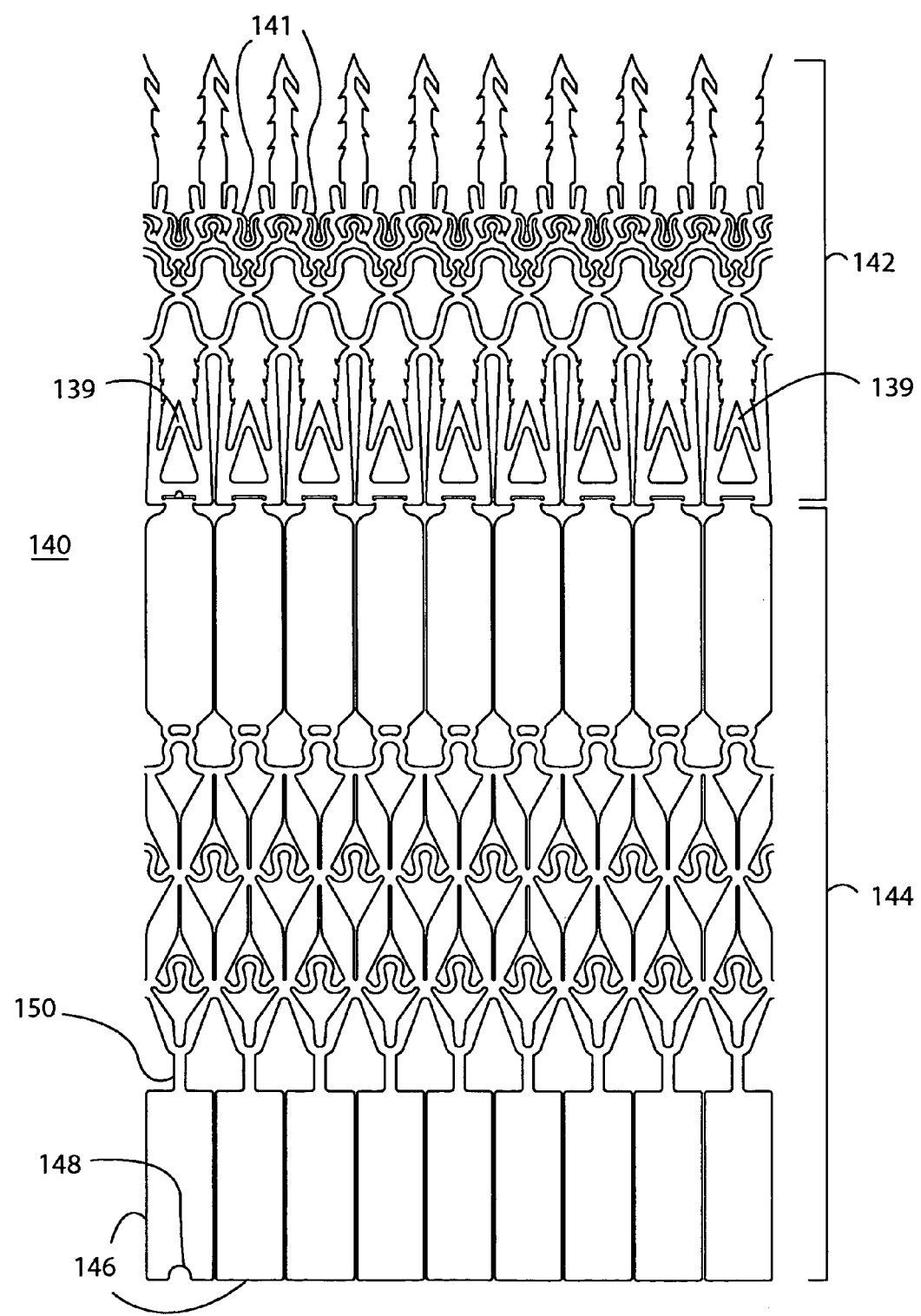
FIG. 18 is a top view of a tubular structure from which the anastomosis device of FIG. 16 is formed, unrolled into a planar configuration.
Figure 19:
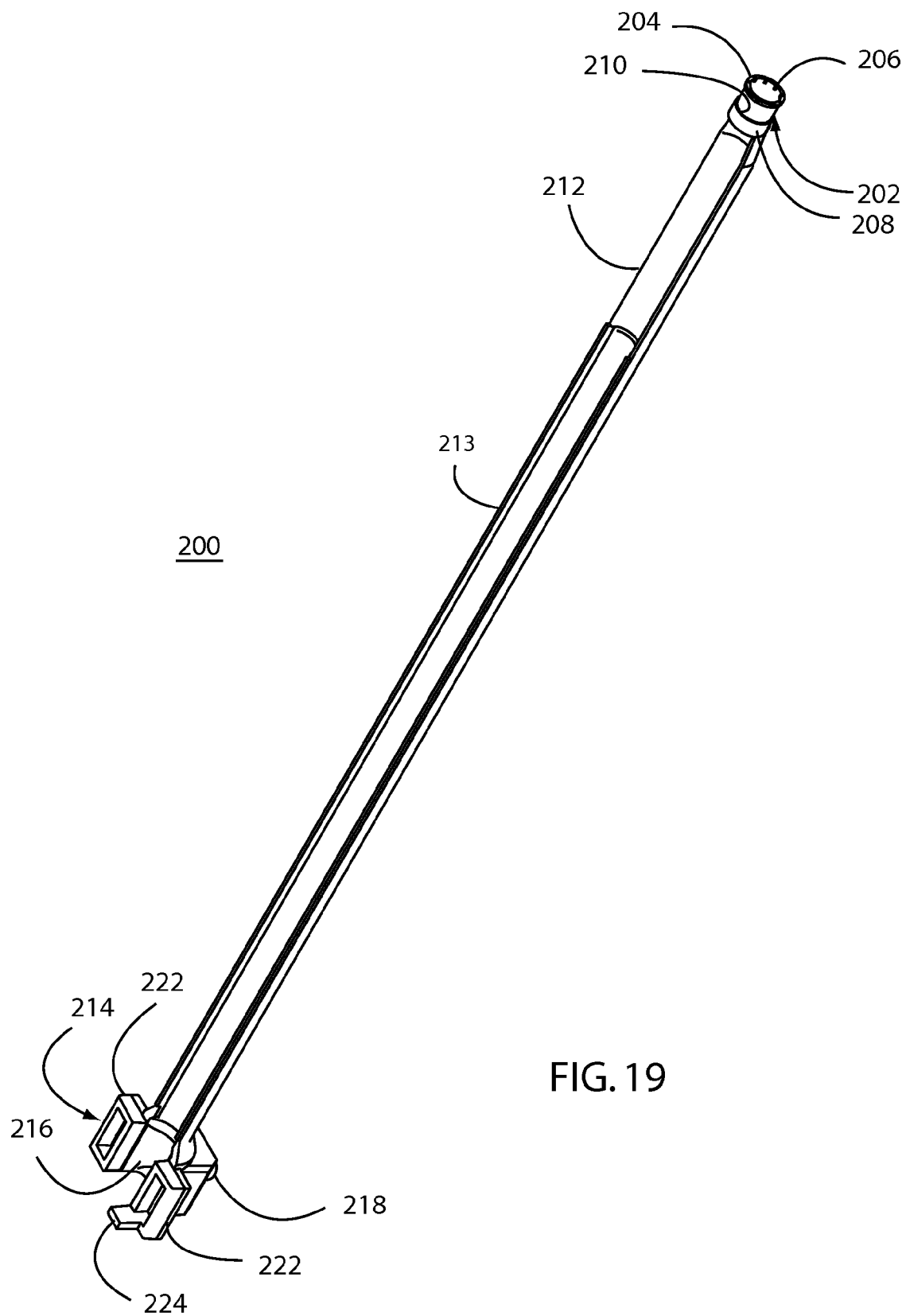
FIG. 19 is a perspective view of a crown.
Figure 20:
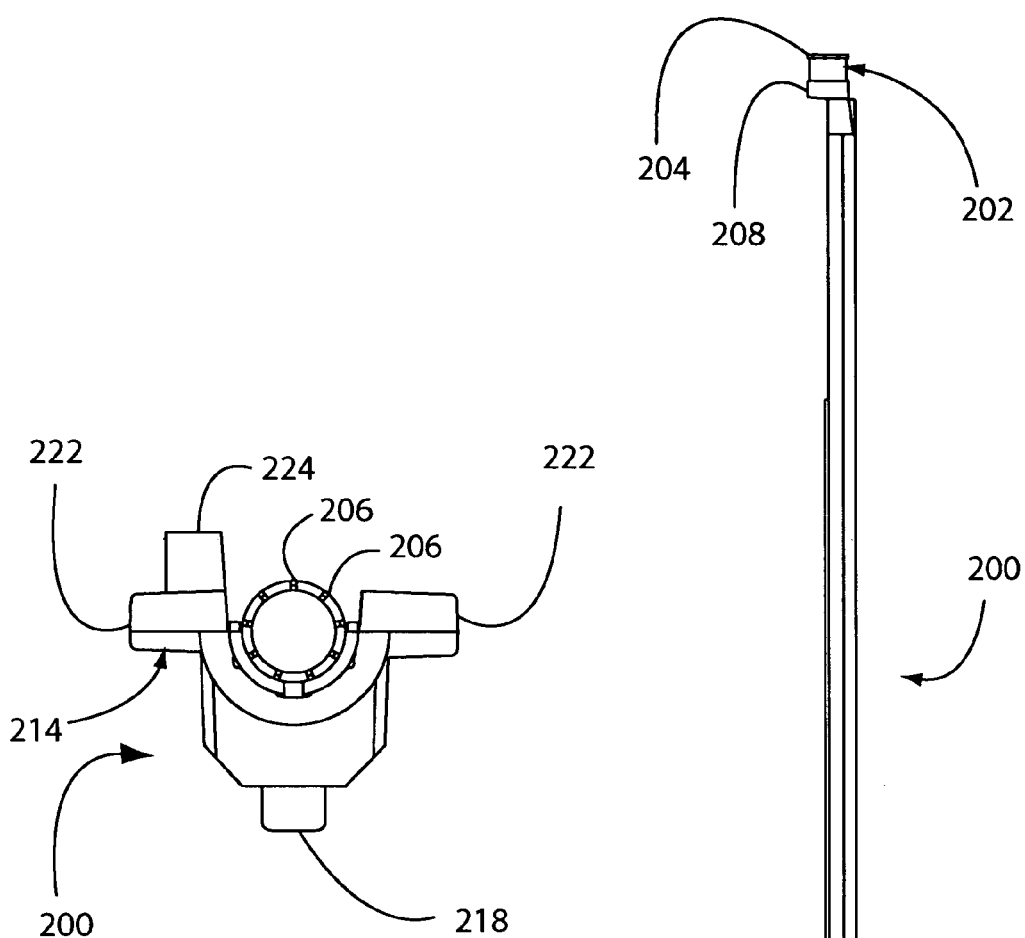
FIG. 20 is an end view of the crown of FIG. 19.
Figure 21:
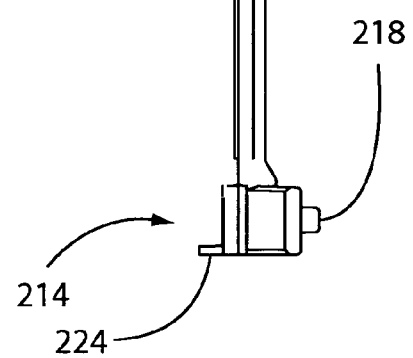
FIG. 21 is a side view of the crown of FIG. 19.

After the auger 6 and cutter 4 have created the opening in the vessel wall, the anastomosis device 140 is placed in the opening in the vessel wall and deployed. Referring to FIGS. 16-18, the anastomosis device 140 is composed of 316L stainless steel. A different type of stainless steel may instead be used. Further, a different biocompatible material or combination of materials may be used. The anastomosis device 140 is constructed by laser-cutting through the walls of a hollow tube. The walls of the hollow tube are substantially 0.008 inches thick. Another method of construction and/or another wall thickness may be used. Referring to FIG. 18, a view of the laser-cut tube unrolled into a planar configuration is shown. The hollow tube is then shaped at its distal end to form the anastomosis device 140, which has an initial, pre-deployment shape as shown in FIGS. 16-17.

The anastomosis device 140 includes a deployable section 142 and a discard section 144. The deployable section 142 is configured to be placed in and deployed into the opening in the vessel wall. The discard section 144 is retained by the integrated anastomosis tool 100 after the deployable section 142 is deployed. The discard section 144 is located at the proximal end of the anastomosis device 140, and the deployable section 142 is located at the distal end of the anastomosis device 140. The entire anastomosis device 140, including both the deployable section 142 and the discard section 144, is substantially radially symmetrical about its axis 143. Alternately, the deployable section 142, the discard section 144, or both may be radially asymmetrical.

One or more connection structures are located at the proximal end of the discard section 144. The connection structures are used to connect the anastomosis device 140 to the integrated anastomosis tool 100, as described in greater detail below. As one example, paddles 146 may be used as interface structures. However, other interface structures may be used, if desired. The paddles 146 have an arcuate cross-section with a radius of curvature substantially the same as the tube from which the anastomosis device 140 was manufactured. Alternately, the paddles 146 have a different radius of curvature, or are substantially flat. The paddles 146 are each substantially the same radial distance from the axis 143 of the anastomosis device 140. The paddles 146 each extend substantially axially, but may be oriented differently if desired. Optionally, referring to FIG. 18, at least one paddle 146 may include a registration feature 148 defined in its proximal end, where contact between the registration feature 148 and a corresponding feature within the integrated anastomosis tool 100 is used to ensure the proper placement of the anastomosis device 140. Referring back to FIGS. 16-17, at least one leg 150 extends substantially axially from each paddle 146. One or more legs 150 may extend in a different direction, if desired. The legs 150 are used in connecting the anastomosis device 140 to the integrated anastomosis tool

100, as described below. The legs 150 also connect each paddle 146 to a compression segment 152 on the anastomosis device 140.

The compression segment 152 is a section of the anastomosis device 140 that is located distal to the legs 150. The compression segment of 152 extends axially in a distal direction from the legs 150. The compression segment 152 is a linkage that has a substantially circular cross-section, as viewed along the axis 143 of the anastomosis device 140. The function of the compression segment 152 is described in greater detail below. The compression segment 152 includes at its proximal end first struts 154, two of which extend distally from each leg 150. Each first strut 154 also extends at an angle to the direction of the leg 150 which it is connected. Thus, the distal ends of the adjacent struts 154 are connected to one another. The first struts 154 viewed alone form a substantially zigzag configuration. A first expandable member 156 is connected at each end to the distal end of adjacent struts 154. The first expandable members 156 are oriented in a substantially circumferential direction around the compression segment 152. Two second struts 158 extend distally to and angularly outward from each intersection between two adjacent first expandable members 156. Each second struts 158 intersects with the adjacent second struts 158 at a location distal to the first expandable members 156. A second expandable member 160 is connected at each end to the distal end of adjacent struts 158. The second expandable members 160 are oriented in a substantially circumferential direction around the compression segment 152. Two third struts 162 extend distally to and angularly outward from each intersection between two adjacent second expandable members 160. Each second strut 158 is substantially aligned with a third struts 162 distal to it. Thus, adjacent pairs of second struts 158 and third struts 162 form an X-shaped configuration. The expandable members 156, 160 allow for radial expansion, but also limit radial expansion. That is, each expandable member 156, 160 is configured to expand a predetermined amount. When that amount of expansion has been reached, the expandable members 156, 160 substantially stop expanding, thereby substantially halting radial expansion. In this way, the final diameter of the anastomosis device 140 can be preselected and controlled.

The third struts 162 connect the compression segment 152 to the separation area 164. Within the separation area 164, two fourth struts 166 extend distally to and angle outward from each intersection between two third struts 162. The distal end of each fourth strut 166 is connected to the proximal end of a spreader arm 168. With regard to the two fourth struts 166 connected to a particular spreader arm 168, the proximal end of each such fourth strut 166 is connected to a different intersection between two third struts 162. The linear distance between those two intersections may be called the first distance 170. The first distance 170 is substantially the same between any two such adjacent intersections. Alternately, the first distance 170 may vary between different adjacent intersections. These two intersections are also positioned at a first radial distance from the axis 143. The proximal end of each spreader arm 168 may include one or more holes 172 therethrough for stress management. Further, the width of each spreader arm 168 at its proximal end may be less than the width of the spreader arm 168 at a more distal location. The distal ends of the spreader arms 168 initially may be angled outward from the axis 143 a small amount. Alternately, a single, wide fourth strut 166 is connected to the proximal end of each spreader arm 168, in which case the first distance 170 is the width of the proximal end of the fourth strut 166. Alternately, three or more fourth struts 166 may be used, in which case the first distance 170 is the linear distance between the two furthest-separated fourth struts 166.

The distal end of each spreader arm 168 is connected to two outer flange arms 174 in such a way as to allow each spreader arm 168 and its associated outer flange arms 174 to move outward at an angle to the axis 143, then separate the two, as described in greater detail below. Each spreader arm 168 narrows in width at its distal end. The outer flange arms 174 connect to the sides of the distal end of the spreader arm 168, such that a space is located distally from the distal end of the spreader arm 168. The contact area between the spreader arm 168 and the connected outer flange arms 174 is selected to allow them to hinge relative to one another and move outward away from the axis 143. The width of the distal end of the spreader arm 168 may be called the second distance 178. The distal end of the spreader arm 168 is positioned at a second radial distance 178 from the axis 143 of the anastomosis device 140.

Figure 34:
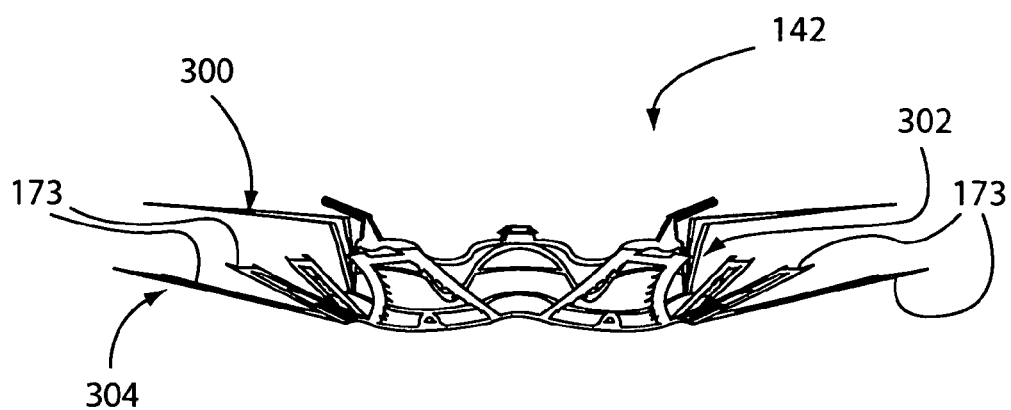
FIG. 34 is a side view of the anastomosis device after deployment.
Figure 35:
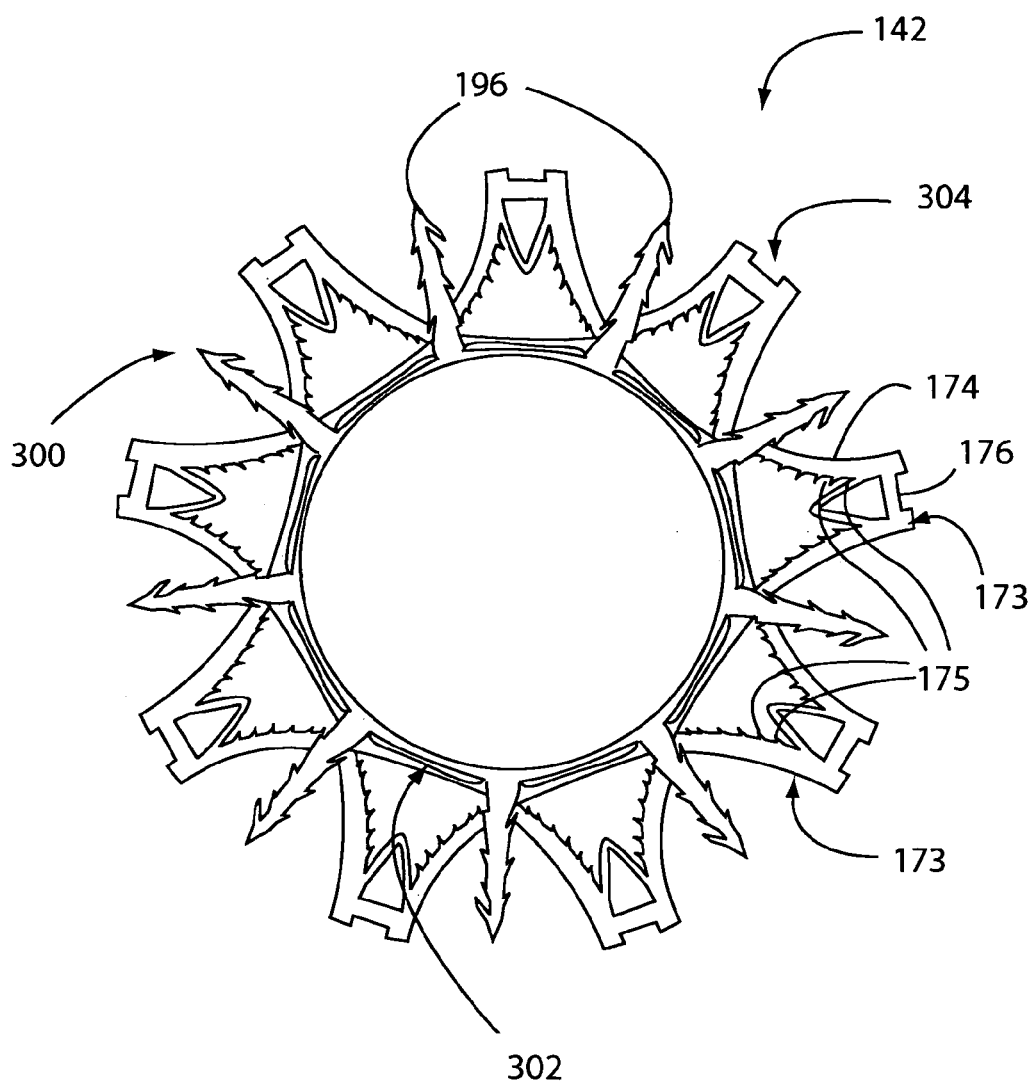
FIG. 35 is a top view of the anastomosis device after deployment.

A crossbar 176 links the two outer flange arms 174 that are connected to a single spreader arm 168, and is spaced distally away from the distal end of the spreader arm 168. Each outer flange arm 174 may include a number of gripping elements 175 formed into it. Referring also to FIGS. 34-35, each pair of outer flange arms 174 and connecting crossbar 176 forms an outer flange element 173 in the deployed state. Moving distally, the two outer flange arms 174 connected to a single spreader arm 168 extend circumferentially outward relative to each other. At its distal end, each outer flange arm 174 intersects an adjacent outer flange arm 174. The distance between the distal ends of the two outer flange arms 174 connected to a single spreader arm 168 may be called the third distance 180. The distal ends of those two outer flange arms 174 are also each located at a third radial distance from the axis 143 of the anastomosis device 140. The third distance 180 is greater than the second distance 178, and the first distance 170 is greater than the second distance 178. Advantageously, the third distance 180 is greater than the first distance 170. Further, the first radial distance and the third radial distance are greater than the second radial distance 178. Alternately, a single differently-configured outer flange element 173 is used in place of the combination of two outer flange arms 174 and a crossbar 176, in which case the third distance 180 is the width of the distal end of the single outer flange element 173. Alternately, more than two outer flange arms 174 may be used in conjunction with one or more crossbars 176 to form an outer flange element 173, in which case the third distance 180 for that outer flange element 173 is the linear distance between the two furthest-separated outer flange arms 174.

Optionally, a chevron 139 is associated with each pair of outer flange arms 174 connected to a single spreader arm 168. The chevron 139 is a V-shaped element that has two ends, each connected to an outer flange arm 174 at or distal to the intersection between that outer flange arm 174 and the corresponding spreader arm 168. The chevron 139 extends distally from each intersection with an outer flange arm 174 such that its pointed tip is positioned at a distance approximately halfway between two adjacent outer flange arms 174. The chevrons 139 assist in gripping the outer surface of the target vessel, as described below.

The distal ends of the outer flange arms 174 are connected to a linkage 182 that forms the body of the deployable section 142. The linkage 182 curves inward at its distal end. The section of the linkage 182 that curves inward may be referred to as the ring 183. The linkage 182 is configured to expand radially at its distal end during deployment, as is described in greater detail below. Thus, a number of expandable members 184 are positioned substantially circumferentially around the linkage 182, such that the linkage 182 is free to expand radially upon the application of an appropriate force.

Tines 196 extend distally from the distal end of the linkage 182. The tines 196 extend substantially parallel to the axis 143 of the anastomosis device 140. Alternately, the tines 196 may be angled slightly inward, or may instead angle outward slightly relative to the axis 143 of the anastomosis device 140. Each tine 196 has a sharp point at its distal end, and a number of teeth 198 defined along its length. When deployed, the tines 196 form the inner flange of the deployable section 142. The tines 196 are mounted on expandable members 184 of the linkage 182. Thus, as the linkage 182 expands radially upon the application of appropriate force, the intersections between each tine 196 and the corresponding expandable member 184 expand away from each other. The teeth 198 on the tines 196 assist in gripping the inner surface of the target vessel and holding the deployable section 142 securely onto the target vessel.

Figure 39:
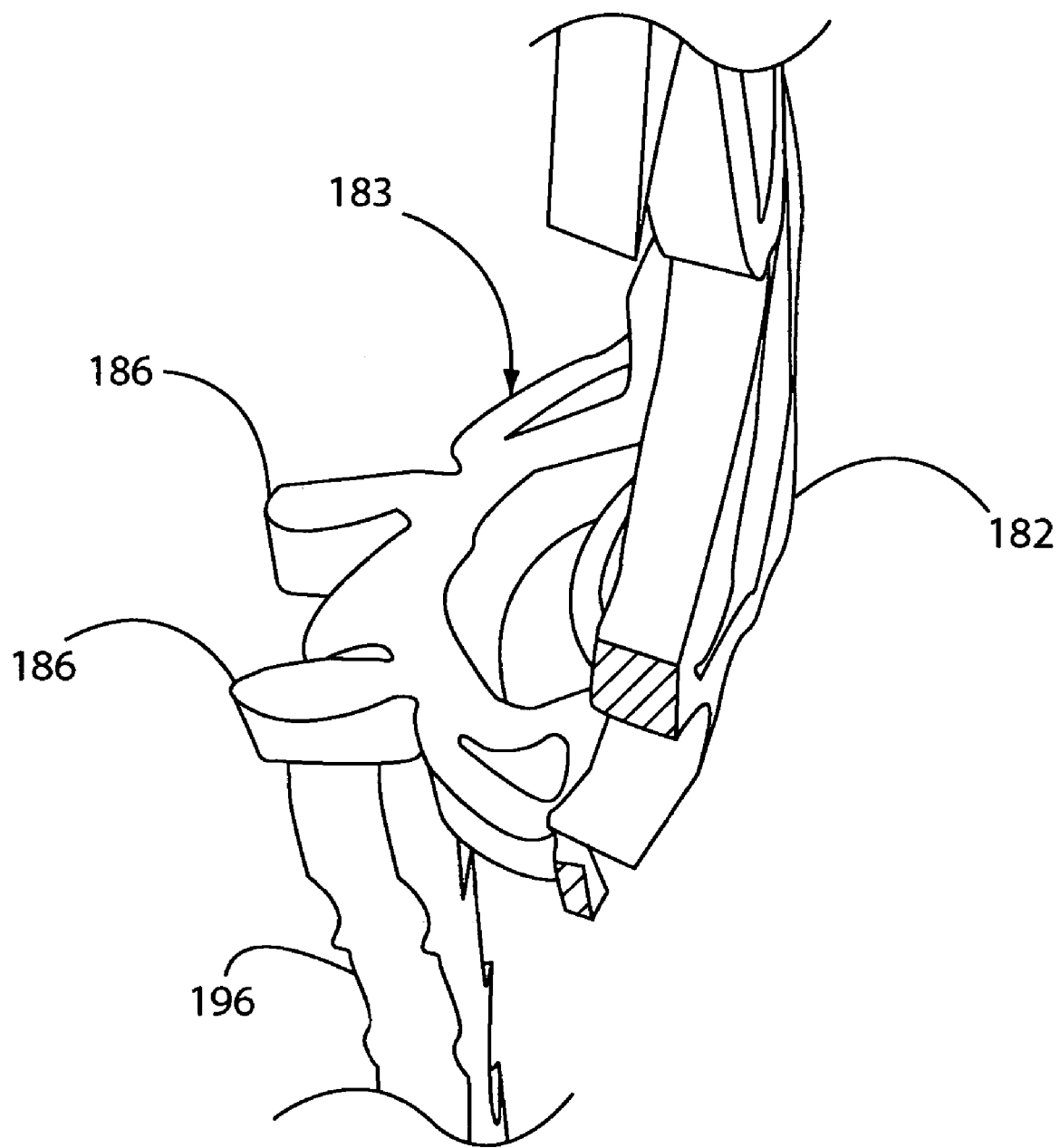
FIG. 39 is a perspective view of a portion of the deployable section of the anastomosis device.
Figure 40:
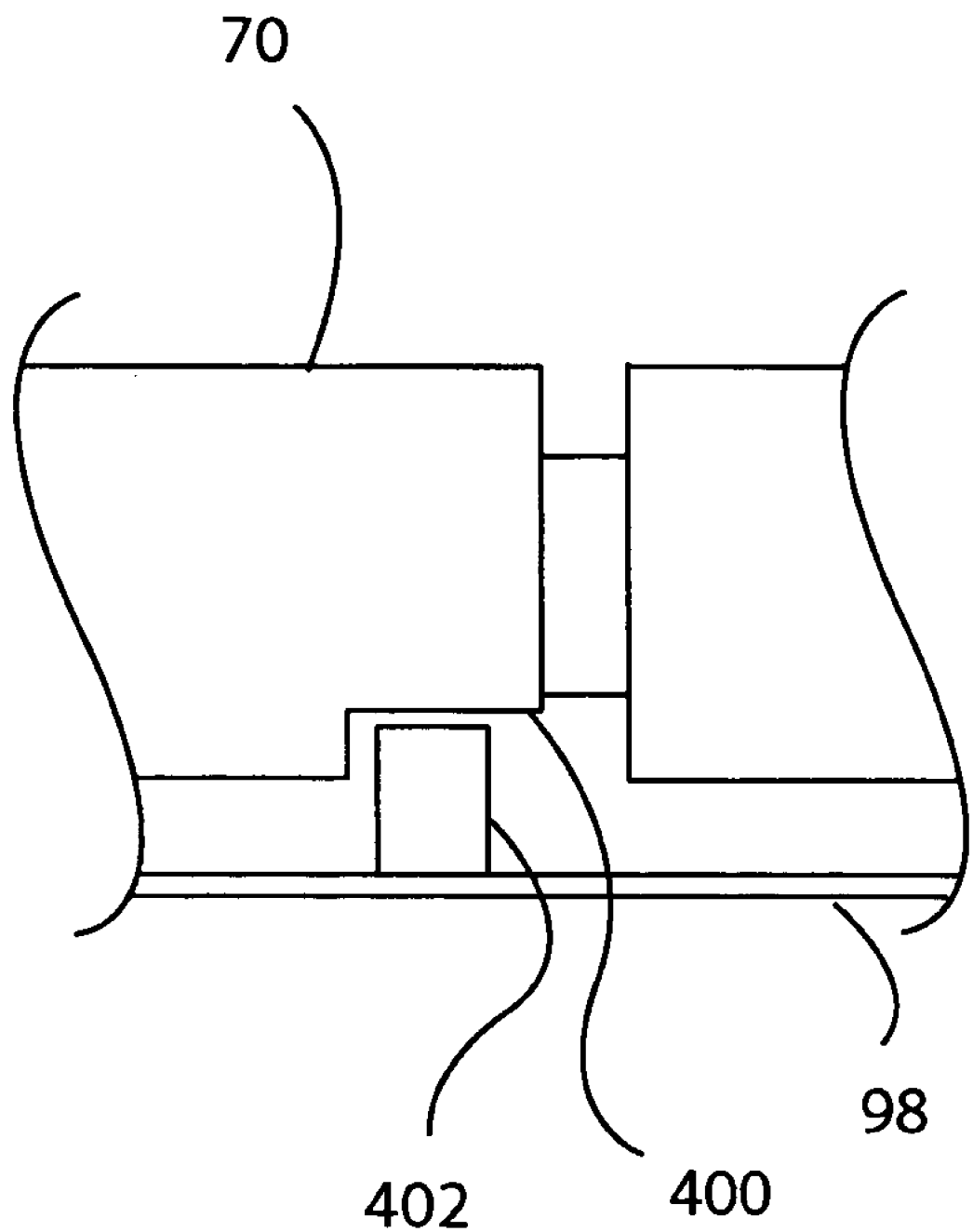
FIG. 40 is a detail view of a portion of the cam cylinder of FIGS. 38A-D.

Referring also to FIG. 39, at least one horn 186 extends from the linkage 182 in proximity to each intersection between the linkage 182 and a tine 196. Advantageously, two horns 186 are provided adjacent each tine 196, one on either side. The horns 186 extend at least partially in a radial direction, inward toward the axis 143 of the anastomosis device 140. The horns 186 are configured to engage the expander tip 280 at an appropriate time during the deployment of the anastomosis device 140, as described below.

Optionally, the anastomosis device 140 may be configured to actively counteract intimal hyperplasia. Intimal hyperplasia is a condition in which the intimal cells lining a vessel proliferate into the anastomosed graft. While the anastomosis device 140 is not expected to cause intimal hyperplasia in most patients, it may be desirable to provide the capability for the anastomosis device 140 to counteract it. For example, the anastomosis device 140 may be drug-eluting, meaning that it releases a drug over time into the surrounding tissue, where that drug acts to inhibit or counteract intimal hyperplasia in the vicinity of the anastomosis device 140. Such drugs may include rapamycin, paclitaxel, and actinomycin D. One or more of these drugs may be directly applied to the surface of the anastomosis device 140, or may be contained in a carrier matrix (not shown) attached to or formed in the anastomosis device 140. As another example, the anastomosis device 140 may include a source of ionizing radiation, which may be useful in inhibiting or counteracting intimal hyperplasia in the vicinity of the anastomosis device 140. Optionally, the anastomosis device 140 may be configured to elute a different drug or an additional drug to treat one or more other conditions of the patient as well.

Referring also to FIGS. 19-21 and 36, the anastomosis device 140 is connected to a crown 200. A crown collar 202 is located at the distal end of the crown 200. The crown collar 202 is a substantially tubular structure defining a lumen therethrough. A ridge 204 extends substantially radially around the circumference of the distal end of the crown collar 202. Alternately, the ridge 204 extends in a direction other than radially, and/or does not extend around the entire circumference of the distal end of the crown collar 202. At least one slot 206 is defined in the ridge 204. Each slot 206 is oriented substantially radially, and extends substantially axially. However, the slots 206 may be oriented differently, or extend in a different direction. A second ridge 208 also extends substantially radially around the circumference of the proximal end of the crown collar 202. Thus, a ledge 210 is present at the intersection of the distal end of the second ridge 208 and the crown collar 202.

Referring also to FIGS. 16-17, the proximal ends of the paddles 146 of the anastomosis device 140 may abut the ledge 210, in order to facilitate construction of the integrated anastomosis tool 100 and provided positive confirmation of the axial position of the paddles 146 with regard to the crown collar 202. If a registration feature or features 148 are provided on one or more paddles 146, then the surface of the crown collar 202 or the ledge 210 includes corresponding features for mating with those registration features 148. The crown collar 202 is configured to receive the paddles 146 on its surface. Thus, the shape of the surface of the crown collar 202 substantially matches the cross-section of the paddles 146. Before the anastomosis device 140 is placed onto the crown 200, the paddles 146 are bent outward at an angle to the axis 143 of the anastomosis device 140. This outward bending may be performed at the same time as the distal end of the anastomosis device 140 is shaped, or at a different time. The paddles 146 are bent outward substantially ninety degrees, but may instead be bent at a different angle. The anastomosis device 140 is then brought into proximity with the crown collar 202, such that the legs 150 of the anastomosis device 140 are located radially outward from the slots 206. The paddles 146 are then bent inward toward the axis 143 of the anastomosis device 140. This bending motion of the paddles 146 causes the legs 150 to rotate along an axis perpendicular to the axis 143 of the anastomosis device 140. The legs 150 are thereby impelled into the slots 206 in the ridge 204 to a final position in which the legs 150 are substantially parallel to the axis 143. The slots 206 and the legs 150 are aligned relative to one another to allow the legs 150 to enter the slots 206. The slots 206 and corresponding legs 150 are sized relative to one another to fit tightly, such that contact between the slots 206 and legs 150 alone is sufficient to hold the anastomosis device 140 onto the crown collar 202. Optionally, additional structures, mechanisms or methods may be used to provide a stronger bond between the anastomosis device 140 and the collar 202. For example, a heat-shrinkable material may be placed circumferentially around the crown collar 202, on top of the paddles 146, after which heat is applied to it. That shrinkable material provides additional holding force between the crown collar 202 and the paddles 146. As another example, an adhesive may be placed between the paddles 146 and the crown collar 202. As another example, the anastomosis device 140 could be heat-staked onto the crown collar 202. As another example, the anastomosis device 140 could be insert-molded to the crown collar 202.

A crown body 212 extends proximally from the proximal end of the crown collar 202. The crown body 212 is an open half-tube, having a semicircular cross-section. The opening configuration of the crown body 212 allows the crown 200 to receive an expander, which is described in greater detail below. A rail 213 extends along at least one of the two edges of the crown body 212. Each rail 213 extends in a direction substantially tangent to the curvature of the crown body 212 at the edge of the crown body 212. The outer surface of each rail 213 is substantially flush with the outer surface of the crown body 212. An interface 214 is located at the proximal end of the crown body 212. The interface 214 includes a semicircular recess 216 aligned with the crown body 212. A third cam follower 218 extends downward from the interface 214. Referring also to FIGS. 38A-D, the third cam follower 218 is configured to engage a third cam path 220 defined in the cam cylinder 70. The interface 214 also includes two flanges 222 configured to slide within corresponding grooves in a cartridge, which is described in greater detail below. A tab 224 extends substantially upward from the one of the flanges 222. Referring also to FIG. 41, the crown 200 is positioned within, and is configured to slide relative to, the introducer tube 62. The outer radius of curvature of the crown body 212 is substantially the same as the inner radius of curvature of the introducer tube 62. Thus, the introducer tube 62 substantially stabilizes the crown 200 radially and guides the translational motion of the crown 200.

Figure 22:
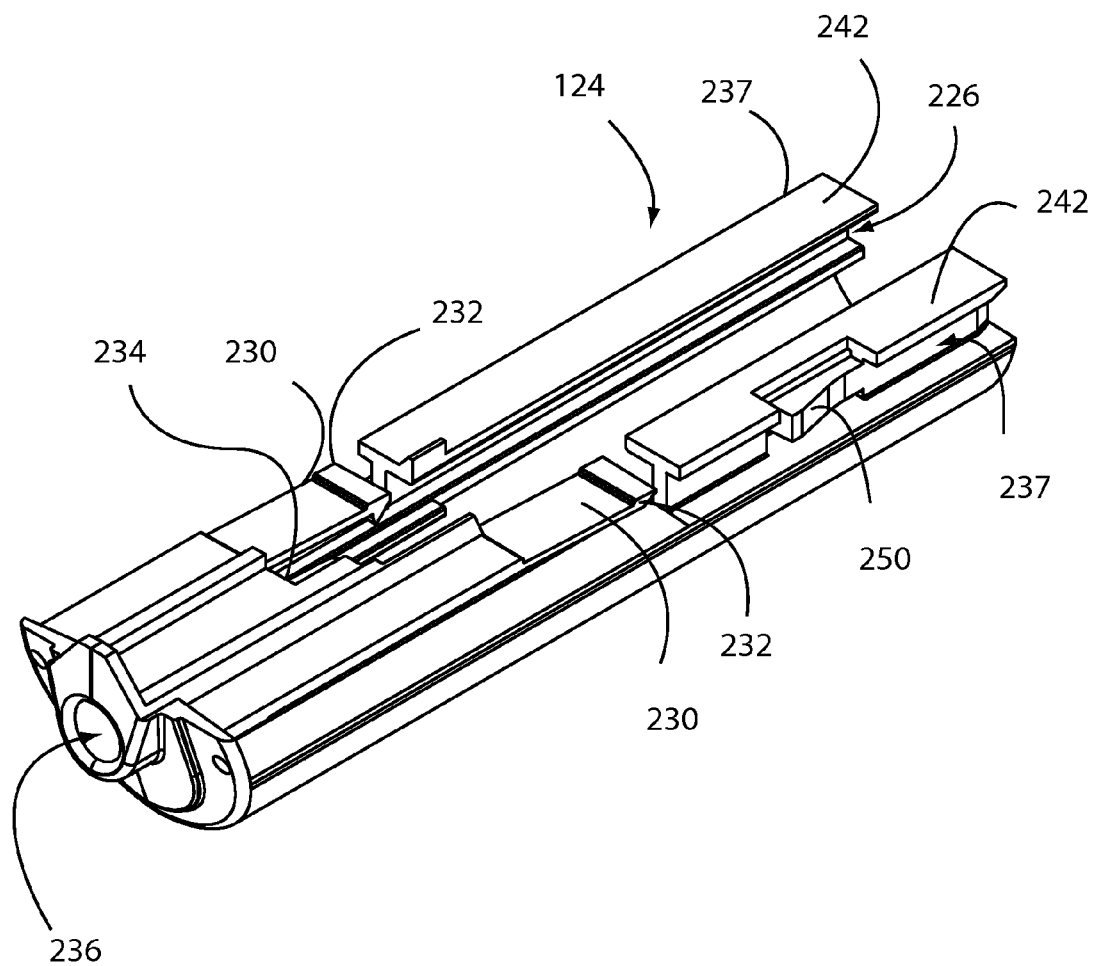
FIG. 22 is a perspective view of a cartridge.
Figure 23:
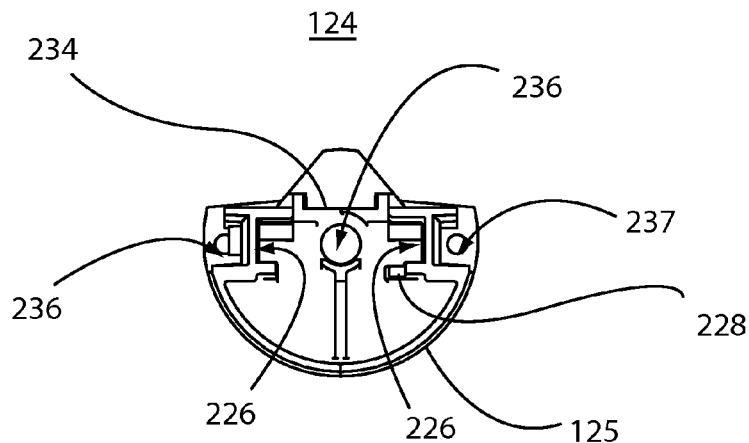
FIG. 23 is an end view of the cartridge of FIG. 22.
Figure 24:
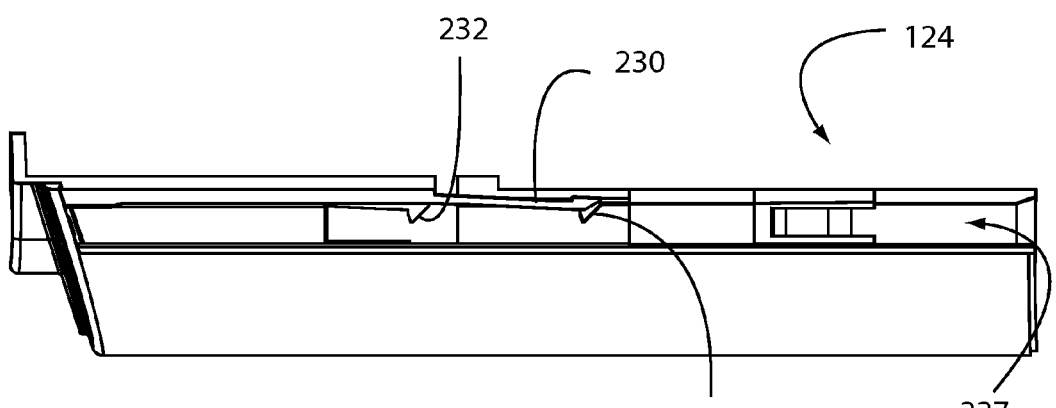
FIG. 24 is a cross-section side view of the cartridge of FIG. 22.
Figure 27:
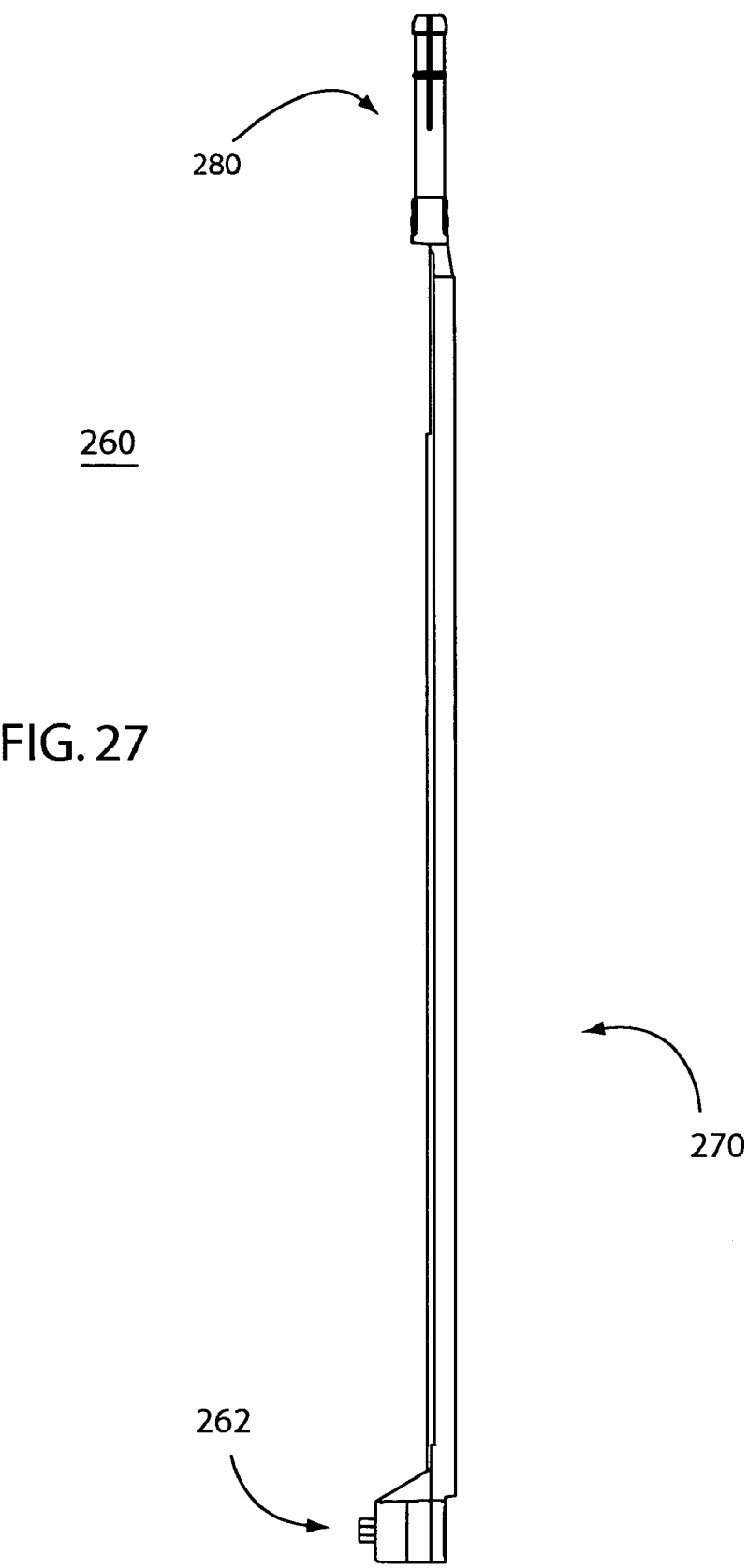
FIG. 27 is a side view of the expander of FIG. 25, including the expander tip of FIG. 28A at its distal end.

Referring to FIGS. 22-24, the crown 200 is slidably connected to the cartridge 124. The cartridge 124 includes an outer shell 125 and a substantially hollow interior into which one or more structures are formed. The cartridge 124 is composed of the same material as the casing 98, and is manufactured in the same way. Alternately, the. cartridge 124 may be composed of a different material and/or manufactured differently. At least one groove 226 is defined within the interior of the cartridge 124. The groove or grooves 226 extend substantially axially, wherein the axial direction is defined relative to the mated position of the cartridge 124 within the integrated tool 100. Each groove 226 is configured to receive at least one flange 222 of the interface 214 of the crown 200, and to allow the received flange or flanges 222 to slide within it. The groove or grooves 226 are positioned within the cartridge 124 relative to the outer shell 125 to provide adequate space within the cartridge 124 for the interface 214 and other components of the crown 200 to slide freely within the cartridge 124. A stop 228 is defined within the cartridge 124. The tab 224 connected to the interface 214 of the crown 200 is configured to engage the stop 228. In this way, the stop 228 acts to restrict the proximal motion of the tab 224 and provides a positive stop for crown 200 placement when the cartridge 124 is inserted into the casing 98. In this way, the initial axial position of the crown 200 is positively identified.

The cartridge 124 also includes one or more flexures 230. The flexures 230 are molded or otherwise formed into the cartridge 124. A wedge 232 or similar element is located at the distal end of each flexure 230, directed upward. The wedge 232 is biased upward into the corresponding groove 226 by the flexure 230. One flexure 230 and corresponding wedge 232 are positioned in one of the grooves 226 such that the space between the wedge 232 and the upper surface of that groove 226 is less than the height of the flange 222 of the crown 200. The other flexure 230 and corresponding wedge 232 are positioned in the other groove 226 such that the space between the wedge 232 and the upper surface of that groove 226 is less than the thickness of the flange 266 of the expander 260 and the flange 222 of the crown 200. The wedges 232 thus hold the flanges 222, 266 within the cartridge 124 before the cartridge 124 is loaded into the casing 98. Alternately, only one flexure 230 and wedge 232 are used, thus directly restraining only one of the flanges 222, 266.

The cartridge 124 may also includes at least one stop 234 configured to engage the tab 224, in order to limit the proximal motion of the crown 200 and expander 260. A passage 236 is defined through the cartridge 124 in order to receive a graft vessel therethrough. The passage 236 is substantially aligned with the axis of the crown 200. Thus a graft vessel can be pulled through the passage 236, the crown collar 202, the crown body 212 and the semicircular recess 216 of the crown 200.

Referring also to FIGS. 1 and 14-15, the cartridge 124 is connected to the casing 98. The cartridge 124 includes at least one outer groove 237. Each outer groove 237 is substantially parallel to the other, and to the inner grooves 226. Alternately, the outer grooves 237 are not parallel to the inner grooves 226. The outer grooves 237 are substantially parallel to one another, and to the inner grooves 226. The cartridge 124 is connected to the casing 98 by sliding each outer groove 237 over a corresponding rail 238 defined in each case half 120,122. The rails 238 guide the motion of the cartridge 124 as it is installed onto the casing 98. A feature 239 is provided in the casing 98 adjacent one or more of the rails 238, where that feature 239 is configured to engage a wedge 232 in the cartridge 124 and bias it out of the groove 226. Thus, the flange or flanges 222, 266 previously restrained by the wedge 232 and corresponding flexure 230 are free to translate along the corresponding groove 226.

A ridge 240 may additionally be defined in each case half 120, 122, such that a ledge 242 located above each outer groove 237 that in part defined as the outer groove 237 and/or inner groove 226 contacts and rides along the ridge 240. The use of the ridge 240 in conjunction with a rail or rails 248 provides for additional guidance of the cartridge 124 as it is inserted into the casing 98. The cartridge 124 includes at least one locking flexure 250 for engaging the casing 98. Each locking flexure 250 extends into an outer groove 237 of the cartridge 124, and extends outward into the outer groove 237 at its proximal end. The locking flexure 250 is flexed inward while the cartridge 124 is slid onto the casing 98, and engages a recess 252 on the corresponding case half 122 when the cartridge 124 has been completely slid onto the casing 98. The recess 252 may instead be a slot, tab, or other structure adapted to engage the locking flexure 250. When the cartridge 124 has reached the end of its travel along the rail or rails, the locking flexure 250 is positioned relative to the recess 252 such that its proximal end can move into the recess 252. Substantial proximal motion of the cartridge 124 is then restricted, because interference between the locking flexure 250 and the recess 252 prevents such motion.

Referring to FIGS. 28A and 25-31, an expander 260 couples to the crown 200 and extends through the crown collar 202. The expander 260 includes an expander interface 262 at its proximal end. A fourth cam follower 264 extends outward from the expander interface 262. The fourth cam follower 264 is configured to engage a fourth cam path 221 defined in the cam cylinder 70. One or more flanges 266 also extend from the expander interface 262. Referring also to FIG. 22, one or more flanges 266 are configured to engage the inner groove 226 of the cartridge 124. Thus, the flanges 266 translate along the inner groove 226 in the same manner as the flanges 222 of the crown of 200. The expander interface 262 also includes a passage 268 defined therethrough. This passage 268 allows a graft vessel to pass through the expander interface 262. An expander body 270 extends distally from the expander interface 262. The expander body 270 is shaped similar to the crown body 212 of the crown 200. The expander body 270 is a half-tubular structure having a substantially semicircular cross-section. The expander body 270 includes a rail 272 extending substantially axially along, and at a distance inward from, at least one edge of the expander body 270. Thus, a ledge 274 is formed between each edge of the expander body 270 and the corresponding rail 272. The rail 213 of the crown 200 is configured to be received adjacent to the ledge 274 of the expander body 270 and outward from the rail 272. Thus, each rail 272 of the expander body 270 is positioned adjacent to the corresponding rail 213 of the crown body 212. Where two rails 213, 272 are used on both the expander body 270 and the crown body 212, the rails 213, 272 register the expander 260 to the crown 200 such that the expander body 270 and the crown body 212 together form a substantially tubular structure having a hollow lumen. Further, the use of the rails 213, 272 allows the expander body 270 to translate axially relative to the crown body 212 while maintaining axial registration therebetween. In this way, the rails 213, 272 guide and stabilize the motion of the expander 260 relative to the crown 200.

Figure 28:
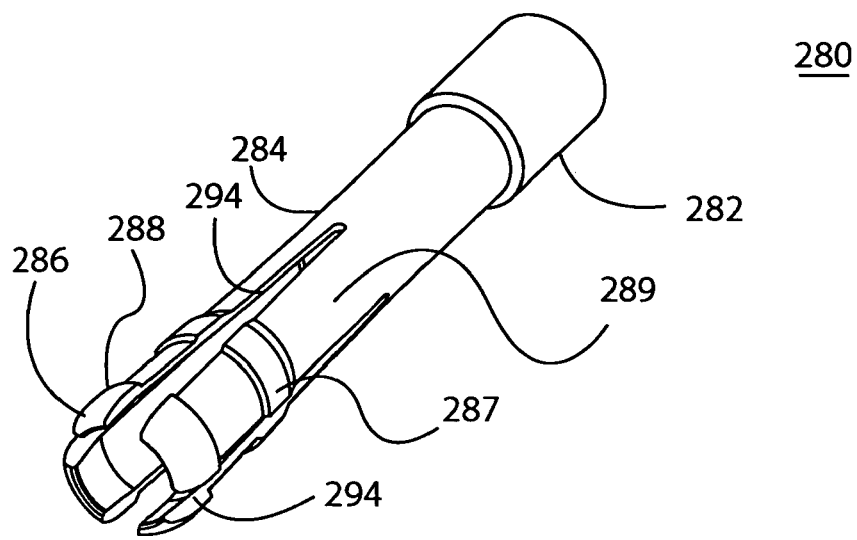
FIG. 28 is a perspective view of an expander tip at the distal end of the expander of FIG. 25.
Figure 29:
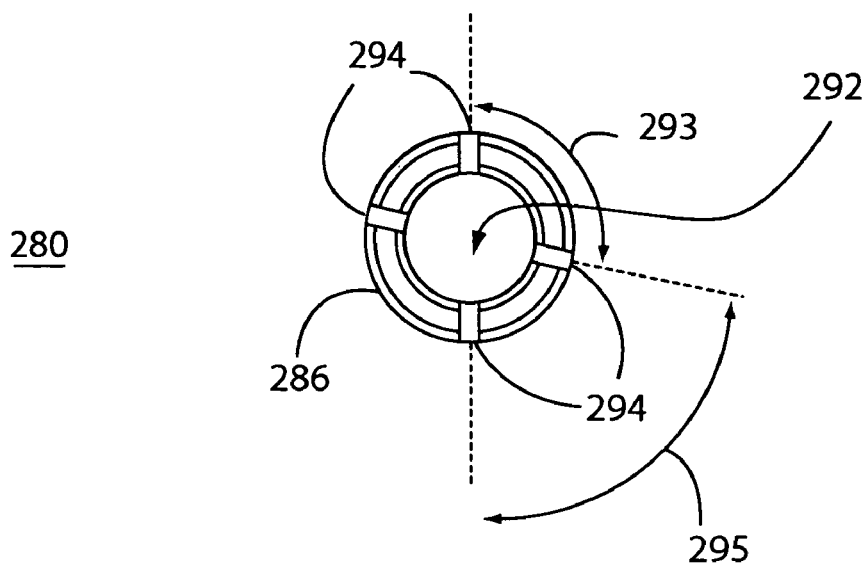
FIG. 29 is a side view of the expander tip of FIG. 28.
Figure 30:
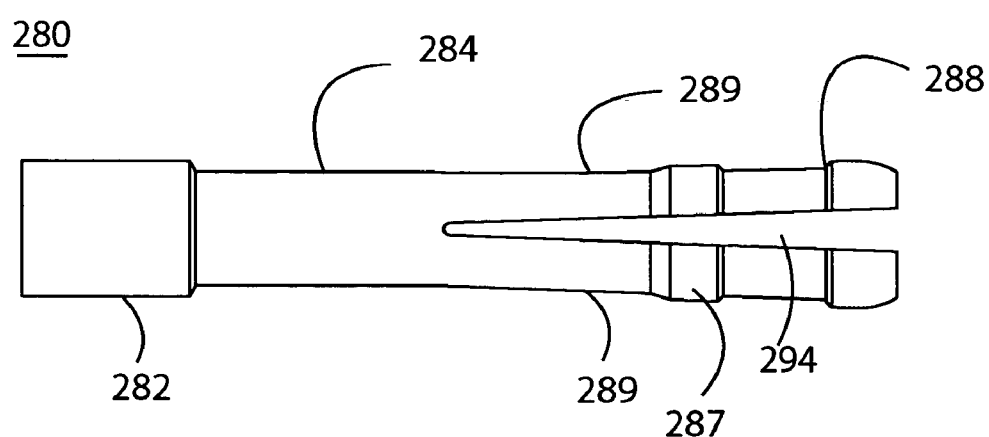
FIG. 30 is an end view of the expander tip of FIG. 28.
Figure 31:
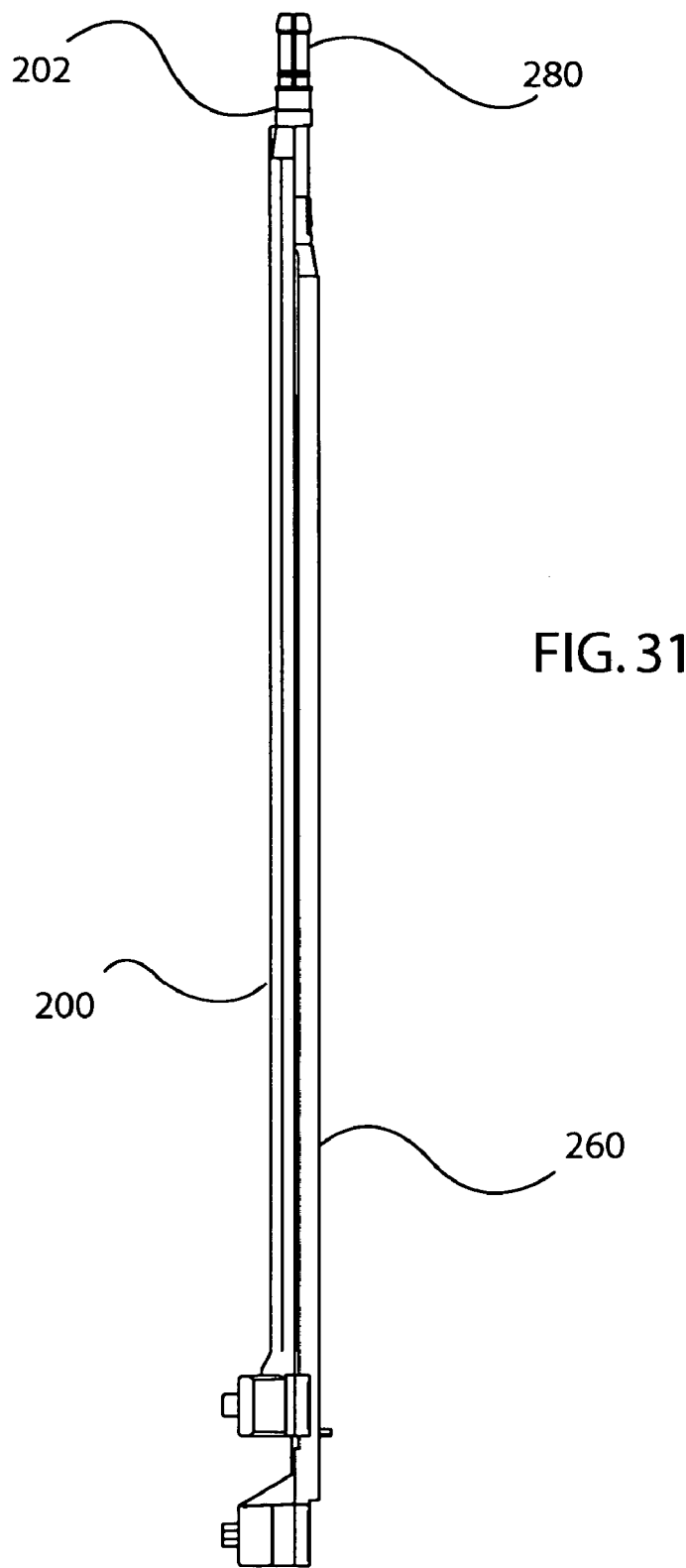
FIG. 31 is a side view of the crown and expander fitted together.

An expander collar 276 is connected to the distal end of the expander 260. The expander collar 276 is narrower than the expander body 270. Alternately, the expander collar 276 may have a different diameter. Referring also to FIGS. 28-30, an expander tip 280 is connected to the expander collar 276. Alternately, the expander collar 276 is not used, and the expander tip 280 is connected directly to the expander body 270. The expander tip 280 is formed from hardened stainless steel, and includes a thin cylindrical shell 282 at its proximal end. The expander collar 276 is also substantially cylindrical, and has a diameter slightly smaller than the inner diameter of the shell 282 at the proximal end of the expander tip 280. The expander tip 280 is connected to the expander collar 276 by placing the shell 282 over the expander collar 276 and dimpling it to fix it to the expander collar 276. That is, a force is applied to one or more points on the shell 282, causing it to dimple, such that the bottom of the dimple digs into the expander collar 276 to hold the shell 282 and the expander collar 276 together. Alternately, the expander tip 280 may be connected to the expander collar 276 in a different way, such as by the use of locking tabs, adhesives, threading, or insert molding, or by other structures, mechanisms, or methods.

The expander collar 276 is positioned proximally to the crown collar 202. Further, the expander collar 276 is substantially coaxial with the crown collar 202. The expander tip 280 extends distally from the expander collar 276 through the crown collar 202. The body 284 of the expander tip 280 is substantially cylindrical, and has a smaller diameter than the shell 282. The body 284 is sized to fit snugly against, while sliding free from interference with, the inner diameter of the crown collar 202. Thus, the body 284 of the expander tip 280 can translate through the crown collar 202 upon the application of a force at or above a preselected level. Further, the snug fit between the inner diameter of the crown collar 202 and the body 284 of the expander tip 280 assists in providing hemostasis relative to the seal chamber 34, because the fit is snug enough to prevent substantial motion of fluid between them. The outer diameter of the shell 282 is smaller than the inner diameter of the crown body 212, such that the shell 282 can be received into the crown body 212 and translate relative to it.

Figure 28A:
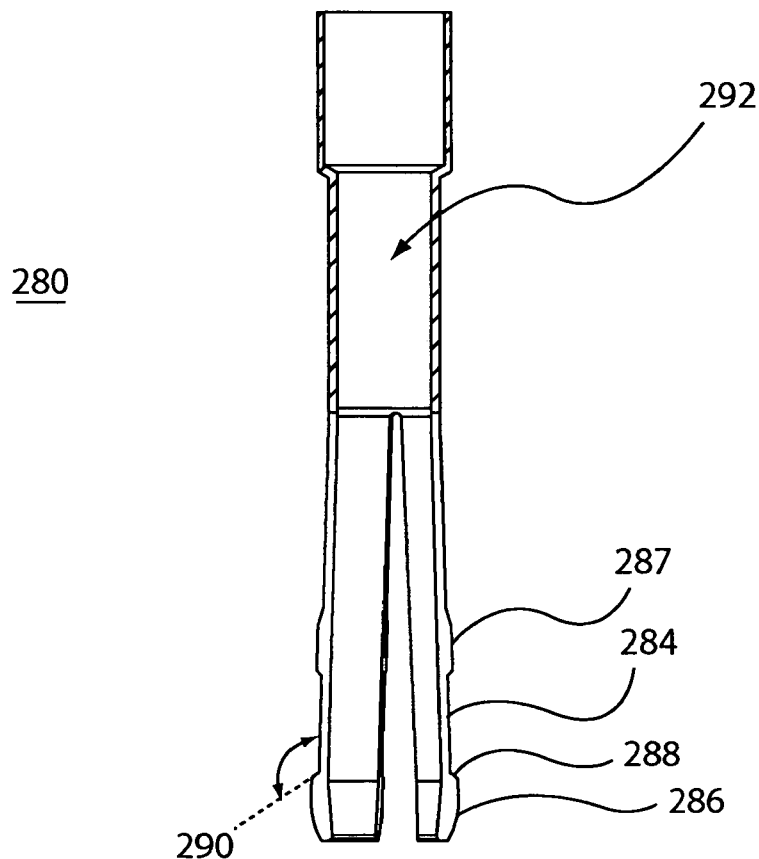
FIG. 28A is a side cross-section view of the expander tip of FIG. 28.

The expander tip 280 also includes an expander head 286 and an expander collet 287. Both the expander head 286 and the expander collet 287 have a larger diameter than the expander body 284, and extend substantially circumferentially around the expander tip 280. The expander head 286 is smoothly tapered from its distal end to its proximal end. Referring in particular to FIG. 28A, the expander head 286 includes a shoulder 288 at its intersection with the body 284 of the expander tip 280. The shoulder 288 forms an angle 290 with the surface of the body 284 of the expander tip 280. This angle 290 is substantially 95 degrees. However, a different angle 290 may be utilized, if desired. The angle 290 is substantially the same around the entire expander tip 280. However, the angle 290 may vary in different locations around the expander tip 280. A lumen 292 extends through the expander tip 280, where that lumen 292 is substantially coaxial with the crown collar 202 and with the expander collar 276. The lumen 292 may itself taper to a smaller diameter toward the distal end of the expander head 286. This tapering acts to protect the graft vessel as it is pulled through the lumen 292. The tines 196 of the anastomosis device 140 are located distal to the distal end of the lumen 292. By tapering the lumen of the expander tip 280 to direct the graft vessel inward away from the tines 196 before that graft vessel is everted over them, the graft vessel is protected. The collet 287 is substantially circumferential around the expander tip 280, and is located proximal to the expander head 286. The collet 287 has a larger diameter than the body 284 of the expander 280. The collet 287 and the expander head 286 are translated relative to the crown 200 to deploy the anastomosis device 140 into a vessel wall, as is described in greater detail below.

The expander tip 280 includes slots 294 defined therein. The slots 294 extend substantially axially from the distal end of the expander tip 280 through the expander head 286 and collet 287, extending proximally to the collet 287. The segments 289 of the expander tip 280 between the slots 294 are each biased outward relative to the axis of the expander tip 280, as may be seen most clearly in FIG. 28A. Alternately, the segments 289 are not biased outward relative to the axis of the expander tip 280. The slots 294 allow these segments 289 of the expander tip 280 to move inward toward the axis of the expander tip 280 at a point in the deployment of the anastomosis device 140 to allow the expander tip 280 to move proximally to the deployed anastomosis device 140. Thus, the slots 294 are sized to allow the segments 289 to move close enough to one another to allow the expander tip 280 to move proximally to the deployed anastomosis device 140. The outward force generated by the expander tip 280 acts to substantially center the anastomosis device 140 on the expander tip 280 during deployment, such that the axis of the anastomosis device 140 remains substantially coaxial with the axis of the expander tip 280.

Referring particularly to FIG. 29, the slots 294 are not spaced evenly along the circumference of the expander head 286. Four slots 294 are used, where each slot 292 is separated by a major angle 293 and a minor angle 295 from the slots adjacent to it. The major angle 293 is substantially 103°, and the minor angle 295 is substantially 77°. These angles 293, 295 may be different, if desired. Thus, each segment 289 of the expander tip 280 has one of two different sizes. As a result, two segments 289 are larger than the other two segments, and therefore are stiffer than the smaller segments 289. Referring also to FIG. 1, the expander tip 280 advantageously is oriented relative to the contact structure 110 on the casing 98 such that the segments 289 that are less stiff than the other segments 289 are substantially aligned with each other and with the opening in the perimeter of the contact structure 110. This facilitates the removal of the integrated anastomosis tool 100 from an anastomosed graft vessel.

The segments 289 of the expander tip 280 between the slots 294 are each biased outward relative to the axis of the expander tip 280, as may be seen most clearly in FIG. 28A. This outward bias assists in deployment of the anastomosis device 140, as is described in greater detail below. Alternately, the segments 289 of the expander tip 280 between the slots 294 are not biased outward relative to the expander tip 280. Alternately, a ring (not shown) may be provided between the collet 287 and the expander head 286, or may be provided instead of the collet 287. The ring slides freely relative to the expander tip 280, and is used to compress the segments 289 toward the axis 143 of the anastomosis device 140 at the appropriate point in the deployment process.

Referring to FIG. 9, the knob 88 includes a recess 89. The recess 89 is positioned relative to the cam cylinder 70 such that the cartridge 124 can only be inserted into the casing 98 when the knob 88 is in the correct starting position. The cartridge 124 slides into the casing 98 substantially linearly, as described above. The interfaces 214, 262 of the crown 200 and the expander 260 slide through the recess 89 when the knob 88 is in the correct starting position. If the knob 88 is at another position, it will interfere with the 214, 262 of the crown 200 and the expander 260, preventing insertion of the cartridge 124. The user must then rotate the knob 88 to the correct starting position before inserting the cartridge 124 into the casing 98.

Figure 36:
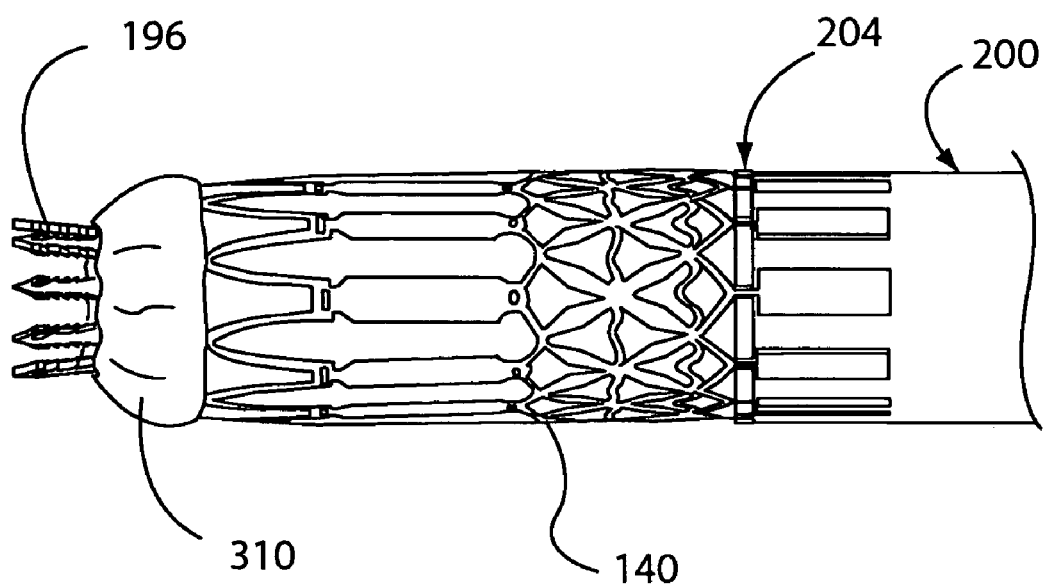
FIG. 36 is a side view of the anastomosis device before deployment, showing a graft vessel everted over its distal end.

When the cartridge 124 is inserted into the casing 98, the crown 200 and the expander 260 are connected to the cartridge 124 and held relative to it by the flexures 230 and wedges 232 described above. Referring also to FIG. 36, a graft vessel 310 has been pulled through the passage 236 and the combined bodies of the expander 260 and the crown 200, and has been everted over the anastomosis device 140 at the distal end of the crown 200. The crown body 212 and the expander body 270 together form a substantially cylindrical body having an outer diameter slightly less than the inner diameter of the introducer tube 62. The crown body 212 and the expander body 270 are slidable within the lumen of the introducer tube 62. In this way, the introducer tube 62 can support and guide the crown 200 and expander 260 during their translation. Further, the close fit between the inner surface of the introducer tube 62 and the outer surface of the crown body 212 and the expander body 270 substantially seals the introducer tube 62 relative to the seal chamber 34, such that fluid in the seal chamber 34 does not substantially leak out of the seal chamber 34 between the introducer tube 62 and the crown 200 or expander 260. A separate seal may be provided between the introducer tube 62 and the seal chamber 34 if desired.

One or more features may be provided within the integrated anastomosis tool 100 to prevent premature deployment. Referring to FIGS. 6, 11, 38A-D, and 40, a notch 400 may be defined in the cam cylinder 70. The notch 400 extends in a direction substantially perpendicular to the axis of the cam cylinder 70. The cam cylinder 70 is biased proximally by a spring (not shown) or other component or mechanism. A stop 402 corresponding to the notch 400 is defined on the inner surface of the casing 98. The stop 402 is oriented substantially perpendicular to the axis of the cam cylinder 70. The cam cylinder 70 is initially positioned such that the notch 400 is biased against the stop 402 before the cartridge 164 is loaded into the casing 98. The notch 400 is shaped such that its contact with the stop 402 substantially prevents rotational motion of the cam cylinder 70.

Referring also to FIGS. 14, 15, 22-24, and 25-26, when the cylinder 164 is loaded into the casing 98, the tab 224 of the crown 200 engages the stop 228 in the cartridge 164, thereby restraining the crown 200 and the expander 260 against proximal motion. The crown 200 and the expander 260 thus move distally along with the cartridge 164. The cam followers 264, 218 of the expander 260 and the crown 200 are impelled forward in the third and fourth cam paths 220, 221. The third cam path 220 includes a bend 404 that the cam follower 218 of the crown 200 encounters upon loading of the cartridge 164. The bend 404 is at substantially 45 degrees to the axis of the cam cylinder. Because the expander 260 and crown 200 are constrained against proximal motion by the cartridge 164, the cam follower 218 of the crown 200 pushes the cam cylinder 70 forward and rotates it as it encounters the bend 404. The forward motion of the cam cylinder 70 acts against the proximal bias of the cam cylinder 70, causing the notch 400 to disengage from the stop 402. Further, the rotational motion of the cam cylinder 70 causes the notch 400 to rotate relative to the stop 402, such that the cam cylinder 70 can no longer move proximally to seat against the stop 402. The cam cylinder 70 is thus free to rotate.

A safety switch 296 may be provided on the integrated anastomosis tool 100. The safety switch 296 engages a fifth cam path 298 defined in the cam cylinder 70 with a cam follower (not shown) or other engagement structure. The fifth cam path 298 is defined in the cam cylinder 70 such that the knob 88 cannot be rotated substantially until the safety switch 296 is moved to a position in which the cam follower allows the cam cylinder 70 to move. The remainder of the fifth cam path 298 lies substantially in a plane perpendicular to the axis of the introducer tip 28, such that the cam cylinder 70 may then rotate freely. The safety switch 296 is optional, and may be omitted.

The integrated tool 100 is operated to insert the anastomosis device 140 into the opening in the vessel wall and deploy it. After the auger 6 and cutter 4 have removed tissue from the vessel wall, they are retracted off-axis from the introducer tip 52, as described above. The introducer tip 52 is thereby open, such that the anastomosis device 140 can be advanced through it. The combination of the crown body 212 and the expander body 270 forms a tube that is substantially coaxial with the axis of the introducer tip 52. Thus, the crown 200, the anastomosis device 140 connected to the distal end of the crown 200, and the expander 260 can be translated distally into the introducer tip 52. Alternately, the auger 6 and the cutter 4 retract tissue substantially along the axis of the introducer tip 52, and the crown 200, anastomosis device 140 and expander 260 are translated off-axis to the axis of the introducer tip 52 for passage through it.

Referring to FIG. 36, a graft vessel 310 is pulled through the expander 260 and the crown 102 and everted over the tines 196 of the anastomosis device. The graft vessel 310 thus extends through the lumen 292 of the expander tip 280, and proximally through the combined expander body 270 and crown body 212. Thus, no components of the integrated anastomosis tool 100 extend into the lumen of the graft vessel 310.

Initially, the distal end of the expander tip 280 is located within the anastomosis device 140, proximal to the curved portion of the linkage 182. This relative positioning is controlled by the third and fourth cam paths 220, 221 and associated cam followers 218, 264. The third and fourth cam paths 220, 221 are also configured to prevent the crown 200, the anastomosis device 160 and the expander 260 from interfering with the auger 6, the cutter 4, the bushing 38, or any other component of the integrated anastomosis tool 100 used for creating an opening in the vessel wall. The third and fourth cam paths 220, 221 are configured to translate the crown 200, the anastomosis device 140 and the expander 260 distally as the opening is made in the vessel wall. Alternately, the crown, anastomosis device 140 and expander 260 are not translated distally until after the opening has been made in the vessel wall.

The distal end of the expander head 286 is initially located substantially adjacent to the ring 183 of the linkage 182. As described above, the segments 289 of the expander tip 280 between the slots 294 are biased outward. These segments 289 of the expander tip 280 are configured to exert radial force on the anastomosis device 140 while the expander tip 280 is in its initial position. The ring 183 of the linkage 182 counteracts that radial force, preventing deformation of the linkage 182 and the anastomosis device 140.

After creating the opening in the vessel wall, the user continues to turn the knob 88. The third and fourth cam paths 220, 221 cause the expander 260 and the crown 200 to translate toward that opening through the introducer tube 62 into the seal housing 34, because the third cam follower 218 connected to the crown 200 rides within the third cam path 220, and the fourth cam follower 264 connected to the expander 260 rides within the fourth cam path 221. The third cam follower 218 is restrained to move substantially linearly in a direction substantially parallel to the axis of the introducer tube 62, and the fourth cam follower 264 is restrained to move substantially linearly in a direction substantially parallel to the axis of the introducer tube 62. Rotation of the cam cylinder 70 causes the cam paths 220, 221 to move relative to the cam followers 218, 264, thereby causing the cam followers 218, 264 to translate axially, or holding them stationary in the axial direction. Alternately, the distal ends of the expander 260 and the crown 200 are already located within the seal housing 34 after the opening is created in the wall of the target vessel.

The third and fourth cam paths 220, 221 are substantially parallel, such that the crown 200 and the expander 260 translate at substantially the same rate, and maintain substantially the same distance with regard to each other during this translation. The anastomosis device 140 is not substantially tensioned or compressed at this time. The distal end of the anastomosis device 140 enters the opening. The tines 196 enter the lumen of the vessel. The third and fourth cam paths 220, 221 are configured such that crown 200 and the expander 260 move the distal ends of the tines 196 a preselected amount relative to the distal end of the contact structure 110. Thus, by measuring the diameter of the vessel in advance, it can be determined whether the lumen of the vessel is large enough to receive the anastomosis device 140, because the maximum distance between the distal ends of the tines 196 and the distal end of the contact structure 110 is known. As the tines 196 enter the opening in the target vessel wall, a portion of the everted graft vessel is brought into contact with the walls of the opening. Because the graft vessel has been everted, the inner layer of the graft vessel is thus in contact with the inner layer of the target vessel after the anastomosis device 140 is deployed. Where the anastomosis surgery is a CABG procedure, this results in intima-to-intima contact between the graft vessel and the target vessel.

As the knob 88 continues to rotate, the third cam path 220 restrains the crown 200 in the axial direction, while the fourth cam path 221 causes the expander 260 to translate distally through the crown collar 202. The rotary force on the knob 88 that is transmitted to the expander 260 via the cam cylinder 70 and third cam path 220 is sufficient to move the body 284 of the expander tip 280 through the crown collar 202. Distal translation of the expander 260 causes the expander tip 280 to translate distally relative to the anastomosis device 140, which is connected to the crown 200. The expander head 286 thus encounters the ring 183 of the linkage 182. The expander head 286 is smoothly curved, such that it encounters the ring 183 and expands it radially outward without catching on the ring 183.

The ring 183 includes a number of expandable elements 141, where each expandable element 141 connects two adjacent tines 196. The expandable elements 141 are curved, where the curve has a component in the axial direction. As the ring 183 translates distally into the ring 183, the ring 183 expands radially, because the diameter of the expander head 286 is wider than the diameter of the ring 183. That is, the axial motion of the expander head 286 causes hoop stress in the ring 183, and the expandable elements 141 deform and lengthen under the influence of this hoop stress.

The ring 183 also expands both axially and radially as a result of its contact with the expander head 286 during axial motion of the expander head 286. That is, each point on the ring 183 is moved both axially in the distal direction, and away from the axis 143 in the radial direction, by contact with the expander head 286, as a consequence of the shape and size of the expander head 286. The expandable elements 141 are long enough to allow radial expansion of the ring 183 without a resultant axial compression of the ring 183. The expandable elements 141 are configured to deform and lengthen a sufficient amount under the influence of hoop stress in the ring 183 to allow the ring 183 to expand radially without causing an associated axial compression. That is, the expandable elements 141 provide the ring 183 with sufficient flexibility such that radial expansion of the ring 183 does not result in axial compression of the ring 183. The expander head 286 additionally pushes the elements of the ring 183 distally, causing expansion in the axial direction. Thus, axial expansion of the deployable section 142 accompanies radial expansion of the deployable section 142. As a result, the distance between the tines 196 and the outer flange arms 174 increases as the ring 183 expands radially. The portion of the linkage 182 proximal to the ring 183 substantially does not expand radially, because it is already at least as far from the axis 143 as the widest part of the expander head 286.

Figure 32:
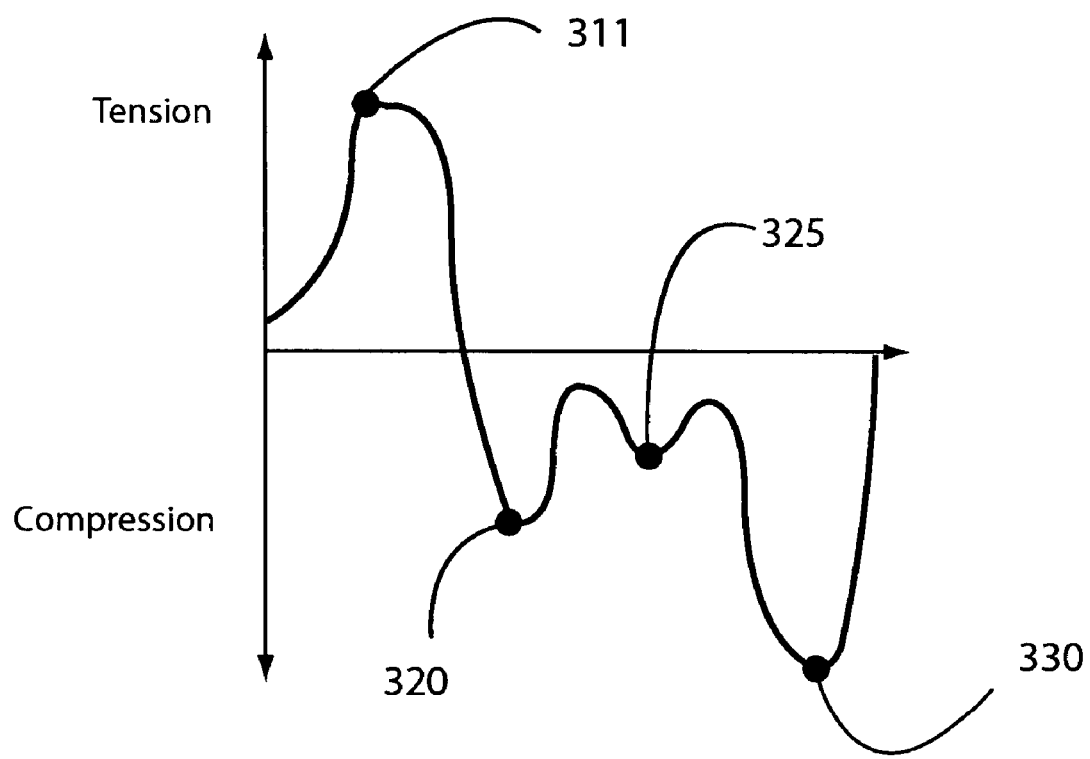
FIG. 32 is a graph of force applied to the deployable section of the anastomosis device over time.

Referring also to FIG. 16, the distal translation of the expander tip 280 causes the expander head 286 to exert tensile force on the anastomosis device 140. This tension causes expansion of the linkage 182. This expansion causes the intersections between each tine 196 and the linkage 182 to expand radially outward from the axis 143 of the anastomosis device 140, thereby moving the tines 196 away from one another. Referring to FIG. 32, a qualitative graph of the force exerted on the anastomosis device 140 over time is shown. As shown in FIG. 32, the tension in the anastomosis device 140 increases as the knob 88 is rotated.

As the expander head 286 translates distally, it contacts the horn or horns 186 associated with each tine 196. The horns 186 extend toward the axis 143 of the anastomosis device 140. As the expander head 286 encounters the horns 186, it exerts a force distally on the horns 186. The horns 186 are initially angled relative to the axis 143, and advantageously are substantially perpendicular to the axis 143. Thus, the axial motion of the expander head 286 exerts an axial force on the horns 186, causing the horns 186 to rotate to a position substantially parallel to the axis 143. The tines 196 are connected to and substantially perpendicular to the horns 186. The rotation of the horns 186 causes the tines 196 to rotate away from the axis 143, such that they move to an angle pointing away from the axis 143. The curvature of the expander head 286 as well as the position and shape of the ring 183 are chosen to result in the desired angle relative to the axis 143 upon deployment.

Referring as well to FIGS. 34-35, at the point of maximum tension 311, the tines 196 have been fully deployed to form an inner flange 300. In this fully-deployed position, each tine 196 forms an angle of substantially ninety degrees with the axis 143 of the anastomosis device 140. Alternately, the tines 196 form a different angle with the axis 143 of the anastomosis device 140. Alternately, one or more tines 196 form a different angle with the axis than one or more other tines 196. Upon full deployment of the inner flange 300, the segments 289 of the expander tip 280 are freed to spread outward away from the axis 143, because the inner diameter of the inner flange 300 is larger than the largest outer diameter of the expander head 286.

At this time, the inner flange 300 is located in the lumen of the target vessel, spaced apart from the inner wall of the target vessel. The user continues to rotate the knob 88. The third and fourth cam paths 220, 221 cause both the crown 200 and the expander 260 to translate proximally at substantially the same rate, such that the crown 200 and the expander 260 remain substantially the same distance from each other. The proximal translation of the crown 200, which is connected to the anastomosis device 140, causes the anastomosis device 140, and hence the inner flange 300, to translate proximally. During this translation, the inner flange 300 comes into contact with the inner wall of the target vessel, and seats against the inner wall of the target vessel.

The inner flange 300 has thus reached its deployed position relative to the inner wall of the target vessel. The inner flange 300 holds the distal end of the graft vessel 310 against the edges of the opening in the vessel wall. The linkage 182 forms a body 302 that extends through the opening in the vessel wall. The body 302 holds at least part of the everted portion of the graft vessel 310 against the walls of the opening. Referring in particular to FIG. 16, the portion of the linkage 182 proximal to the ring 183 and proximal to the expandable members 184 does not expand radially or axially during deployment of the inner flange 300. This portion of the linkage 182 initially has the same diameter as its deployed diameter, and initially has the same axial length as its deployed distal length.

Figure 33:
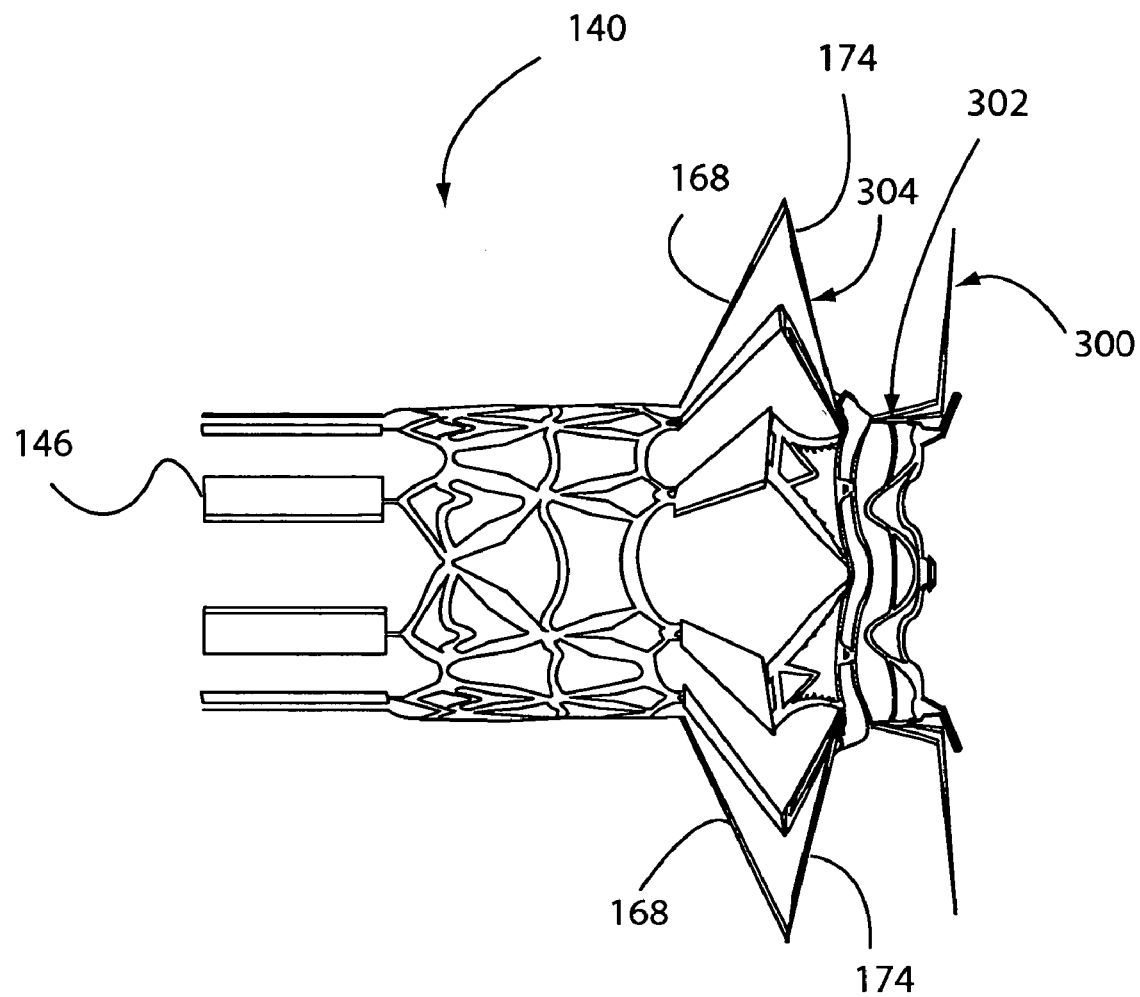
FIG. 33 is a side view of the anastomosis device partially deployed.

The operator continues to rotate the knob 88. The third and fourth cam paths 220, 221 are configured to hold the expander 260 in substantially the same axial position and to translate the crown 200 distally. This relative axial motion between the expander 260 and the crown 200 axially compresses the anastomosis device 140, as seen in FIG. 33. Further, the inner surface of the body 302 of the anastomosis device 140 may contact the segments 289 of the expander tip 280, and this contact may at least partly compress the segments 289 toward the axis 143 of the anastomosis device 140. The compressive stress within the anastomosis device 140 increases as the expander 260 continues to translate proximally and the crown 200 continues to translate distally. This compressive stress increases until buckling occurs at the intersections between the spreader arms 168 and the outer flange arms 174. The buckling stress 320 is shown on FIG. 32. Buckling is designed to occur at these intersections as a result of the relationships between the first distance 170, the second distance 178 and the third distance 180. Because the first distance 170 is located radially closer to the axis 143 than the second distance 178, and the third distance 180 is located radially closer to the axis 143 than the second distance 178, an outward moment is produced on the anastomosis device 140 at the second distance 178 as a result of the axial compressive stress exerted on the anastomosis device 140. This outward moment results in an outward force that causes buckling at the intersections between the spreader arms 168 and the outer flange arms 174, such that buckling occurs at those intersections rather than at other locations on the anastomosis device 140.

Referring also to FIG. 33, the spreader arms 168 and the outer flange arms 174 each begin to angle outward from the axis 143 after buckling at the intersections between them, under the effect of the continuing relative motion of the expander 260 and the crown 200. As seen in FIG. 32, the anastomosis device 140 continues to experience compressive stress, but at a lower level than at the point of buckling. The outward bias of the segments 289 of the expander tip 280 acts to axially center the anastomosis device 140 during deployment. Alternately, where the segments 289 are not biased outward, a ring (not shown) may encircle the body 284 of the expander tip 280 between the expander head 286 and the expander collet 287. The spreader arms 168 and outer flange arms 174 spread outward to deploy the outer flange 304, which is formed from the outer flange elements 173. The ring translates distally along the body 284 of the expander tip 280, urged in this direction by contact with the distal end of the crown 200. Distal motion of the ring causes the segments 289 to move radially. Thus, the crown 200 compresses the segments 289 with the ring.

As rotation of the knob 88 continues, the hinging motion between the outer flange arms 174 and the spreader arms 168 continues. This hinging motion is driven by the relative motion of the expander 260 and the crown 200. Compressive stress at the intersections between the outer flange arms 174 and the spreader arms 168 decreases as the outer flange arms 174 and the spreader arms 168 continue to rotate. The intersections between the spreader arms 168 and the outer flange arms 174 reach their fracture point at a point in their relative rotation, causing the outer flange arms 174 to separate from the spreader arms 168.

The compression segment 152 of the anastomosis device 140 transmits compressive force to the deployable section 142 of the anastomosis device 140. The compression segment 152 may enter the opening in the target vessel wall during deployment of the anastomosis device 140. As a result, the compression segment 152 acts as a thin spacer for transmitting compressive force. Additionally, the compression segment 152 may acts to extend the axial distance along which compressive stress is applied, in order to prevent premature fracturing between the spreader arms 168 and the outer flange arms 174. The compression segment 152 thus also acts to spread the compression of the anastomosis device 140 out over a longer period of time. In this way, the deployment of the deployable section proceeds smoothly, and the axial forces acting on the deployable section 142 are substantially balanced around its circumference. Alternately, the compression segment 152 is configured differently than described above, and still acts to control the compressive stress in the anastomosis device 140. Alternately, the compression segment 152 is omitted from the anastomosis device 140.

Figure 37:
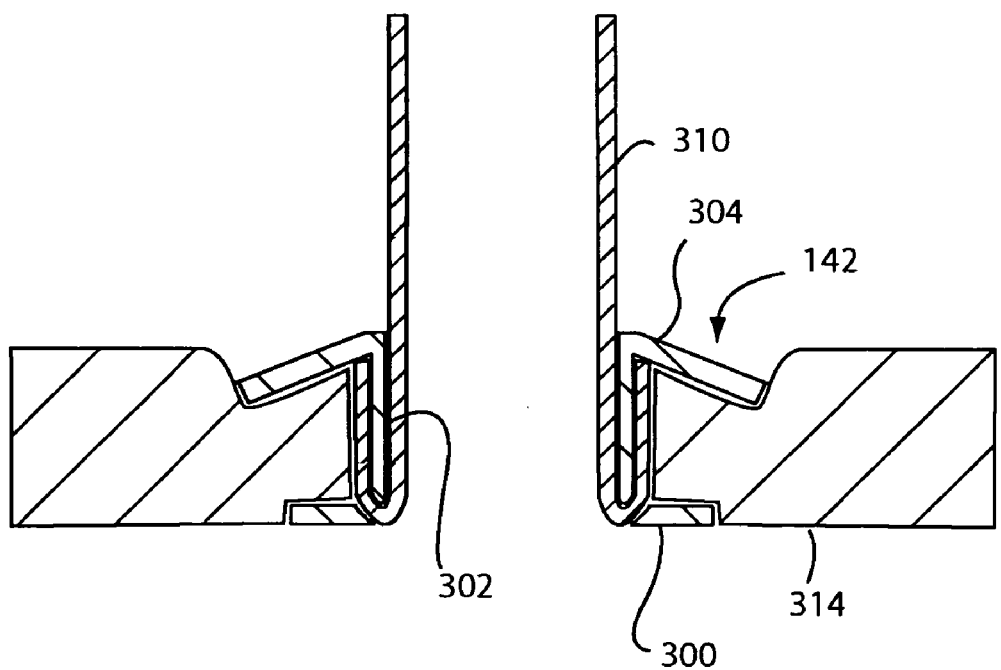
FIG. 37 is a schematic cross-section side view of the anastomosis device after deployment.
Figure 38A:
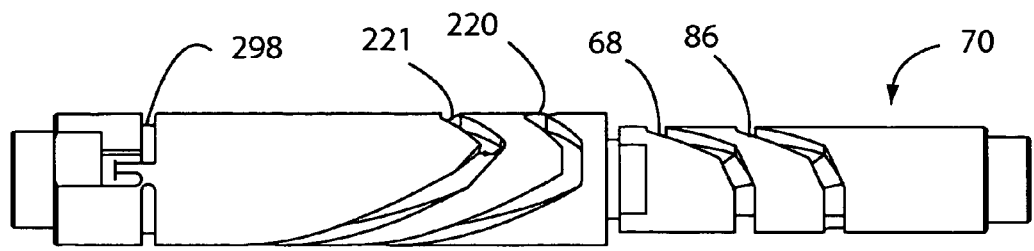
FIGS. 38A-D are four different side views of a cam cylinder, showing the cam paths defined therein.
Figure 38B:
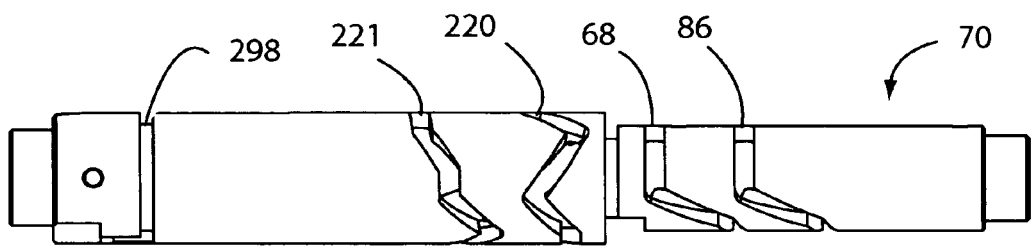
Figure 38C:
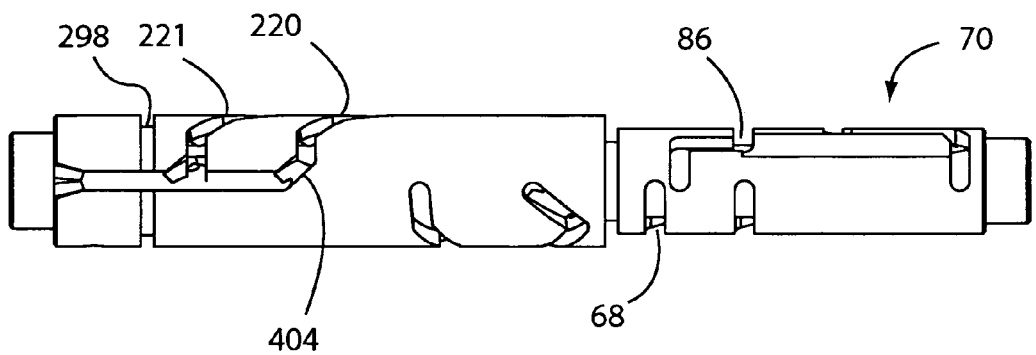
Figure 38D:
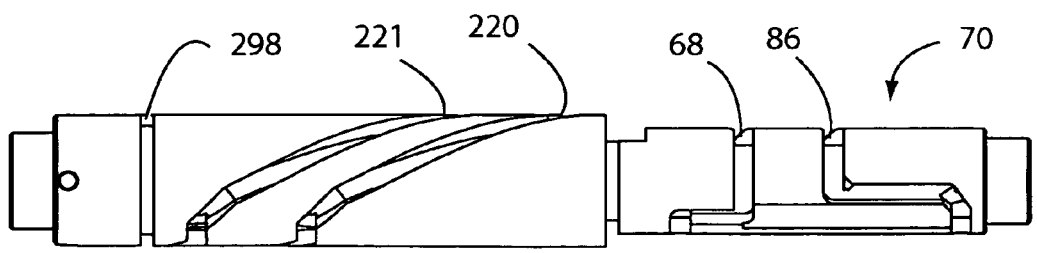

The outer flange 304, and hence the deployable section 142, are free from the discard section 144 of the anastomosis device 140, and therefore free from the integrated anastomosis tool 100 as well. After deployment, the deployable section 142 may be referred to as the implant 142. Referring also to FIG. 37, the outer flange arms 174, in their deployed position, form angles slightly greater than ninety degrees with the axis 143 of the anastomosis device 140, such that the outer flange arms 174 angle toward the outer wall of the target vessel 314 to provide gripping strength. The outer flange arms 174 may form a different angle, if desired. The outer flange arms 174, chevrons 139, and gripping elements 175 grip the outer wall of the target vessel without penetrating it. The deployed outer flange 304 compresses the wall of the target vessel 314 against the inner flange 300. The everted graft vessel 310 is circumferentially positioned against the walls of the opening in the target vessel 314, thereby assisting in sealing the opening and providing for contact between the inner surface of the graft vessel 310 and the inner surface of the target vessel 314. The body 302 may act to press the graft vessel 310 against the walls of the opening in the target vessel 314. The deployed outer flange 304 also grips any portion of the everted graft vessel 310 that may extend outward through the opening in the wall of the target vessel 314, pressing it downward and sealing the edges of the opening. In this way, a positive seal is established, and the implant 142 firmly connects the graft vessel to the target vessel.

Compressive stress continues within the implant 142 after deployment, because the separated spreader arms 168 still exert a compressive force upon the deployed outer flange 304. The expander head 268 is still located distal to the body 302 of the implant 142 after the implant 142 has been deployed. The third and fourth cam paths 220, 221 are configured to translate the expander 260 distally after the implant 142 has separated from the discard section 144. The collet 287 is located at a position on the expander tip 280 such that the collet 287 enters the crown collar 202 shortly after the implant 142 has separated from the discard section 144. The outer diameter of the collet 287 is larger than the inner diameter of the crown collar 202. Thus, when the collet 287 moves into the crown collar 202, the collet 287 contracts, counteracting the outward biasing force exerted by the expander tip 280, and causing the expander tip 280 to radially contract. This radial contraction causes the expander head 286 to contract to an outer diameter substantially equal to the inner diameter of the body 302 of the implant, so that the expander tip 280 can translate distally through the body 302. At the time of colleting 325, the expander collet 287 causes the deployed implant 142 to experience a compressive force. After the expander tip 280 is colleted down, compressive force again increases as the expander tip 280 translates proximally through the deployed implant 142. This compressive force reaches a maximum substantially at the time 300 the expander tip 280 exits the proximal end of the body 302 of the implant 142, then quickly returns to zero as the integrated anastomosis tool 100 is removed from the implant 142. The profile of force over time as shown in FIG. 32 and described above is merely exemplary and qualitative, in order to describe one possible mode of operation of the integrated anastomosis tool 100 and the anastomosis device 140 deployed by that tool. The integrated anastomosis tool 100 and/or the anastomosis device 140 may be configured differently to result in a different force over time profile, if desired.

Alternately, where the collet 287 is not used, the angle of the shoulder 288 is selected to cause deployment of the outer flange of the deployable section 142 and to compress the segments 289 together to allow the expander tip 280 to translate proximally away from the implant 140. In such an embodiment, the angle 290 of the shoulder 288 is substantially 65 degrees, but a different angle could be used. After the expander tip 280 has translated out of the body 302, the anastomosis is complete, and the integrated anastomosis tool 100 can be removed from the target vessel. The contact structure 110 has an open perimeter, so the integrated anastomosis tool 100 can be moved to one side such that the graft vessel can pass through the open portion of the contact structure 110.

As described above, rotation of the knob 88 occurs in a single direction to create an opening in the vessel wall and deploy the anastomosis device 140 into it, in order to simplify operation of the integrated anastomosis tool 100. That is, the knob 88 is rotated clockwise or counter-clockwise relative to the longitudinal axis of the cam cylinder 70. However, the knob 88 and the cam cylinder 70 may be configured such that the knob 88 is rotated sequentially in different directions in order to create an opening in the vessel wall and deploy the anastomosis device 140 into it.

The motion of the expander 260 and crown 200 outside and in proximity to the opening in the target vessel wall takes place within the seal housing 34 in order to maintain hemostasis. As described above, the fit between the inner diameter of the introducer tube 62 and the expander body 270 and the crown body 212 is tight enough to minimize loss of blood through the space between the inner diameter of the introducer tube 62 and the expander body 270 and the crown body 212. Alternately, the seal housing 34 is not provided. Instead, the anastomosis device 140 is slid into the opening in the vessel wall quickly after the opening is made, thereby resulting in minimal blood loss. Alternately, a biocompatible viscous liquid is used to fill gaps between parts, thereby providing hemostasis.

One or more of the components of the integrated anastomosis tool 100 may be lubricated with a lubricious biocompatible substance, such as sodium stearate or another substance. The lubricious substance may be used to coat one or more components of the integrated anastomosis tool 100, or may otherwise be applied to components of the integrated anastomosis tool 100. Advantageously, the cam cylinder 70 is coated with lubricant, such that the cam paths 68, 86, 220, 221 are coated with it, and the cam followers 66, 84, 218, 264 are similarly coated with lubricant. In this way, travel of the cam followers 66, 84, 218, 264 relative to the cam paths 68, 86, 220, 221 is facilitated.

While the invention has been described in detail, it will be apparent to one skilled in the art that various changes and modifications can be made and equivalents employed, without departing from the present invention. Although embodiments have been described above with regard to a CABG procedure, the apparatus and method described above are not limited to use in such a procedure. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A method for performing anastomosis between a graft vessel and a target vessel, comprising:
   providing an integrated anastomosis tool comprising
      an anastomosis device having a discard section and a deployable section, where said discard section is connected to said integrated anastomosis tool,
      a crown connected to said discard section, said discard section of said anastomosis device fixed to said crown,
      an expander slidable relative to said crown, and
      a cutter separate from and movable relative to said crown and said expander; and
   actuating at least one control on the single integrated anastomosis tool, wherein results of said actuating include creating an opening in the target vessel with said cutter and deploying said deployable section of said anastomosis device, by moving said crown and said expander, to complete an anastomosis between the graft vessel and the target vessel wherein said deploying causes said anastomosis device to fracture on frangible section between said discard section and said deployable section and removing said discard section after fracture between said discard section and said deployable section.

2. The method of claim 1, wherein said deploying causes at least part of said discard section to hinge relative to at least part of said deployable section.

3. The method of claim 1, wherein said deploying causes at least part of said deployable section to hinge relative to at least part of said discard section.

4. The method of claim 1, wherein said deploying comprises sequentially applying a tensile force, then a compressive force, to the anastomosis device.

5. The method of claim 4, wherein said tensile force is applied to the anastomosis device before said compressive force.

6. The method of claim 4, wherein said applying said compressive force causes said deployable section to separate from said deployable section.

7. A method for performing anastomosis between a graft vessel and a target vessel, each having a wall around a lumen, with an integrated anastomosis tool to which an anastomosis device is detachably connected, comprising:
   providing an integrated anastomosis tool including a cutter;
   storing a quantity of stored energy within said integrated anastomosis tool;
   releasing said quantity of stored energy, wherein said releasing produces an impulsive force on said cutter that advances said cutter through the wall of the target vessel and creates an opening in the wall of the target vessel; and
   deploying the anastomosis device with said integrated anastomosis tool, whereby the graft vessel is connected to the target vessel wherein said integrated anastomosis tool includes a piercing member translationally fixed to said cutter and positioned substantially coaxial with said cutter; wherein said advancing includes simultaneously advancing said piercing member and said cutter wherein the cutter moves no closer to another portion of said piercing member while advancing.

8. The method of claim 7, wherein said releasing advances said cutter through the wall of the target vessel from outside the target vessel.

9. The method of claim 7, further comprising rotating said cutter during at least part of said advancing.

10. The method of claim 7, further comprising providing hemostasis at the opening.

11. The method of claim 7, wherein said storing comprises applying load to a torsional spring.

12. The method of claim 7, wherein said releasing occurs for a duration of substantially 0.05 seconds.

* * * * *